United States Patent
Yodfat et al.

(10) Patent No.: US 9,486,574 B2
(45) Date of Patent: *Nov. 8, 2016

(54) MODULAR SKIN-ADHERABLE SYSTEM FOR MEDICAL FLUID DELIVERY

(71) Applicant: Roche Diagnostics Operations, Inc., Indianapolis, IN (US)

(72) Inventors: Ofer Yodfat, Maccabim-Reut (IL); Yair Dan, Kibut Ein-Harod Ihud (IL); Ofer Arnold, Menashe (IL); Avraham Neta, Gilon (IL); Yossi Shalev, Karkor (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 294 days.

This patent is subject to a terminal disclaimer.

(21) Appl. No.: 14/063,751

(22) Filed: Oct. 25, 2013

(65) Prior Publication Data
US 2014/0052055 A1  Feb. 20, 2014

Related U.S. Application Data

(63) Continuation of application No. 12/937,044, filed as application No. PCT/IL2009/000388 on Apr. 7, 2009, now Pat. No. 8,568,361.

(60) Provisional application No. 61/123,509, filed on Apr. 9, 2008.

(51) Int. Cl.
*A61M 5/315* (2006.01)
*A61M 5/145* (2006.01)
(Continued)

(52) U.S. Cl.
CPC ......... *A61M 5/1456* (2013.01); *A61M 5/1413* (2013.01); *A61M 5/14248* (2013.01);
(Continued)

(58) Field of Classification Search
CPC ......... A61M 5/14248; A61M 5/1413; A61M 5/1456; A61M 2005/14268; A61M 2005/14573

USPC ......................................... 604/131–155, 208
See application file for complete search history.

(56) References Cited

U.S. PATENT DOCUMENTS 3,631,847 A   1/1972  Hobbs, II
3,771,694 A  11/1973  Kaminski
(Continued)

FOREIGN PATENT DOCUMENTS

EP   1732624 B1   10/2008
WO   02068015 A2   9/2002
(Continued)

OTHER PUBLICATIONS

International Search Report & Written Opinion for PCT Application No. PCT/IL2009/000388, mailed Dec. 17, 2009.

*Primary Examiner* — Gerald Landry, II
(74) *Attorney, Agent, or Firm* — Dinsmore & Shohl LLP

(57) ABSTRACT

Disclosed is a portable therapeutic fluid dispensing device. The fluid dispensing device includes a reusable part (100) comprising a reusable part housing including at least a controller and a first portion (186) of a driving mechanism, and a disposable part (200) comprising a disposable part housing including at least a reservoir (220) to retain therapeutic fluid, an outlet port to which the therapeutic fluid is dispensed, a fluid conduit providing fluid communication between the reservoir and the outlet port, and a second portion (112) of the driving mechanism. At least a portion of the disposable part housing defines at least a portion of the reservoir. Also, the second portion of the driving mechanism is mechanically couplable to the first portion of the driving mechanism upon connection of the disposable part to the reusable part.

19 Claims, 60 Drawing Sheets

(51) Int. Cl.
*A61M 5/14* (2006.01)
*A61M 5/142* (2006.01)
*A61M 5/168* (2006.01)
*A61M 5/31* (2006.01)

(52) U.S. Cl.
CPC ........ *A61M5/16854* (2013.01); *A61M 5/1684* (2013.01); *A61M 5/3129* (2013.01); *A61M 2005/1402* (2013.01); *A61M 2005/14252* (2013.01); *A61M 2005/14268* (2013.01); *A61M 2005/14573* (2013.01); *A61M 2005/314* (2013.01); *A61M 2205/186* (2013.01); *A61M 2205/3306* (2013.01); *A61M 2205/3365* (2013.01); *A61M 2205/3389* (2013.01); *A61M 2205/3569* (2013.01); *A61M 2205/3592* (2013.01); *A61M 2209/045* (2013.01)

(56) References Cited

U.S. PATENT DOCUMENTS

| | | | | |
|---|---|---|---|---|
| 4,417,889 | A * | 11/1983 | Choi | A61M 5/14546 604/246 |
| 4,498,843 | A | 2/1985 | Schneider et al. | |
| 4,544,369 | A | 10/1985 | Skakoon et al. | |
| 4,657,486 | A | 4/1987 | Stempfle et al. | |
| 4,715,786 | A | 12/1987 | Wolff et al. | |
| 4,931,041 | A * | 6/1990 | Faeser | A61M 5/1456 128/DIG. 1 |
| 5,830,187 | A | 11/1998 | Kriesel et al. | |
| 5,938,640 | A | 8/1999 | Maget et al. | |
| 5,957,895 | A | 9/1999 | Sage et al. | |
| 6,423,035 | B1 | 7/2002 | Das et al. | |
| 6,485,461 | B1 | 11/2002 | Mason et al. | |
| 6,589,229 | B1 | 7/2003 | Connelly et al. | |
| 6,595,956 | B1 * | 7/2003 | Gross | A61M 5/14248 128/DIG. 12 |
| 6,723,072 | B2 | 4/2004 | Flaherty et al. | |
| 6,740,059 | B2 | 5/2004 | Flaherty | |
| 6,899,699 | B2 * | 5/2005 | Enggaard | A61M 5/20 604/207 |
| 7,018,360 | B2 | 3/2006 | Flaherty et al. | |
| 8,152,477 | B2 | 4/2012 | Anex et al. | |
| 2003/0009133 | A1 * | 1/2003 | Ramey | A61M 5/1456 604/155 |
| 2003/0055323 | A1 * | 3/2003 | Choi | A61B 5/14532 600/316 |
| 2003/0129921 | A1 * | 7/2003 | Small | A63H 33/30 446/475 |
| 2003/0161744 | A1 | 8/2003 | Vilks et al. | |
| 2005/0020980 | A1 * | 1/2005 | Inoue | A61M 5/14244 604/152 |
| 2005/0107743 | A1 | 5/2005 | Fangrow, Jr. | |
| 2005/0165363 | A1 * | 7/2005 | Judson | A61M 5/24 604/209 |
| 2005/0177111 | A1 * | 8/2005 | Ozeri | A61M 5/1456 604/154 |
| 2006/0184119 | A1 * | 8/2006 | Remde | A61M 5/1413 604/151 |
| 2006/0247574 | A1 | 11/2006 | Maule et al. | |
| 2007/0106218 | A1 | 5/2007 | Yodfat et al. | |
| 2007/0224055 | A1 | 9/2007 | Anex et al. | |
| 2008/0021395 | A1 | 1/2008 | Yodfat et al. | |
| 2008/0051710 | A1 | 2/2008 | Moberg et al. | |
| 2008/0051716 | A1 | 2/2008 | Stutz | |
| 2008/0077081 | A1 * | 3/2008 | Mounce | A61M 5/1413 604/67 |
| 2008/0078677 | A1 * | 4/2008 | Chua | G01N 33/20 204/406 |
| 2008/0097381 | A1 | 4/2008 | Moberg et al. | |
| 2008/0214916 | A1 | 9/2008 | Yodfat et al. | |
| 2008/0215035 | A1 | 9/2008 | Yodfat et al. | |
| 2008/0243087 | A1 * | 10/2008 | Enggaard | A61M 5/31553 604/208 |
| 2008/0262440 | A1 * | 10/2008 | Rochette | A61M 5/1458 604/228 |
| 2008/0294142 | A1 | 11/2008 | Patel et al. | |
| 2008/0319414 | A1 | 12/2008 | Yodfat et al. | |
| 2008/0319416 | A1 | 12/2008 | Yodfat et al. | |
| 2009/0143735 | A1 * | 6/2009 | De Polo | A61M 5/1456 604/155 |
| 2010/0243099 | A1 | 9/2010 | Yodfat | |
| 2011/0046565 | A1 * | 2/2011 | Radmer | A61M 5/20 604/211 |

FOREIGN PATENT DOCUMENTS

| | | |
|---|---|---|
| WO | WO-2004110526 A1 | 12/2004 |
| WO | WO-2005072795 A2 | 8/2005 |
| WO | WO-2006121921 A2 | 11/2006 |
| WO | WO-2007052277 A1 | 5/2007 |
| WO | WO-2008024814 A2 | 2/2008 |
| WO | WO-2008078318 A2 | 7/2008 |
| WO | WO-2008139458 A2 | 11/2008 |
| WO | WO-2008139459 A1 | 11/2008 |
| WO | WO-2009001347 A1 | 12/2008 |
| WO | WO-2009001350 A1 | 12/2008 |
| WO | WO-2009013637 A2 | 1/2009 |
| WO | WO-2009013734 A2 | 1/2009 |
| WO | WO-2009013735 A1 | 1/2009 |
| WO | WO-2009013736 A1 | 1/2009 |
| WO | WO-2009016636 A2 | 2/2009 |
| WO | WO-2009016637 A2 | 2/2009 |
| WO | WO-2009081399 A1 | 7/2009 |
| WO | WO-2009113060 A2 | 9/2009 |

\* cited by examiner

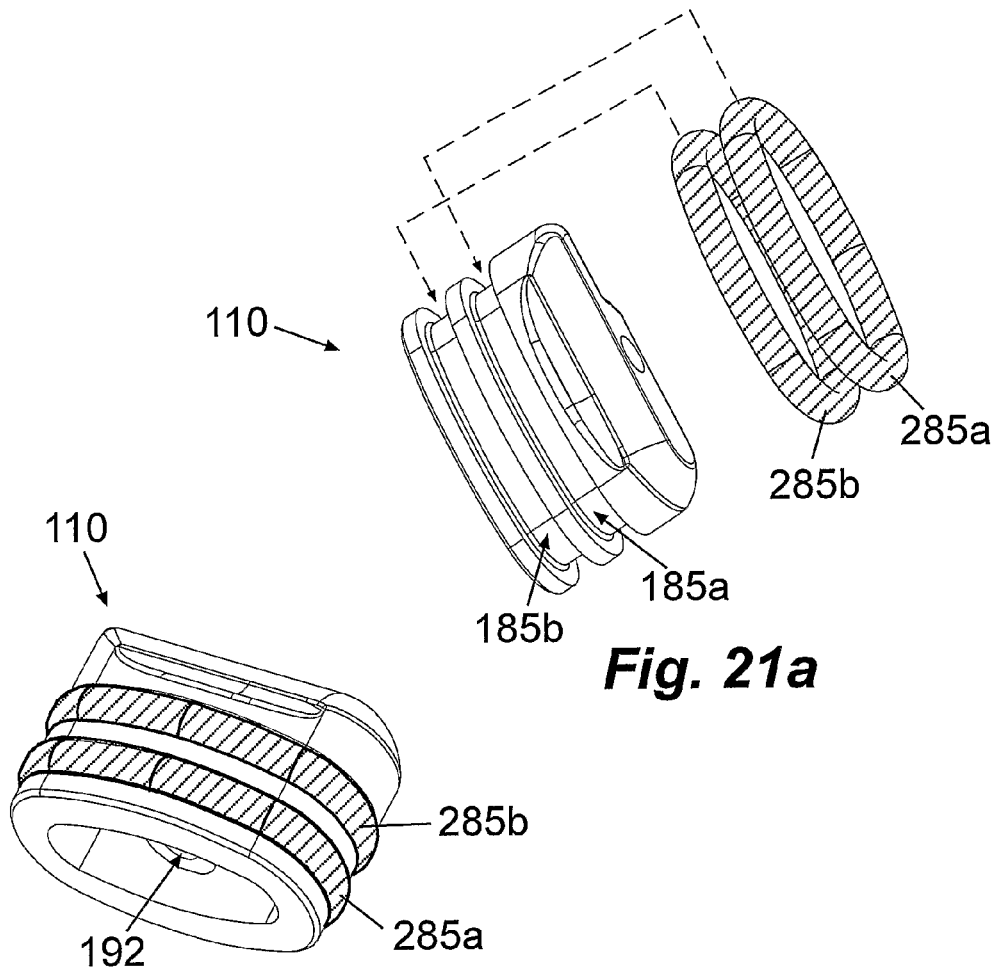
*Fig. 21a*
*Fig. 21b*
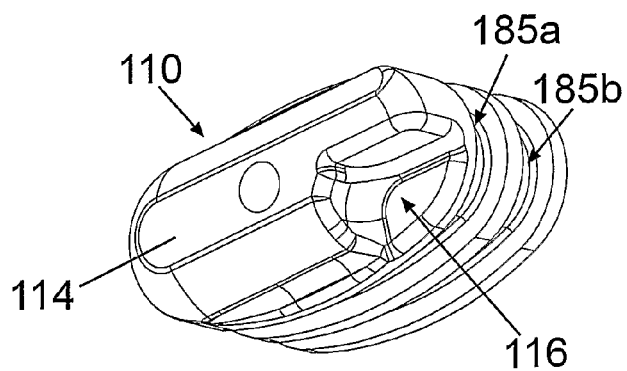
*Fig. 21c*

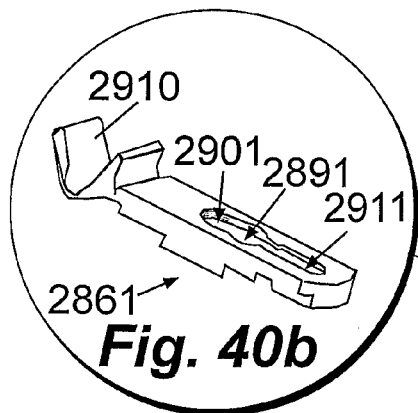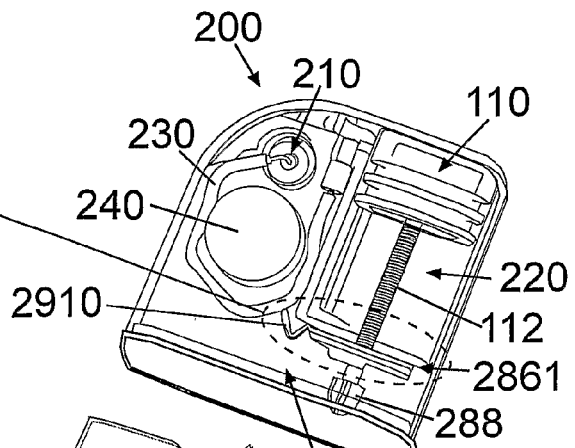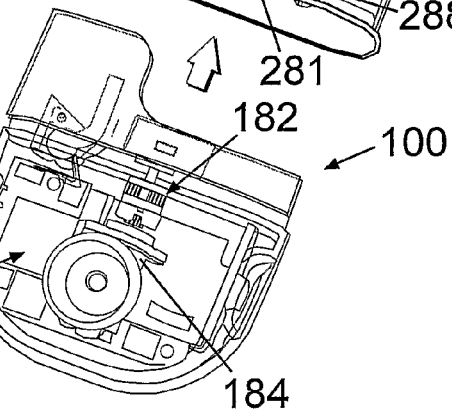
Fig. 40a
Fig. 40b
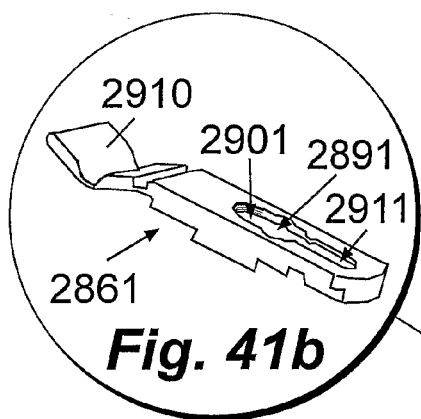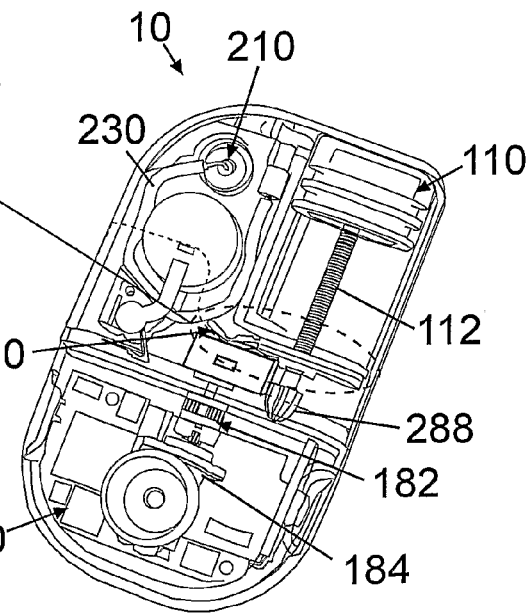
Fig. 41b
Fig. 41a

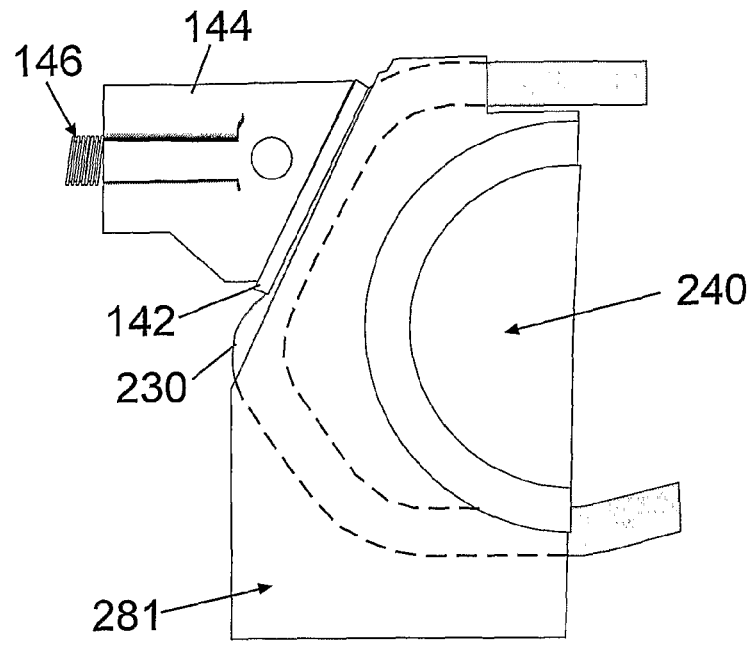
*Fig. 46c*
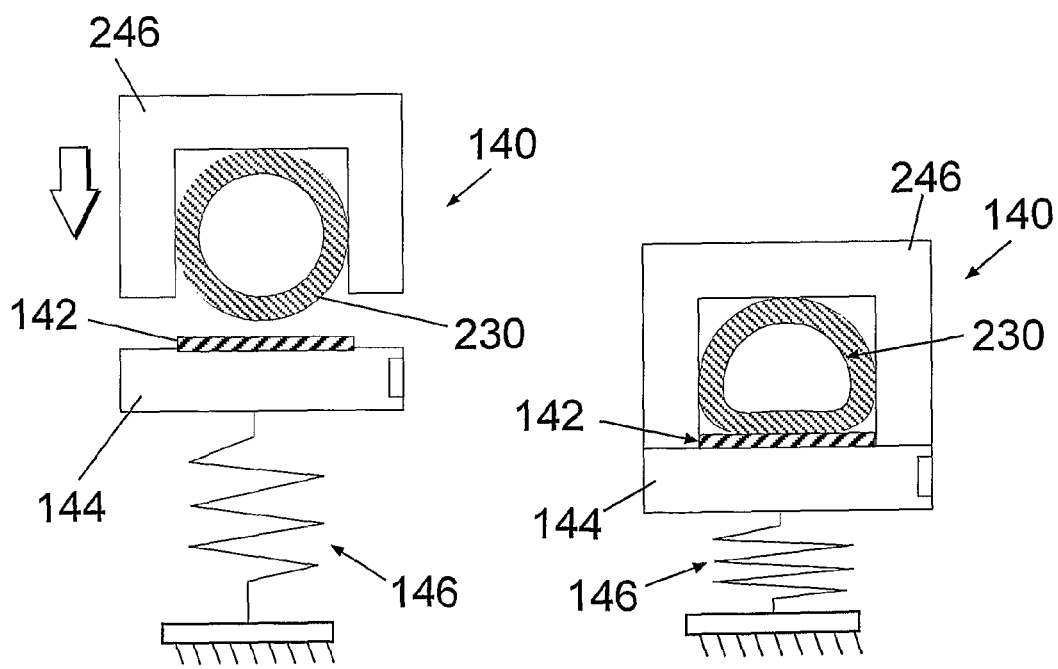
*Fig. 46d*  *Fig. 46e*

MODULAR SKIN-ADHERABLE SYSTEM FOR MEDICAL FLUID DELIVERY

CROSS-REFERENCE TO RELATED APPLICATIONS

This application is a continuation of U.S. patent application Ser. No. 12/937,044 filed on Feb. 25, 2011, now U.S. Pat. No. 8,568,361, which is a 35 U.S.C. 371 national stage entry of International Application No. PCT/IL2009/000388, filed on Apr. 7, 2009, which claims priority to U.S. Provisional Application No. 61/123,509, filed on Apr. 9, 2008, and incorporates disclosures of these applications herein by reference in their entireties.

FIELD

The present disclosure relates generally to systems, devices and methods for dispensing therapeutic fluids (e.g., insulin) to a patient. In particular, the present disclosure relates to portable infusion devices/systems that can be attached to a body of the patient and have a reusable part and a disposable part.

BACKGROUND

Medical treatment of some illnesses requires continuous drug infusion into various body compartments, such as subcutaneous and intra-venous injections. Diabetes mellitus patients, for example, require administration of varying amounts of insulin throughout the day to control their blood glucose levels. In recent years, ambulatory portable insulin infusion pumps have emerged as a superior alternative to multiple daily syringe injections of insulin. These pumps, which deliver insulin at a continuous basal rate as well as in bolus volumes, were developed to liberate patients from repeated self-administered injections, and enable them to maintain a near-normal daily routine. Both basal and bolus volumes generally have to be delivered in relatively precise doses, according to an individual prescription, since an overdose or under-dose of insulin could be fatal.

Several ambulatory insulin infusion devices are currently available on the market. Mostly, these devices comprise a housing containing a driving mechanism, a power source, a controller, electronics and other minor components. Such devices generally include a disposable reservoir, configured as a conventional syringe containing insulin, which is received within the housing, and which is replaced every 2-3 days of operation. A disposable infusion set, which includes a distally located needle/cannula assembly including a cannula and a penetrating member, is connected to the reservoir at its proximal end via a fluid communication tube. Usually, the patient fills the syringe with insulin, attaches the infusion set to an exit port of the syringe, and then inserts the syringe into the pump. After purging air out of the syringe and infusion set, the patient subcutaneously inserts the penetrating member and cannula, at a selected location on the body, and withdraws the penetrating member. To avoid irritation and infection, the subcutaneously inserted cannula must be replaced and discarded after 2-3 days, together with the empty syringe. The syringe plunger is driven by a driving mechanism which includes a threaded-rod (also referred to as a "threaded plunger rod" or "threaded piston rod"), a motor, and controller/electronics. Examples of first generation syringe-type dispensing mechanism are described, for example, in U.S. Pat. No. 3,631,847 to Hobbs, U.S. Pat. No. 3,771,694 to Kaminski, U.S. Pat. No. 4,657,486 to Stempfle, and U.S. Pat. No. 4,544,369 to Skakoon, the contents of all of which are hereby incorporated by reference in their entireties. Other dispensing mechanisms have been also discussed, including peristaltic positive displacement pumps, as described, for example, in U.S. Pat. No. 4,498,843 to Schneider and U.S. Pat. No. 4,715,786 to Wolff, the contents of all of which are hereby incorporated by reference in their entireties.

Although these devices represent an improvement over multiple daily injections, they nevertheless all suffer from several drawbacks. One drawback is the large size and weight of the devices, caused by the configuration and the relatively large size of the driving mechanism and syringe. These relatively bulky devices have to be regularly carried in a patient's pocket or attached to his/her belt. Consequently, the fluid delivery tube of the infusion set is very long, usually greater than 60 cm, in order to enable needle/cannula insertion at remote sites of the body. These uncomfortable, bulky devices and long infusion sets are disfavored by the majority of diabetic insulin users, since they disturb regular activities, such as sleeping and swimming. Furthermore, the effect of the image projected on the teenagers' body is unacceptable. In addition, the use of a delivery tube excludes some standard remote insertion sites, like buttocks, arms and legs.

To avoid the noted consequences of a long delivery tube of the infusion set, a new concept of second generation pumps was proposed. This concept included a remote controlled skin securable (e.g., adherable) device with a housing having a bottom surface adapted to contact patient's skin, a reservoir disposed within the housing, and an injection needle adapted to communicate with the reservoir. These skin adherable devices are disposed of every 2-3 days (similarly to other available pump infusion sets). These devices are described, for example, in U.S. Pat. No. 5,957,895 to Sage, U.S. Pat. No. 6,589,229 to Connelly, and U.S. Pat. No. 6,740,059 to Flaherty, the contents of all of which are hereby incorporated by reference in their entireties. Additional configurations of skin securable pumps are described in U.S. Pat. No. 6,723,072 to Flaherty and U.S. Pat. No. 6,485,461 to Mason, the contents of all of which are hereby incorporated by reference in their entireties.

Second generation skin adherable infusion devices suffer from major drawbacks which include, inter alia, the following:

They are heavy and bulky because:
  The syringe-type reservoir is cylindrical in shape and therefore, if the devices require retaining, for example, 3 ml of deliverable drug, their dimensions are such that they are either long with a small diameter (e.g., 60 mm long, 8 mm inner diameter) or short with large diameter (e.g., 17 mm long, 15 mm inner diameter). These devices' dimensions can result in considerable discomfort to the patient while the device is adhered to his/her skin.
  The cannula insertion mechanism is contained within the housing of the device. Thus, the user has to carry this mechanism (generally a bulky spring loaded mechanism) during the 2-3 operating period of the devices.
The energy supplied generally requires more than one battery, e.g., four batteries.
The costs of using second generation devices is generally high because the entire device, including the relatively expensive components (electronics, driving mechanism, etc.), has to be disposed of every 3 days or so.
Reservoir filling requires an additional syringe to draw the fluid from a container (e.g., a glass bottle) to fill the pump reservoir. This procedure is cumbersome and the risk of accidental piercing by the syringe needle is high.

Second generation devices generally cannot be disconnected from the patient's body, although there are situations in which patients would prefer to temporarily disconnect the pump (e.g., while taking showers, while participating in sports activities, etc.).

The cannula is rigidly secured to the pump housing, and consequently users typically cannot choose cannula length and/or vary the insertion angle.

Insulin wastage—In the event of site-misplacement of the cannula (because of scarred tissue, bleeding, cannula kinking, etc.) the entire device, including the filled insulin reservoir, has to be disposed of.

Device controlling—available wirelessly-controlled pumps do not provide the user with the ability to control the delivery of insulin without the remote control. This can be dangerous in the event the user loses his/her remote control, and may also result in the creation of psychological barriers for the user to trust the pump's operation.

To mitigate the costs issues associated with second-generation devices, and to improve patient's customization of the configuration, functionality and features of their devices, a third generation of skin securable (e.g., adherable) dispensing device was proposed and developed. An example of such a device is described in co-pending/co-owned U.S. patent application Ser. No. 11/397,115 and International Patent Application No. PCT/IL06/001276, the contents of which are hereby incorporated by reference in their entireties. In a third generation device, a dispensing unit is employed, which is composed of two parts: a reusable part, that includes a driving mechanism, electronics, and other relatively expensive components, and a disposable part that includes relatively inexpensive components, such as, for example, a reservoir, a power source (which may form part of the reusable and/or the disposable part, or may be a separate component), etc.

A third generation device provides a more cost-effective solution and enables diverse use of the device. An improvement to a third generation skin securable pump that includes two parts (e.g., a reusable part and a disposable part) is described, for example, in co-pending/co-owned U.S. patent application Ser. No. 12/004,837 and International Patent Application No. PCT/IL07/001,578, the contents of which are hereby incorporated by reference in their entireties. These disclosures include embodiments directed to a device and a method for connection and disconnection of a skin adherable dispensing unit. In some such embodiments, the device includes a cradle unit which is initially adhered to the skin. A cannula is then inserted through the cradle unit into the body of the user. Insertion can be done automatically by a designated inserter, or may be done manually. The dispensing unit of the device can also be connected and disconnected to and from the skin-adhered cradle at the patient's discretion. This concept enables versatile operational modes that include manual and automatic cannula insertion, use of cannulae with various lengths, and also enables cannula insertion at various insertion angles. The cradle is disposable and relatively inexpensive, and may be discarded every 2-3 days. Unlike second generation infusion pumps, in the event of site misplacement of the cannula (due to scarred tissue, bleeding, cannula kinking, etc.) only the cradle and cannula need to be disposed of and replaced, rather than the whole device. Consequently, under those circumstances, the reservoir, still containing unused insulin, can be used when the infusion device is connected to a new cradle/cannula arrangement.

Currently available third generation devices nevertheless have a few drawbacks, including:

Waste of insulin—the disposable reservoir has to be filled to its full capacity, and thus, in situations where the user used less than the full capacity of insulin, some insulin will be discarded (e.g., during three days of operation a user consumes 1 nil, corresponding to 100 Insulin Units, from the available 2 ml in the reservoir, corresponding to 200 IU of insulin, resulting in a waste of 1 ml of insulin)

Reservoir volume cannot be precisely monitored and a "low volume" alert is generally not available.

Filling process requires an accessory syringe to draw insulin from another container (e.g., a vial) to fill the reservoir.

Complexity of components.

Relatively high cost of manufacturing currently available third-generation devices.

SUMMARY OF THE DISCLOSURE

Embodiments of the present disclosure address one or more of the concerns noted above with respect to prior devices.

In some embodiments of the present disclosure, a therapeutic fluid dispensing device/system includes a skin securable (e.g., adherable) dispensing unit that is small, thin, simple, relatively inexpensive, removably connectable to a cradle unit and capable of remote or manual control.

In some embodiments, a therapeutic fluid dispensing device/system is provided that enables reservoir filling to any desired volume, does not require additional syringe for filling, and contains mechanisms to monitor reservoir volume and alert the patient when remaining fluid volume in the reservoir is low.

In some embodiments, a therapeutic fluid dispensing device/system is provided which can be repeatedly connected and disconnected to and from the body in a safe, reliable, and- user friendly manner. Disconnections and reconnections do not affect the dispensing unit components and/or operation, nor harm the surrounding body tissues.

In some embodiments, a therapeutic fluid dispensing device/system is provided which delivers fluid into the body via a soft cannula which is inserted into the body of a user either manually or automatically by a dedicated inserter.

In some embodiments, a therapeutic fluid dispensing device/system is provided which delivers fluid into the body by a soft cannula that can be inserted at any desired angle. The cannula length may be tailored to patients' need.

In some embodiments, a therapeutic fluid dispensing device/system is provided that delivers fluid into the body, where the dispensing device is composed of two parts: a disposable part and a reusable part. The disposable part includes the reservoir and the reusable part includes at least a portion of the driving mechanism and other relatively expensive components. The disposable part may be composed of fewer parts, which are easy to manufacture and assembly and which are relatively inexpensive.

In some embodiments, the disposable part may include a piston-plunger type reservoir system, which is configured as a relatively flat container having a thin profile (e.g., oval-shaped, a profile having 4-arches, etc.). Such a reservoir may serve for drawing fluid from a glass bottle (e.g., insulin vial), and may be filled with various amounts of fluid upon user/patient discretion. Reservoir volume can be monitored and the user alerted to a low volume condition.

In some embodiments, a therapeutic fluid dispensing device/system having a disposable part and a reusable part, where the sealing between the two parts after connection is reliable and does not affect the device's function, is provided.

In some embodiments, a therapeutic fluid dispensing device/system is provided which includes an occlusion sensor to monitor occlusion in the insulin delivery path.

In some embodiments, a device/system that delivers therapeutic fluid into the body is provided which may include a dispensing unit composed of two parts (e.g.;—a reusable part and a disposable part), a skin securable (e.g., adherable) cradle unit, a cannula cartridge unit, and a remote control unit. The dispensing unit can be connected to and disconnected from the skin securable cradle unit. Fluid delivery programming can be performed by buttons/switches disposed on the dispensing unit or by a remote control unit which communicates with the dispensing unit and enables communication of additional user inputs, data acquisition functionality, and data downloading/transfer operations.

In some embodiments, the device can further include a cannula cartridge unit that can be loaded into a dedicated inserter. The cartridge may include a subcutaneously insertable cannula having a cannula hub at its proximal end, a penetrating member which pierces the skin and is withdrawn after cannula insertion, and a protective case (a "protector") that contains the cannula and the penetrating member to maintain cannula sterility and to avoid unintentional self-piercing. The cannula cartridge unit is configured to be fitted within a "well" of the cradle unit which, in some embodiments, is a protrusion encircling a passageway enabling the insertion and placement of the cannula in a subcutaneous compartment of the patient's body and rigidly connecting the cannula hub to the cradle. The cannula can be inserted in various angles in relation to the skin surface. The cannula can be configured in various lengths to be tailored to a patient's need.

In some embodiments, the cannula hub proximal end includes a self sealable rubber septum that can be pierced by a connecting lumen that emerges from the outlet port of the dispensing unit for maintaining fluid communication between the reservoir and the subcutaneously placed cannula.

In some embodiments, the cradle unit and/or cannula cartridge unit can be placed manually or by a dedicated insertion device referred-to as "inserter". Withdrawal of the penetrating member after the subcutaneous insertion of the cannula can be performed manually or automatically by the inserter.

In some embodiments, the dispensing device/unit includes a reusable part including at least a portion of a driving mechanism to drive a plunger or piston, electronics, and other relatively expensive components, and the disposable part includes the relatively inexpensive components such as a reservoir, a fluid connecting tube, an outlet port, a connecting lumen, a piston, and a power source configured to supply power to the dispensing unit. The piston is adapted to be received within the reservoir and is configured to force (displace) therapeutic fluid from the reservoir into a connecting tube. The piston and reservoir are configured to have an oval shape with a thin profile. The disposable part can further include a portion of the driving mechanism.

In some embodiments, the driving mechanism is shared by both parts of the dispensing unit and includes, for example:

In the reusable part: a motor, gears and a rotating cylinder having an inwardly oriented thread (referred-to as "sleeve" or "drive sleeve"), which, in some embodiments, may be star shaped.

In the disposable part: a threaded piston rod having a piston at its distal end and a tip (also referred to as "driving tip") with teeth/ribs at its proximal end (referred to as "juice extractor"), and an engagement member.

In some embodiments, the tip (or "juice extractor") is configured to fit within the sleeve upon attachment of the reusable and disposable parts. The engagement member is configured to function in two modes: a first mode enabling free movement of the piston rod, and a second mode enabling a controlled movement of the piston rod.

In some embodiment, the first mode of the engagement member enables filling of the reservoir, and the second mode of the engagement member enables linear displacement of the piston received within the reservoir to cause delivery of therapeutic fluid into the patient's body.

In some embodiments, each one of the parts of the dispensing device/unit has a separate housing. The housing of the reusable part may contain a reusable chassis to accommodate various components (e.g., electronics) and the housing of the disposable part may contain a disposable chassis to accommodate the disposable components (e.g., a connecting tube).

In some embodiments, the reservoir and housing(s) of the dispensing device are configured to have a non-circular cross-section (e.g. ellipse, oval, 4 curves, 8 curves) so that the dispensing unit has relatively small dimensions and/or a thin profile.

In some embodiments, the reservoir is an integral part of the housing of the disposable part of the dispensing device.

In some embodiments, the two-part dispensing unit including the driving mechanism with the engagements member, a juice extractor and a sleeve enables the user to fill the reservoir with any desired volume of therapeutic fluid. The reservoir can be filled without use of an auxiliary syringe and may require a dedicated adapter.

In some embodiments, the dispensing unit includes a sensor to monitor the amount of fluid contained within the reservoir. In particular, the sensor can alert the patient when the volume of the fluid contained within the reservoir is low.

In some embodiments, the dispensing unit includes a sensor to monitor occlusion in the connecting tube and/or the cannula. In particular, the sensor can comprise two parts: a reusable sensor portion located in the reusable part and a disposable sensor portion located in the disposable part of the dispensing device.

In some embodiments, the reusable part of a dispensing unit includes connectors to enable electrical connection between a power source located in the disposable part and various energy consuming components, such as electronics, which are located in the reusable part.

In some embodiments, the housing of the dispensing unit includes a vent port/aperture (which may be located in the reusable part) to enable air passage between the internal cavity of the dispensing unit and the surrounding. Such a vent port/aperture may be sealed by a selective membrane to enable air passage while preventing liquids ingression into the internal cavity of the dispensing unit.

In some embodiments, the two part dispensing unit is waterproof after connection of the reusable part and disposable part. Sealing can be achieved by at least one seal/gasket (e.g., a rubber O-ring/gasket) located in the disposable and/or reusable parts.

In some embodiments, the device includes a notifier (i.e., notification mechanism such as one or more types of user output interfaces) to notify/alert the user. The notifier can be, for example, visual (e.g., a display), audible (e.g., a buzzer) or vibratory (e.g., a vibrator), or a combination thereof, and can be located in the dispensing unit, the remote control unit or both.

In some embodiments, the device can further comprise a sensing apparatus (e.g., sensor) to sense and monitor bodily analyte(s), e.g., glucose. The analyte(s) sensing can be performed using electrodes disposed on the cannula. Embodiments which comprise both dispensing apparatus and sensing apparatus can be referred-to as "system" and if fluid is dispensed according to sensed analyte levels, the system can then be referred to as a "closed loop system".

In some embodiments of the present disclosure, a method to control delivery of fluid to the body of a patient using the above mentioned device/system is described.

In one aspect, a portable therapeutic fluid dispensing device is disclosed. The fluid dispensing device includes a reusable part comprising a reusable part housing including at least a controller and a first portion of a driving mechanism, and a disposable part comprising a disposable part housing including at least a reservoir to retain therapeutic fluid, an outlet port to which the therapeutic fluid is dispensed, a fluid conduit providing fluid communication between the reservoir and the outlet port, and a second portion of the driving mechanism. At least a portion of the disposable part housing defines at least a portion of the reservoir. Also, the second portion of the driving mechanism is mechanically couplable to the first portion of the driving mechanism upon connection of the disposable part to the reusable part.

Embodiments of the fluid dispensing device may include one or more of the following features.

The device may be skin-adherable.

The disposable part housing may include a skin-adherable base configured to receive the reusable part housing.

At least one of the reusable part and/or the disposable part may include at least one chassis configured to be received in the respective one of the reusable part housing and the disposable part housing and provide structural support for one or more components of the respective one of the reusable part and the disposable part.

At least one of a reusable part chassis, the reusable part housing, a disposable part chassis and/or the disposable part housing may include at least one gasket to establish device-sealing condition upon connection of the reusable part and the disposable part.

At least one of a reusable part chassis and/or the reusable part housing may include one or more latches configured to mate with corresponding one or more recesses defined on at least one of a disposable part chassis and/or the disposable part housing such that the reusable part is connectable to the disposable part.

At least one of a reusable part chassis and/or the reusable part housing may include one or more recesses configured to receive corresponding one or more latches included with at least one of a disposable part chassis and/or the disposable part housing such that the reusable part is connectable to the disposable part.

The first portion of the driving mechanism may include at least one of, for example, a motor, one or more cogwheels actuated by the motor and/or a drive sleeve in mechanical connection with the one or more cogwheels such that rotational force transferred by the one or more cogwheels causes rotational movement of the drive sleeve. The one or more cogwheels may form part of a planetary gear system, where the planetary gear system may further include a housing having an interior which is at least partially threaded to house the one or more cogwheels. The drive sleeve may include a hollow cylinder, at least a portion of the hollow cylinder having a plurality of teeth defined along a circumference of the at least the portion of the hollow cylinder, the plurality of teeth configured to mechanically interact with the one or more cogwheels of the first part of the driving mechanism.

The fluid dispensing device may further include one or more monitoring mechanisms to monitor operation of the at least one of, for example, the motor, the one or more cogwheels and/or the drive sleeve. The one or more monitoring mechanisms may include at least one of, for example, a radiation source emitting radiation traveling in a direction substantially perpendicular to the longitudinal axis of a shaft of the motor, a flag wheel including at least one rotatable portion of a disc coupled to the shaft of the motor at a position where, upon rotation of the shaft and the at least one portion of the disc, the flag wheel periodically blocks the emitted radiation from propagating in the direction of radiation and/or a radiation detector positioned to intercept at least some of the radiation emitted by the radiation source when the emitted radiation is not blocked by the at least one portion of the disc. The radiation detector may further be configured to generate a signal in response to detection of the at least some of the radiation and transmit the signal to a processor of the controller to process the signal.

The second portion of the driving mechanism may include at least One of, for example, a piston, a piston rod mechanically coupled at a first end of the piston rod to the piston, a driving tip mechanically coupled to the piston rod at a second end of the piston rod, the driving tip configured to mechanically interact with the first portion of the driving mechanism upon connection of the reusable part and the disposable part, and/or an engagement member coupled to the piston rod, the engagement member configured to selectively enable controlled displacement of the piston rod and substantially unrestricted displacement of the piston rod within at least the reservoir of the disposable part.

The piston rod may include a threaded rod. The piston may further include at least one gasket disposed on the exterior of the piston adapted for at least one of, for example, preventing fluid leakage from the reservoir and/or stabilizing the piston within the reservoir. The at least one gasket disposed on the exterior of the piston may include at least one lubricated gasket to reduce friction with walls of the reservoir. The piston may include a cavity to receive the first end of the piston rod. The cavity of the piston may be connectable to the first end of the piston rod to enable at least one of, for example, pushing of the piston using the piston rod and/or pulling of the piston using the piston rod and/or unrestricted rotation of the first end of the piston rod within the piston cavity. The cavity of the piston may be connectable to the first end of the piston rod such that when connected the cavity and the first end form a snap-fit.

The driving tip may be selected from the group consisting of, for example, a driving tip integrally coupled to the piston rod and/or a modular driving tip manufactured separately from the piston rod and configured to be assembled to the piston rod.

The driving tip may include a plurality of ridges spaced apart from one another along the circumference of the tip, the driving tip being receivable within a drive sleeve of the first portion of the driving mechanism mechanically coupled to a motor through one or more cogwheels. The drive sleeve may include a plurality of grooves within the sleeve, the grooves being spaced apart from one another to correspond to the spacing of the plurality of ridges of the driving tip. The grooves within the drive sleeve may be substantially parallel to the longitudinal axis of the drive sleeve.

The engagement member may be configured for threaded engagement with the piston rod. The engagement member may be further configured to be disengaged from the piston rod to provide substantially unrestricted movement of the piston rod when disengaged from the engagement member. The engagement member may include a first opening and a second opening, at least a portion of the second opening may be threaded. When the engagement member is positioned in a first position, a threaded piston rod may be placed in the first opening and be configured to linearly move substantially unrestricted. When the engagement member is positioned in a second position, the threaded piston rod may be placed in the second opening and be configured to linearly move upon rotation of the threaded piston rod. The engagement member may be displaceable from the first position to the second position by one of, for example, automatic displacement upon connection of the reusable part and the disposable part and/or manual displacement.

The engagement member may further include an extension extending from the engagement member that, when actuated, causes the engagement member to move from the first position to the second position. The extension piece may be actuated by an actuator, resulting from connection of the reusable part and the disposable part. The actuator may include a planetary gear system having one or more cogwheels of the first portion of the driving mechanism.

At least a portion of the disposable part housing may include one or more reinforcing ribs.

At least a portion of the disposable part housing may be transparent. The at least the portion that is transparent may include at least a part of the reservoir.

The at least the portion of the disposable part housing defining the at least a portion of the reservoir may include at least one scale of graduations.

The at least a portion of the reservoir may be lubricated to reduce friction between a piston and walls of the reservoir.

The reservoir may include cross-sectional configuration selected from the group consisting of, for example, a round configuration, an oval configuration, an elliptical configuration, a multi-curved configuration and/or a substantially rectangular configuration.

The piston may include a cross-sectional configuration selected from the group consisting of, for example, a round configuration, an oval configuration, an elliptical configuration, a multi-curved configuration and/or a substantially rectangular configuration.

The fluid conduit may include a channel defined within the disposable part housing.

The fluid conduit may include at least one elastic region. The at least one elastic region may include a tube accommodated in a chassis of the disposable part, where an end of the tube may include a nipple connectable to the disposable part housing to establish fluid communication between the reservoir and the tube upon assembly of the chassis of the disposable part into the disposable part housing.

The reusable part housing may include an aperture defined on an external surface of the reusable part housing, the aperture leading into an internal cavity defined in the reusable part housing to enable air passage into the internal cavity.

The reusable part may further include one or more user-actuated buttons actuatable by a user to specify control instructions for a processor of the controller, the control instructions being related to operation of the fluid dispensing device.

The reusable part may further include a Printed Circuit Board having at least one rigid portion and at least one flexible portion.

The reusable part may further include at least one notifier to generate notifications to a user based on signals transmitted by the controller.

The reusable part may further include a transceiver to perform at least one of, for example, transmitting to a remote control unit and/or receiving transmissions from the remote control unit.

At least one of the reusable part and the disposable part may further include a power source. The reusable part may include a capacitor electrically coupled to the power source, the capacitor configured to store energy provided by the power source.

The disposable part may include the power source, and the reusable-part may include electrical connectors electrically coupled to the power source of the disposable part, and at least one electronic component in electrical communication with the power source through the electrical connectors. Each of the electrical connectors may include a first connecting end electrically coupled to the at least one electronic component, and a second connecting end electrically coupled to the power source of the disposable part. The second connecting end of the each of the electrical connectors may include a resilient connecting end configured as a spring. One or more of the reusable part housing and a reusable part chassis configured to be received in the reusable part housing may include a rigid extension accommodating the electrical connectors, the rigid extension configured to provide one or more of, for example, structural support to the electrical connectors and/or protection of the electrical connectors.

The reusable part may further include a mechanism to monitor fluid levels inside the reservoir, the mechanism including at least one energy source, at least one energy detector to detect energy emitted by the at least one energy source and to generate a signal to be processed by a processor, and a regulator to regulate the level of energy received by the at least one energy detector based, at least in part, on the fluid level in the reservoir.

The regulator may include a piston rod displaceable within an inner channel defined in a drive sleeve of the first portion of the driving mechanism. The at least one energy source and the at least one energy detector may be positioned opposite each other and on opposite sides the drive sleeve, and the drive sleeve may have at least one opening establishing an optical path between the at least one energy source and the at least one energy detector when the piston rod does not block the at least one opening.

The at least one energy detector may be configured to detect the emitted energy when the piston rod is linearly displaced within the drive sleeve to a position where the piston rod does not block the at least one opening to enable passage of the emitted energy in the optical path between the at least one energy source and the at least one energy detector.

The mechanism to monitor fluid level may be configured to enable detection of several positions of the piston rod corresponding to several levels of fluid inside the reservoir. The mechanism may include a plurality of energy sources, and a plurality of energy detectors, the drive sleeve including a plurality of sets of opposite openings, and each of the plurality of energy sources may be configured to emit radiation to pass through a corresponding set of the plurality of sets of opposite openings. When not blocked by the piston rod, the emitted radiation may be detected by a corresponding one of the plurality of the energy detectors.

The signal generated by the at least one energy detector may be indicative that the fluid level inside the reservoir reached a predetermined threshold. The processor may be configured to determine, at least in part based on the signal generated by the at least one energy detector, a level of the fluid inside the reservoir, and provide a notification to a user via one or more of, for example, a notification component in the reusable part and a remote control.

The regulator may include a piston rod displaceable within an inner channel defined in a drive sleeve of the first portion of the driving mechanism, the at least one energy source and the at least one energy detector may be disposed on the same side of the drive sleeve. The at least one energy detector may be configured to receive and detect, in accordance with positions of the piston rod, at least some of the energy emitted by the at least one energy source and reflected by surfaces of the piston rod through an opening in the drive sleeve.

The reusable part may further include a mechanism to monitor fluid levels inside the reservoir, the mechanism including a magnetic coil surrounding at least a portion of a drive sleeve of the first portion of the driving mechanism, the drive sleeve configured to receive a piston rod, the piston rod being displaceable within an inner channel defined in the sleeve. At least a portion of the piston rod may include metallic material. Displacement of the piston rod within the drive sleeve may cause a change in the inductance level of the magnetic coil corresponding to a position of the piston rod within the drive sleeve, the position of the piston rod within the drive sleeve corresponding to a respective fluid level in the reservoir.

The fluid dispensing device may further include an occlusion sensor to detect occlusion in a fluid path from the reservoir to a body of a user. The occlusion sensor may include a first portion disposed within the reusable part, the first portion including at least a sensing element and a spring biased platform, and a second portion disposed within the disposable part, the second portion including at least a track formed in a disposable part chassis received within the disposable part housing, the track configured to accommodate at least a portion of a flexible fluid delivery tube of the fluid conduit. The sensing element may be configured to be pressed against the delivery tube upon connection of the reusable and disposable parts such that an increase in the pressure within the delivery tube causes an increase in the forces exerted on the sensing element. The sensing element may further be configured to generate a signal transmitted to a processor of the controller corresponding to the level of sensed forces exerted on the sensing element. When the level of sensed forces exerted on the sensing element exceeds a predetermined threshold, the signal may be indicative that an occlusion state has been reached.

The controller may be configured to provide a notification to a user, in response to receipt of the signal indicative that the state of occlusion has been reached, via one or more of, for example, a notification component in the reusable part and/or a remote control. The controller may be configured to automatically suspend operation of the fluid dispensing device in response to receipt of the signal indicative that the state of occlusion has been reached.

The fluid dispensing device may further include a handle having a first end removeably connectable to the driving tip coupled to the piston rod, and a second end configured to be gripped by a user. The handle may be configured to facilitate pushing and pulling the piston rod into and away from the reservoir.

The fluid dispensing device may further include an analyte sensor to monitor analyte concentration levels in a body of a patient. The fluid dispensing device may be configured to operate in one or more of, for example, a closed-loop mode wherein therapeutic fluid dispensing is based, at least in part, on the monitored analyte concentration levels, a semi-closed loop mode wherein the therapeutic fluid dispensing is based, at least in part, on the monitored analyte concentration levels and input from the patient and/or an open loop mode wherein the therapeutic fluid dispensing is independent of the monitored analyte concentration levels. The fluid dispensing device may further include a subcutaneously insertable cannula configured to deliver the dispensed therapeutic fluid into the body of the patient. The subcutaneously insertable cannula may include the analyte sensor.

In another aspect, a fluid dispensing system is disclosed. The system includes the portable fluid device described above, a remote control unit to control operation of at least the portable fluid dispensing device, and a skin-adherable cradle connectable to the fluid dispensing device such that the fluid dispensing device can be removably connected to the skin-adhereable cradle.

Embodiments of the system may include any one or more of the features described above in relation to the fluid dispensing device, as well as one or more of the following features.

The fluid dispensing system may further include a cannula cartridge unit including a cannula hub having an opening sealed at one end by a self-sealable septum, a cannula having an inner channel, the cannula coupled to the cannula hub at the opening, and a removable penetrating member fitted within the inner channel of the cannula, the removable penetrating member configured to be removed from the cannula upon subcutaneous insertion of the cannula.

The remote control unit may include at least one of, for example, a display and/or operating buttons. The display of the remote control unit may include a touch-sensitive display.

The remote control unit may be adapted to perform at least one of, for example, provide operating instructions to the fluid dispensing device and/or receive from the fluid dispensing device one or more of alerts and/or status indications.

The remote control unit may be implemented using a device selected from a group consisting of, for example, a personal computer, a laptop, a music or multimedia player, a PDA, a cellular phone, a watch and/or a remote control.

The remote control unit may be configured to communicate with the fluid dispensing device using a mode of communication selected from a group consisting of, for example, wireless communication, wired communication, wire line communication, RF communication, IR communication and/or induction-based communication.

The remote control unit may further include an analyte sensor to determine analyte concentration levels in a body of a user. The analyte may include glucose.

The remote control unit may further include a port to receive a test strip containing a blood sample of the user, the analyte sensor being configured to determine the analyte concentration level in the blood of the user.

In a further aspect, a method for dispensing therapeutic fluid is disclosed. The method includes connecting a fluid dispensing device reusable part including a first portion driving mechanism to a disposable part of the fluid dispensing device, the disposable part including a second portion of the driving mechanism. The method also includes controllably actuating the first portion of the driving mechanism to cause the second portion of the driving mechanism to dispense therapeutic fluid contained in a reservoir in the disposable part through an outlet port of the disposable part, the therapeutic fluid delivered to the outlet port through a fluid conduit in the disposable part connecting the reservoir to the outlet port.

Embodiments of the method may include any one or more of the features described above in relation to the fluid dispensing device and the fluid dispensing system.

In another aspect, a method for monitoring fluid levels in a reservoir of a fluid dispensing device having at least a reservoir to retain fluid, a driving mechanism for displacing the fluid from the reservoir, a controller and a mechanism for monitoring fluid levels is disclosed. The method includes activating the driving mechanism and the mechanism for monitoring fluid levels in the reservoir, monitoring the position of a displaceable piston rod of the driving mechanism, generating a signal for processing by a processor of the controller, and determining the level of fluid in the reservoir based, at least in part, on the received signal.

Embodiments of the method may include any one or more of the features described above in relation to the fluid dispensing device, the fluid dispensing system, the above-described methods, as well as one or more of the following features.

The method may further include generating a notification to a user upon determining the level of fluid in the reservoir.

The mechanism for monitoring fluid levels in the reservoir may include at least one component selected from a group consisting of, for example, an energy source, an energy detector, a magnetic coil and/or a "Hall effect sensor".

In a further aspect, a method for detecting occlusion in a fluid path from a reservoir of a fluid dispensing device to a body of a user is disclosed. The method includes providing a fluid dispensing device comprising at least one reservoir for retaining therapeutic fluid and a flexible fluid delivery tube to deliver the therapeutic fluid, providing an occlusion sensor comprising at least a sensing element pressed against the delivery tube, generating a signal representative of a level of force exerted on the sensing element by the delivery tube as a result of an increase in pressure in the delivery tube, and determining, based on the signal representative of the level of force, if a state of occlusion has been reached.

Embodiments of the method may include any one or more of the features described above in relation to the fluid dispensing device, the fluid dispensing system, the above-described methods, as well as one or more of the following features.

The method may further include generating a notification to the user upon determining that the state of occlusion has been reached.

The method may further include suspending the operation of the fluid dispensing device upon determining that a state of occlusion has been reached.

The occlusion sensor may further include a first portion including at least the sensing element, and a second portion including at least a structure to support the delivery tube.

The method for detecting occlusion may further include coupling the first portion to the second portion prior to generating the signal.

In an additional aspect, an adapter to enable transfer of therapeutic fluid to the reservoir of the fluid dispensing device described above is disclosed. The adapter includes a first connecting end for releasable attachment to a container of the therapeutic fluid, and a second connecting end for releasable attachment to the disposable part of the fluid dispensing device.

Embodiments of the adapter may include any one or more of the features described above in relation to the fluid dispensing device, the fluid dispensing system, the above-described methods, as well as one or more of the following features.

The first connecting end may include a needle to pierce a sealing cover of the therapeutic fluid container and establish fluid communication between the container and the adapter. The first connecting end may further include a circular wall defining a depression to receive a circular neck of the therapeutic fluid container.

The second connecting end may include an opening to be fitted into the outlet port of the disposable part. The opening of the second connecting end may be sealed by a self-sealable septum configured to be pierced by a connecting lumen of the disposable part upon connection of the adapter to the disposable part. The opening of the second connecting end may be in fluid communication with a needle in the first connecting end, the needle being configured to pierce a sealing cover of the therapeutic fluid container and establish fluid communication between the container and the adapter.

The second connecting end may further include a wall configured to match contours of the disposable part and to support the adapter against the disposable part housing after connection of the adapter to the disposable part.

In a further aspect, a method for filling a reservoir disposed within a fluid dispensing device with therapeutic fluid is disclosed. The dispensing device has at least a disposable part comprising a housing including a reservoir to retain therapeutic fluid, an outlet port, and a portion of a driving mechanism, the disposable part being connectable to a reusable part having another portion of the driving mechanism. At least a portion of the housing defines at least a portion of the reservoir. The method includes providing the disposable part of the fluid dispensing device, providing an adapter having a first connecting end for releasable attachment to a container of the therapeutic fluid, and a second connecting end for releasable attachment to the outlet port of the fluid dispensing device, and attaching the first connecting end of the adapter to the container of the therapeutic fluid such that a needle of the first connecting end of the adapter pierces a sealing cover of the container and establishes fluid communication between the container and the adapter. The method further includes attaching the second connecting end of the adapter to the outlet port of the disposable part such that a connecting lumen of the outlet port pierces a septum of the second connecting end of the adapter and establishes fluid communication between the adapter and the outlet port. The method also includes pulling a piston rod of the portion of the driving mechanism included in the disposable part to cause at least some of the therapeutic fluid in the container to flow through the adapter and into the reservoir via the outlet port.

Embodiments of the method may include any one or more of the features described above in relation to the fluid dispensing device, the fluid dispensing system, the adapter, the above-described methods, as well as one or more of the following features.

The method may further include pushing the piston rod to remove air from the reservoir.

The method may further include detaching the second connecting end of the adapter from the outlet port of the disposable part.

The method may further include using a handle attached to the piston rod for at least one of, for example, pulling the piston rod and/or pushing the piston rod.

In a further aspect, a fluid level sensor to measure fluid level in a container containing fluid displaced by movement of a driving mechanism is disclosed. The fluid level sensor may include at least one energy source, at least one energy detector to detect energy emitted by the at least one energy source and to generate a signal to be processed by a processor, and a regulator to regulate the level of energy received by the at least one energy detector based, at least in part, on the fluid level in the container.

Embodiments of the fluid level sensor may include any one or more of the features described above in relation to the fluid dispensing device, the fluid dispensing system, the adapter, the above-described methods, as well as one or more of the following features.

The regulator may include a piston rod of the driving mechanism, the piston being displaceable within an inner channel defined in a drive sleeve coupled to a motor of the driving mechanism, the at least one energy source and the at least one energy detector being positioned opposite each other and on opposite sides the drive sleeve, and the drive sleeve having at least one opening establishing an optical path between the at least one energy source and the at least one energy detector when the piston rod does not block the at least one opening.

The at least one energy detector may be configured to detect the emitted energy when the piston rod is linearly displaced within the drive sleeve to a position where the piston rod does not block the at least one opening to enable passage of the emitted energy in the optical path between the at least one energy source and the at least one energy detector.

In another aspect, a fluid level sensor for monitoring fluid levels inside a reservoir containing fluid displaced by movement of a driving mechanism is disclosed. The fluid level sensor includes a magnetic coil surrounding at least a portion of a drive sleeve coupled to a motor of the driving mechanism, the drive sleeve configured to receive a piston rod of the driving mechanism, the piston rod being displaceable within an inner channel defined in the sleeve. At least a portion of the piston rod includes metallic material. Displacement of the piston rod within the drive sleeve causes a change in the inductance level of the magnetic coil corresponding to a position of the piston rod within the drive sleeve, the position of the piston rod within the drive sleeve corresponding to a respective fluid level in the reservoir.

Embodiments of the fluid level sensor may include any one or more of the features described above in relation to the fluid dispensing device, the fluid dispensing system, the adapter, the first described fluid level sensor and the above-described methods.

In yet an additional aspect, an occlusion sensor to sense a state of occlusion occurring within a fluid path including at least a fluid delivery tube is disclosed. The occlusion sensor includes a sensing element configured to be pressed against the fluid delivery tube, the sensing element further configured to generate a signal representative of a level of force exerted on the sensing element by the delivery tube as a result of an increase in pressure in the delivery tube.

Embodiments of the occlusion sensor may include any one or more of the features described above in relation to the fluid dispensing device, the fluid dispensing system, the adapter, the fluid level sensors, the above-described methods, as well as one or more of the following features.

The occlusion sensor may further include a controller to determine if the state of occlusion has been reached based on the signal generated by the sensing element that is representative of the level of force exerted on the sensing element, the controller being further configured to perform, upon determining that the state of occlusion has been reached, one or more of, for example, provide a notification to a user that the state of occlusion has been reached and/or automatically suspend fluid delivery operations.

In another aspect, an adapter to facilitate transfer of fluid from a first container containing the fluid to a second container disposed in a housing is disclosed. The adapter includes a first connecting end for releasable attachment to the first container of the fluid, the adapter including a needle to pierce a sealing cover of the fluid container and establish fluid communication between the first container and the adapter. The adapter also includes a second connecting end for releasable attachment to a port on the housing.

Embodiments of the adapter may include any one or more of the features described above in relation to the fluid dispensing device, the fluid dispensing system, the first adapter described above, the fluid level sensors, the occlusion sensor, the above-described methods, as well as the following feature.

The second connecting end may include an opening to be fitted into the port of the housing, the opening of the second connecting end being sealed by a self-sealable septum configured to be pierced by a connecting lumen of the housing to establish fluid communication between the adapter and the second container disposed in the housing.

Throughout the entirety of the present disclosure, use of the terms "comprising", "including," "containing," and any other similar synonymous terms, is inclusive or open-ended and does not exclude additional, non-recited or non-described elements or operations.

Throughout the entirety of the present disclosure, use of particular terminology is not intended to restrict or narrow in anyway whatsoever the descriptions and embodiments of the present disclosure. Rather, embodiments and descriptions that could have been described using synonymous and/or equivalent terminology are also contemplated as coming within the scope the present disclosure and/or the claims.

Details of one or more implementations are set forth in the accompanying drawings and in the description below. Further features, aspects, and advantages will become apparent from the description, the drawings, and the claims.

BRIEF DESCRIPTION OF THE DRAWINGS

Embodiments of the present disclosure are described with reference to the accompanying drawings. In the drawings, like reference numbers indicate identical or functionally similar elements.

FIGS. 21a-21c are views and diagram of a piston.

FIGS. 40a-40b are views and diagrams of a two-part dispensing device before connection, and an automatic engagement mechanism.

FIGS. 41a-41b are views and diagrams of a two-part dispensing device after connection, and an automatic engagement mechanism.

FIGS. 46a-46e are diagrams of an occlusion sensor deployed in a two-part dispensing unit.

DETAILED DESCRIPTION

Figure 1:
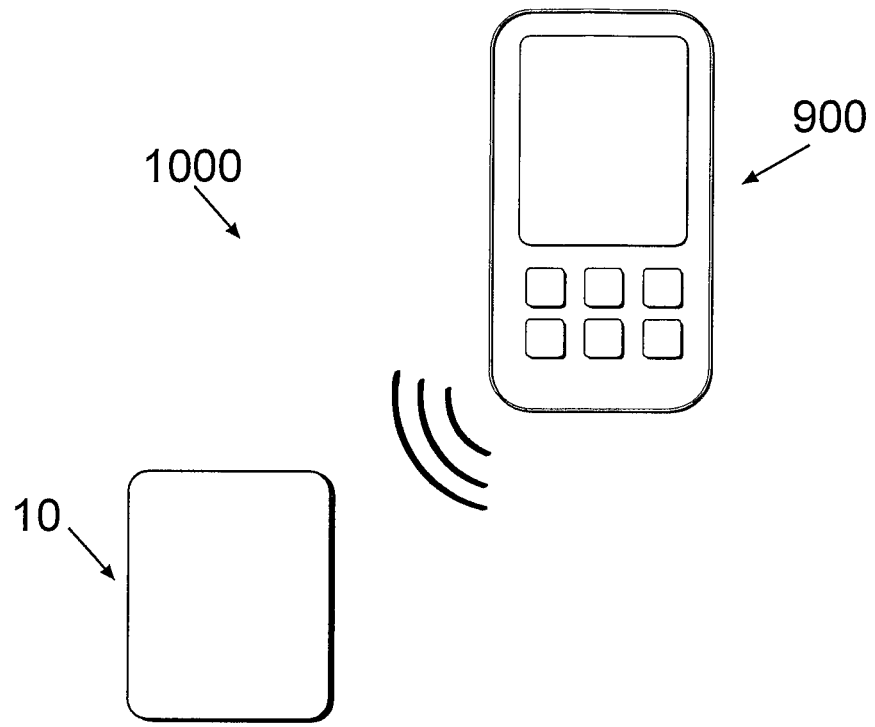
FIG. 1 is a schematic diagram of a fluid delivery system that includes a dispensing unit and a remote control unit.

The present disclosure generally relates to delivery of therapeutic fluid(s) to patients and in particular, to portable therapeutic fluid dispensing/delivery/infusion devices (as used herein, the terms dispensing, delivery and infusion are interchangeable), systems and methods for delivery of a therapeutic fluid (e.g., insulin) to a patient. In some embodiments, a fluid delivery device comprises a fluid dispensing unit which includes a reusable part and a disposable part, and may also include a remote control unit. The reusable part generally contains the relatively expensive components, such as electronics, at least a portion of driving mechanisms (and in some embodiments, all the components of driving mechanisms), sensors, motors and various other components. The disposable part is configured to include a reservoir for retaining therapeutic fluid (e.g., insulin), a connecting tube for delivery of the therapeutic fluid, a piston/ plunger structure (the terms piston and plunger may be used herein interchangeably) for pumping fluid from the reservoir to the body, and, in some embodiments, a power source to provide power to at least one of the reusable part and the disposable part of the fluid delivery device. The disposable part can also be configured to include a portion of the driving mechanism, so that the driving mechanism is being shared by both parts (disposable and reusable).

In some embodiments, the power source can be located in the reusable part. In some embodiments, a power source can be located in both parts. An example of a fluid dispensing unit composed of two parts is described in co-pending/co-owned U.S. patent application Ser. No. 11/397,115 and International Patent Application No. PCT/IL08/001,057, the contents of which are hereby incorporated by references in their entireties. An example of a fluid dispensing unit having a rechargeable power source located in the reusable part is disclosed in co-pending/co-owned International Patent Application No. PCT/IL09/000,266, the content of which is hereby incorporated by reference in its entirety.

The disposable part and/or at least some of its components are generally replaced after a relatively short pre-determined period of time (e.g., after two-three days, one week, or any other suitable time), or after delivery of a pre-determined amount of therapeutic fluid.

In contrast, the reusable part and/or at least some of its components are generally replaced after a longer period of time than the disposable part (and/or its components), for example, after three months, six months or any other suitable time. In some embodiments, any component of the fluid delivery device may be replaced whenever it is malfunctioning.

In some embodiments, a fluid delivery system is provided which, in addition to including a fluid dispensing unit, further comprises a skin securable (e.g., adherable) cradle unit and a remote control unit. The dispensing unit can be connected to and disconnected from the skin securable cradle unit. The remote control unit communicates with the dispensing unit to communicate programming commands and instructions, user inputs, notifications and acquired data.

The fluid delivery system may further include a cannula cartridge unit which comprises a cannula, a penetrating member including a sharp instrument (i.e. needle) to pierce the skin and which is withdrawn after cannula insertion, and a cannula hub. The cannula cartridge unit is configured to be fitted within a "well" of the cradle unit which includes a protrusion that encircles a passageway to facilitate the insertion and placement of the cannula in a subcutaneous compartment of the patient's body and rigidly anchor the cannula hub to cradle. In some embodiments, the cannula can be inserted in various angles with relation to the skin surface. The cannula may be further configured in various lengths to be tailored to a patient's need.

The cradle unit, cannula cartridge unit, and the disposable part of the dispensing unit may be disposable (e.g., may be discarded after 2-3 days). The remote control is generally a durable unit and may be replaced, if necessary, every five years, ten years, or any other relatively long period of time.

In some embodiments, a fluid delivery device/system is provided which comprises a dispensing apparatus for fluid delivery (e.g., insulin) and a sensing apparatus (sensor) to sense body analytes (e.g., glucose). In some embodiments, a subcutaneously insertable element comprises a cannula for fluid delivery and/or a probe for analyte sensing. The subcutaneously insertable element can be used for both dispensing and sensing functionalities. Thus, under such circumstances, the modules/components configured to perform dispensing and sensing operations are implemented using a single device requiring only a single insertion site.

Referring to FIG. 1, a schematic diagram of a fluid delivery system 1000 to perform medical infusion of therapeutic fluid(s) into a body of a patient is shown. The system 1000 includes a dispensing device 10 and a remote control unit 900. Throughout the present disclosure, the terms "dispensing device" and "dispensing unit" are interchangeable and refer to the same structure.

Figure 2A:
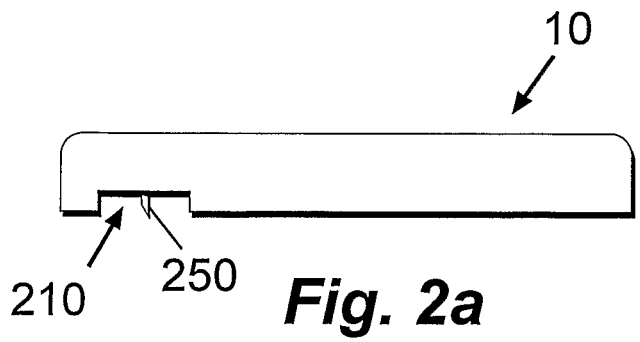
FIGS. 2a-2c are schematic diagrams of a fluid delivery system including a dispensing device that can be composed of one part (2a) or two-parts (2b), and can further include a cradle unit and cannula cartridge unit (2c).
Figure 2B:
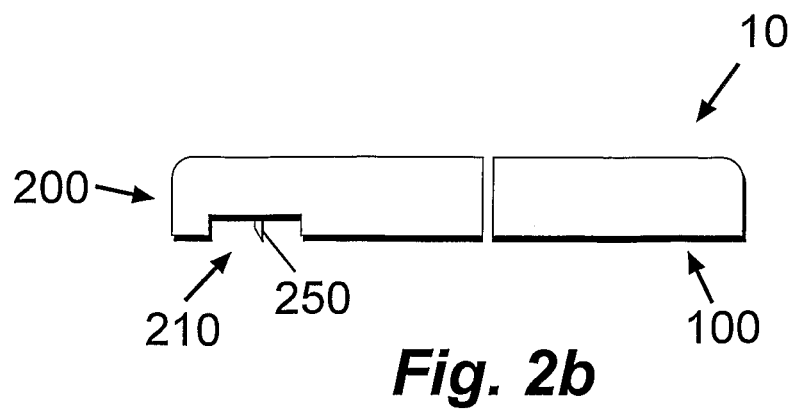
Figure 2C:
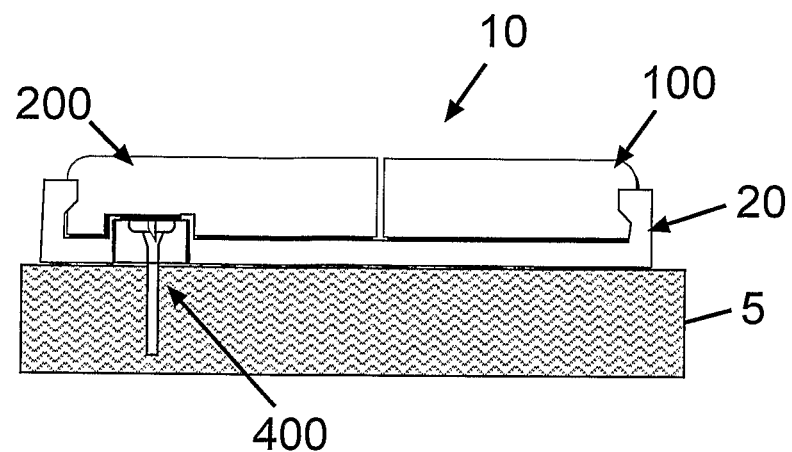

Referring to FIGS. 2a-2c, schematic diagrams of a fluid dispensing device/unit 10 are shown. The fluid dispensing device 10 includes on its bottom surface an outlet port 210 and a connecting lumen 250 configured to enable fluid escape during priming and fluid communication with the patient's body. The dispensing device 10 can be composed of a single part (as shown in FIG. 2a) or of two parts (as shown in FIG. 2b). The two-part dispensing device 10 may include a reusable part 100 and a disposable part 200. In some embodiments, the outlet port 210 and connecting lumen 250 are portions which correspond to the bottom surface of the disposable part 200. The fluid delivery system can further comprise a cradle unit 20 and cannula cartridge unit 400, as illustrated in FIG. 2c. The two-part dispensing device 10 is connected to the cradle unit 20, which, in some embodiments, is skin adherable (the skin is designated in numeral 5). Fluid communication between the dispensing device 10 and the patient's body is enabled through the cannula cartridge unit 400 which is provided with a subcutaneously insertable element (e.g., cannula).

Figure 3A:
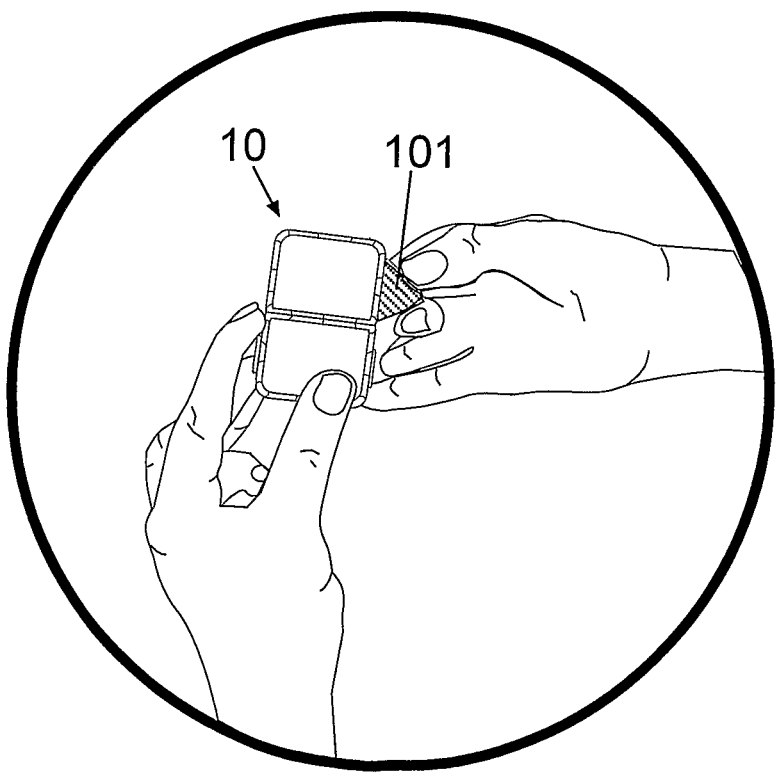
FIGS. 3a-3d are views and diagrams of a fluid dispensing device/unit that can be composed of two parts and can be secured to the skin of a patient.
Figure 3B:
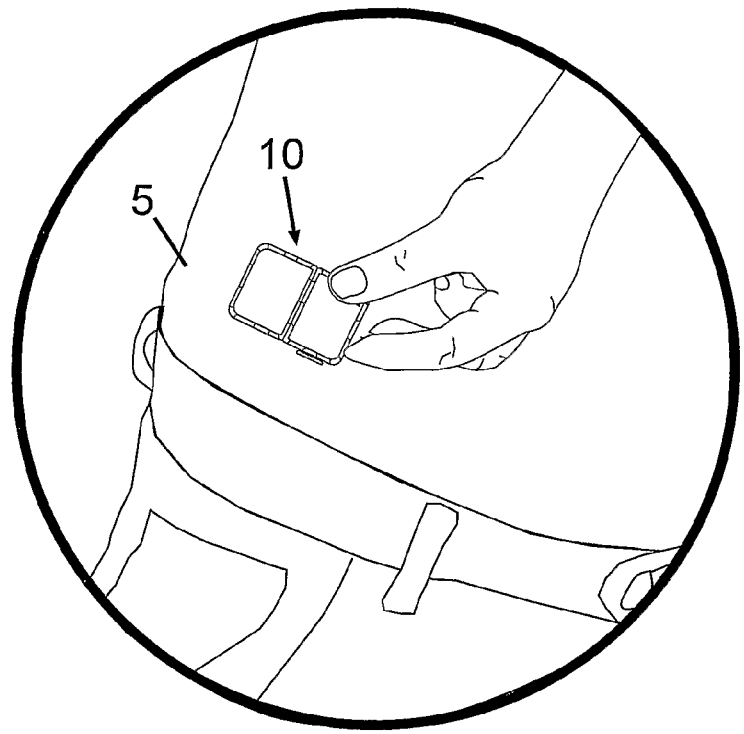
Figure 3C:
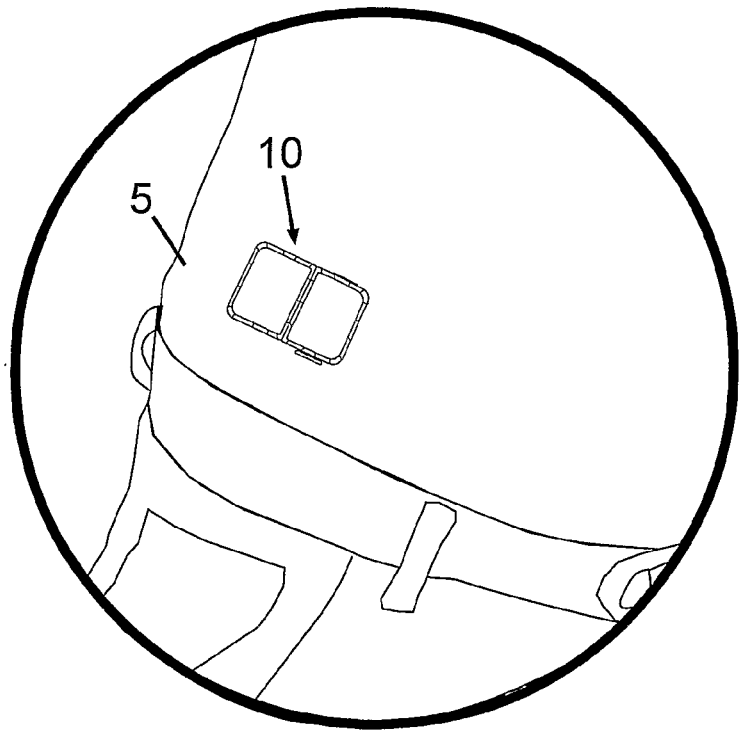
Figure 3D:
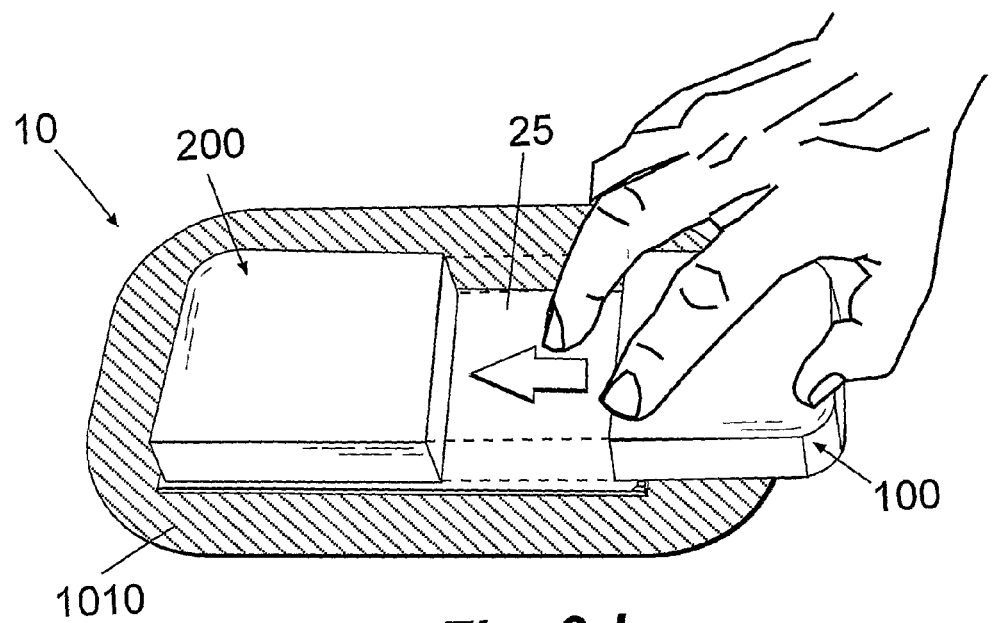

Referring to FIGS. 3a-3d, views and diagrams of a procedure to directly adhere a two part dispensing device/unit 10 to the skin 5 of a patient are shown. FIG. 3a illustrates the removal of a protective cover layer 101 protecting an adhesive layer at the bottom surface of the dispensing device. FIG. 3b depicts the adherence of the dispensing device 10 to the skin 5 FIG. 3c illustrates the operable skin-adhered dispensing unit 10 adhered to the skin of a user/patient. In some embodiments, only the disposable part 200 is securable to the skin 5 FIG. 3d shows an embodiment of a disposable part 200 secured to the skin 5 using adhesive tape 1010 and having an extended base 25. The reusable part 100 can be coupled to the base 25 to mate with the disposable part 200, to enable operation of the dispensing unit 10.

Figure 4A:
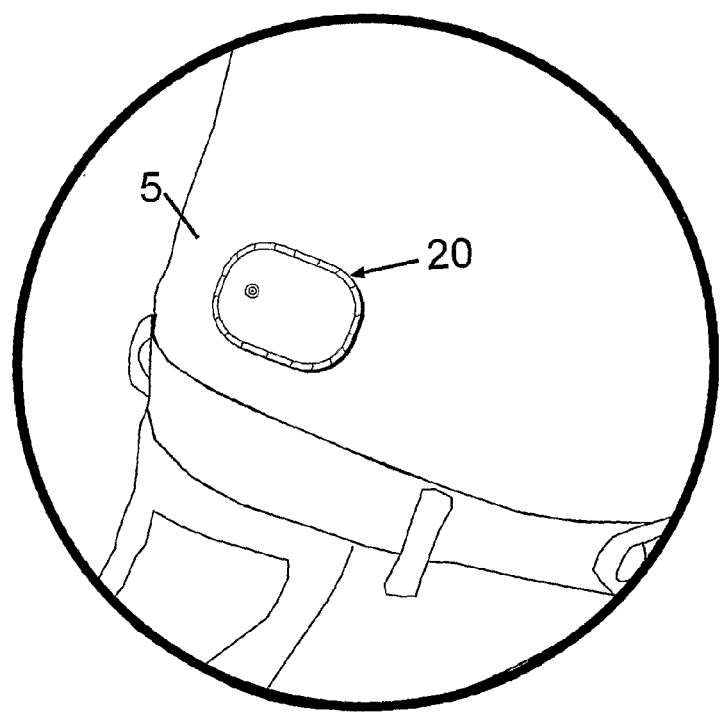
FIGS. 4a-4c are views and diagrams of a skin adherable cradle unit and a dispensing unit connected to the cradle unit.
Figure 4B:
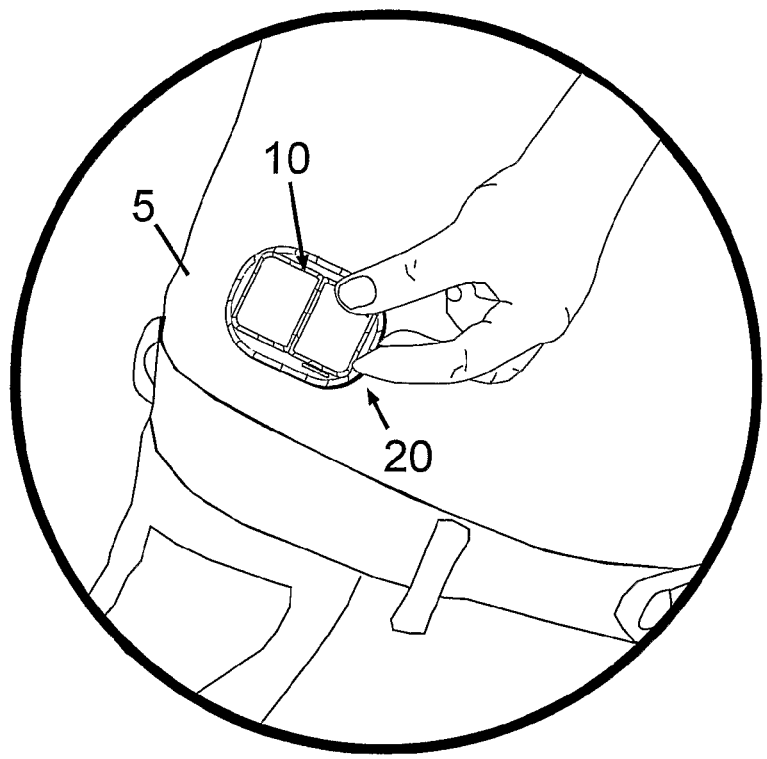
Figure 4C:
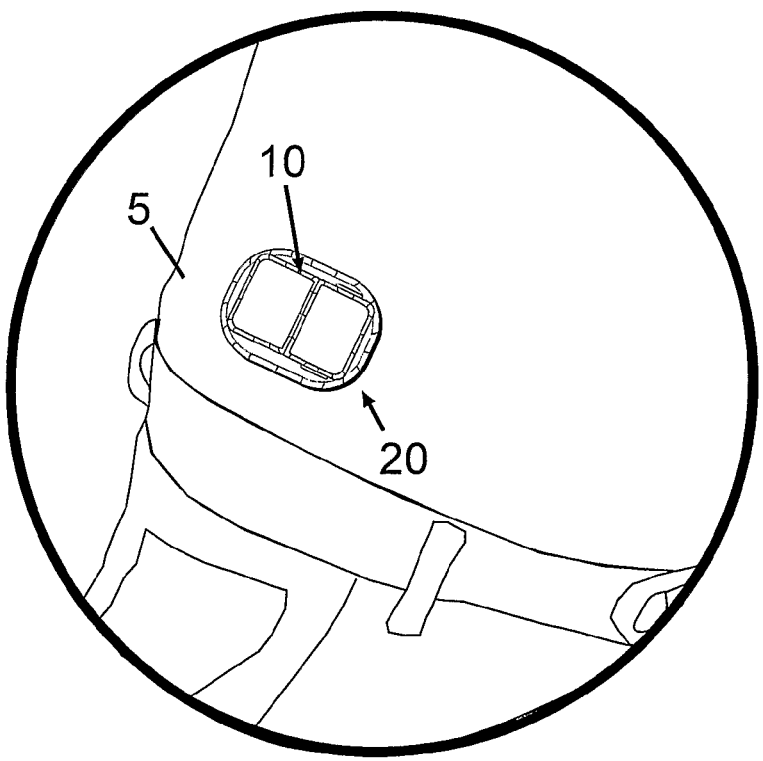

Referring to FIGS. 4a-4c, in some embodiments, a fluid delivery device/system includes a cradle unit 20 that can be adhered to the skin 5. The dispensing device 10 can then be connected to and disconnected from the cradle unit 20 at a patient's discretion. FIG. 4a depicts the cradle unit 20 adhered to the skin 5. FIG. 4b illustrates the connection of the dispensing unit 10 to the cradle unit 20. FIG. 4c illustrates the dispensing unit 10 connected to the cradle unit 20 and ready for operation.

Figure 5A:
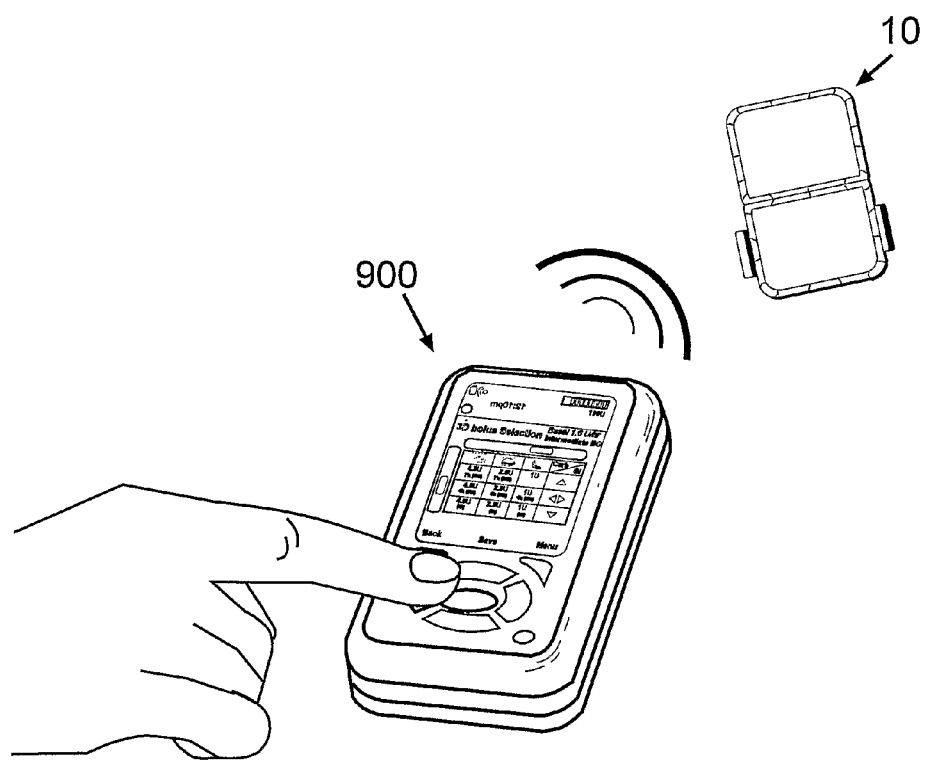
FIGS. 5a-5c are views and diagrams of a fluid dispensing device and facilitating operation of the dispensing device via a remote control unit (5a) and via buttons located on the dispensing device (FIGS. 5b and 5c)
Figure 5B:
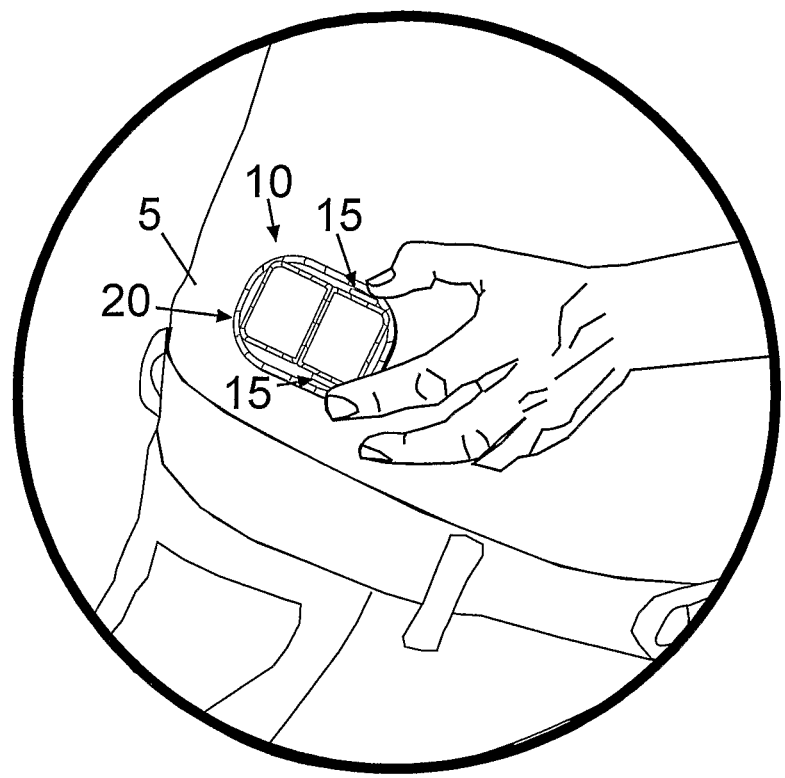
Figure 5C:
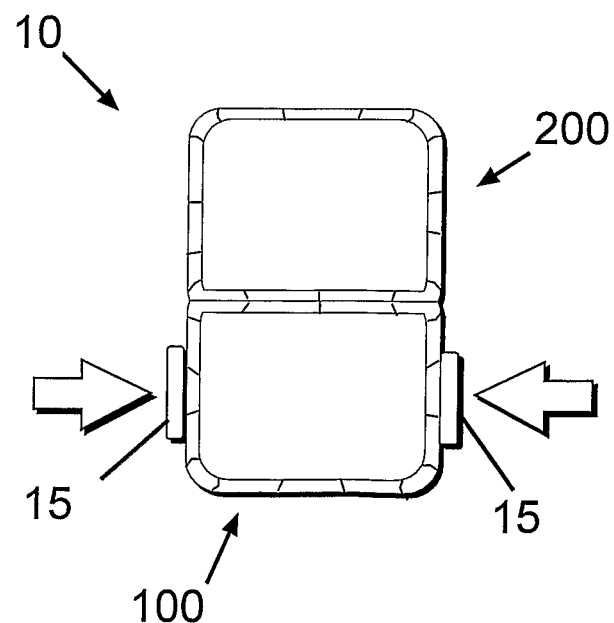

Referring to FIGS. 5a-5c, views and diagrams depicting operation modes of the dispensing unit 10 are shown. The patient can operate the dispensing unit 10 either by a remote control unit 900 (as shown in FIG. 5a) or by one or more buttons 15 located on the dispensing unit 10 (as shown in FIGS. 5b-5c). In some embodiments, operation based on the buttons 15 may be directed for bolus dose delivery.

Figure 6A:
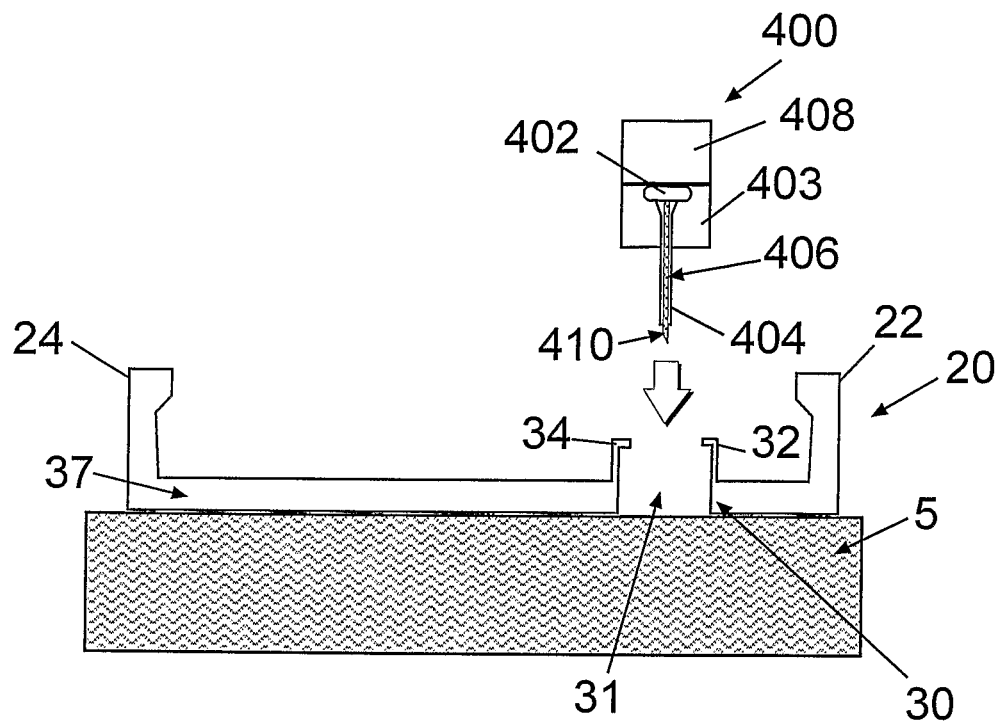
FIGS. 6a-6c are schematic cross-sectional diagrams of an arrangement of a skin adherable cradle unit and cannula cartridge unit and the insertion/placement of the cannula through the cradle and into the body.
Figure 6B:
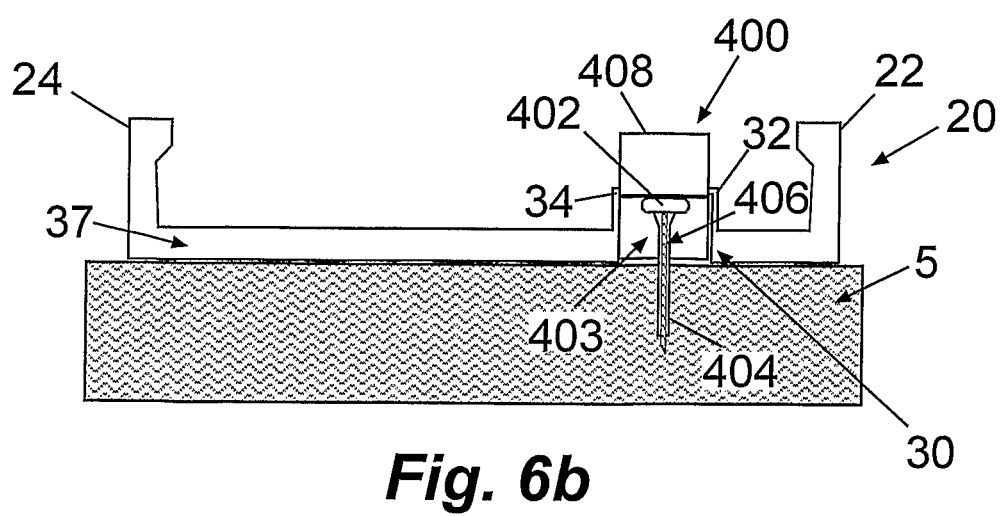
Figure 6C:
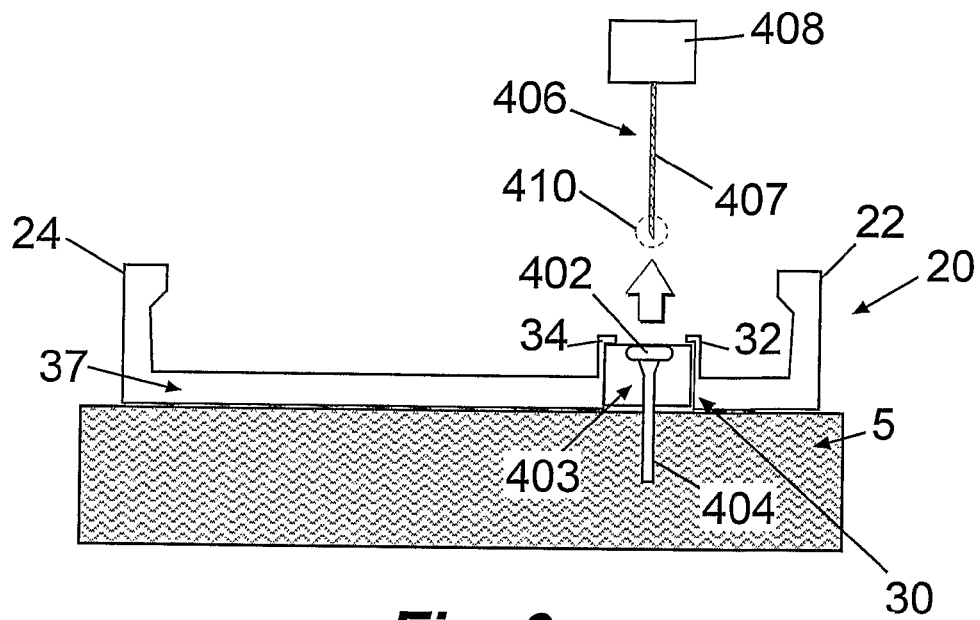

Referring to FIGS. 6a-6c, cross-sectional schematic diagrams depicting operations of the placement of a cannula cartridge unit 400 into the cradle unit 20 and the insertion of the cannula into the patient's body are shown. More particularly, FIG. 6a illustrates a cradle unit 20 which is adhered to the skin 5 and a cannula cartridge unit 400. The cradle unit 20 includes a well 30, a base 37, and latches 22, 24. The cradle unit 20 can be adhered to the skin 5 using an adhesive layer (shown in FIGS. 7a-7b and designated as 26), which may be attached to at least a portion of the bottom surface of the base 37 of the cradle unit 20. The well 30 may be disposed in the cradle base 37 and defines a passageway 31. The passageway 31 enables insertion of a cannula 404 through the cradle 20 into the skin 5. The well 30 may include latches 32 and 34 configured to rigidly connect to a cannula hub 403 once it is placed within the well 30. The latches 22 and 24 are used for securing the dispensing unit 10 to the cradle unit 20 after connection and enabling disconnection and reconnection (as more particularly shown in FIGS. 12a-12c).

The cannula cartridge unit 400 includes a cannula 404 and a penetrating member 406. The cannula 404, configured, in some embodiments, as a soft cannula made of, for example Teflon®, may be adapted to be coupled to an opening of a cannula hub 403 having a self-sealing rubber septum 402 through which the penetrating member 406 is inserted. The penetrating member 406 (as further shown in detail in FIGS. 6c and 8b) includes a sharp tip 410 and a grip 408 and may be configured to penetrate the skin 5 of the patient to allow insertion and placement of the cannula 404 in the subcutaneous tissue (or a body compartment of the patient). The rubber septum 402 may be configured to be repeatedly pierced by the connecting lumen of the dispensing device (i.e., for multiple insertion of the connecting lumen), and is further configured to seal the proximal end of the cannula 404, located in the cannula hub 403 (outside the body), to prevent leakage of therapeutic fluid and/or entry of contaminants once the cannula 404 is inserted and placed in the subcutaneous tissue, as shown in FIG. 6c. The cannula 404 may have various lengths and/or diameters and may be inserted at various angles with regard to the surface of the skin 5 of the patient as described, for example, in co-pending/co-owned U.S. patent application Ser. No. 12/215,255, the content of which is hereby incorporated by reference in its entirety.

FIG. 6b illustrates the cannula cartridge unit 400 after insertion. The cannula hub 403 is placed within the well 30 so that the penetrating member 406 is piercing the skin 5 and the cannula 404 is inserted in the body. The cannula hub 403 is snap-fitted within the well 30 by operation of the latches 32, 34.

FIG. 6c illustrates the cradle unit 20 adhered to the skin 5, with the penetrating member 406 removed. The cannula 404 is placed within the subcutaneous tissue and secured to the cradle unit 20, and a penetrating member 406 which includes a dagger 407 having the sharp tip 410, and the grip 408 is extracted from the cannula cartridge unit 400 to leave the cannula 404 subcutaneously inserted in the body.

Figure 7A:
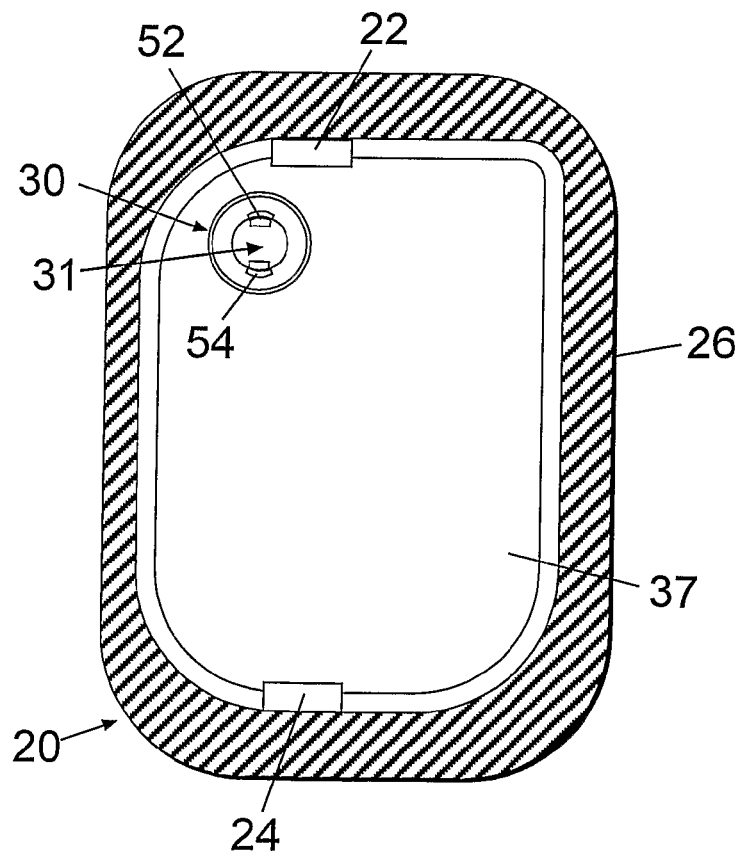
FIGS. 7a-7b are views and diagrams of a skin adherable cradle unit.

Referring to FIGS. 7a-10b, views and diagram depicting a cradle unit, cannula cartridge unit, an inserter, and the procedure of cannula insertion, are shown. In FIGS. 7a-7b, the cradle base 37 comprises, at least in part, an adhesive layer 26 to securely attach the cradle unit 20 to the patient's skin. The adhesive layer 26 may be biocompatible (e.g., constructed from materials that do not cause irritation) and/or comfortable to the patient without disturbing his/her diurnal routine. Before placing the adhesive layer 26 against the skin, a protective peelable cover layer (not shown) may be removed from the adhesive layer.

Figure 7B:
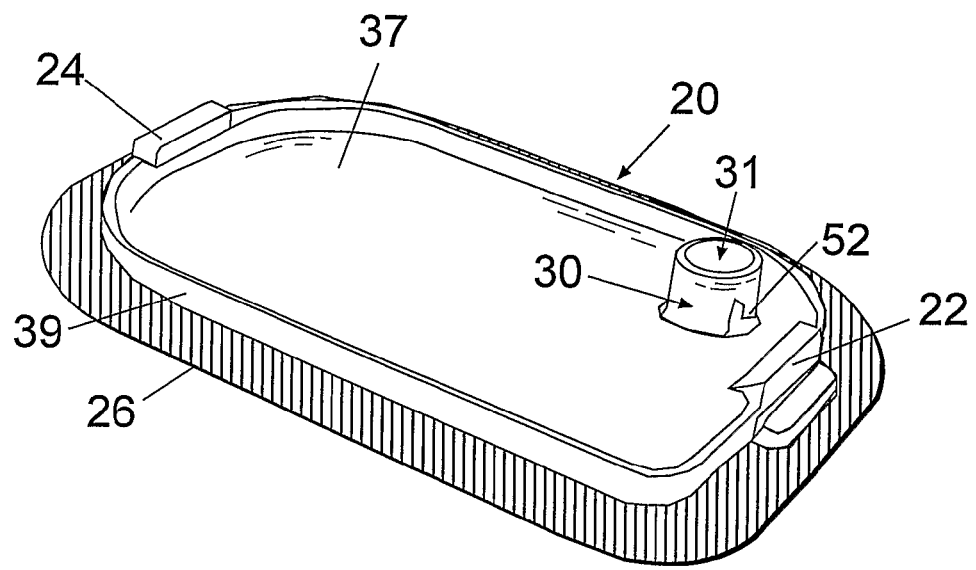

The cradle unit 20 can further include a frame 39 (as shown in FIG. 7b) to support the dispensing unit, and one or more latches 22 and 24 to be received in corresponding complementary grooves/recesses of the dispensing unit (as shown in FIGS. 12a-12e) to enable connection and disconnection of the dispensing device to and from the cradle unit 20. The latches 22 and 24 may be configured as protrusions from the base 37 or the frame 39. The shape of the cradle base may match the dispensing device footprint (as shown) or may have a smaller footprint with one or more latches (e.g., the dispensing device footprint may be 60 mm×40 mm and the cradle base footprint may be 60 mm×20 mm). The well 30 of the cradle unit 20 can further comprise latches 52 and 54 (only one latch 52 is shown in FIG. 7b) to secure the cannula hub 403. Latches 52 and 54 may be configured and operate similarly to the latches 32, 34 described above in relation to FIG. 6a-c.

In some embodiments, the cradle base 37 may comprise apertures/cavities to, for example, improve the adherence/attachment of the cradle unit 20 to the skin 5 surface, prevent moisture confinement between the cradle unit 20 and skin 5, and to enable access to the skin (to relieve any skin irritation by, for example, scratching).

The cradle base 37 can be made of, for example, plastic materials such as polyethylene, polycarbonate or any other suitable material. The material may be, at least in part, transparent to enable the user to see the skin 5 under the base 37 after adherence of the cradle unit 20 to the skin 5. Use of at least partially transparent materials may be important in situations where the cannula 404 has been improperly inserted and locally injured the tissue, for example, when the penetrating member 406 accidentally punctures a blood vessel during cannula 404 insertion, causing hematoma. The user may then remove the cradle unit 20, discard it, and secure another, unused cradle unit, in another insertion site. By discarding only the cradle unit (that is configured to enable connection and disconnection of a dispensing device), a costly discarding of skin adherable insulin pumps (which include the insulin contained therein) may be avoided.

Figure 8A:
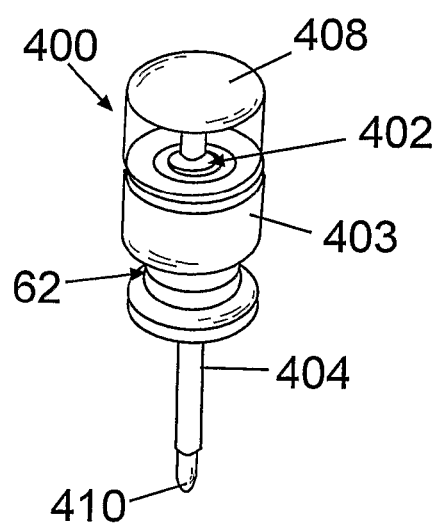
FIGS. 8a-8b are views and diagrams of a cannula cartridge unit.
Figure 8B:
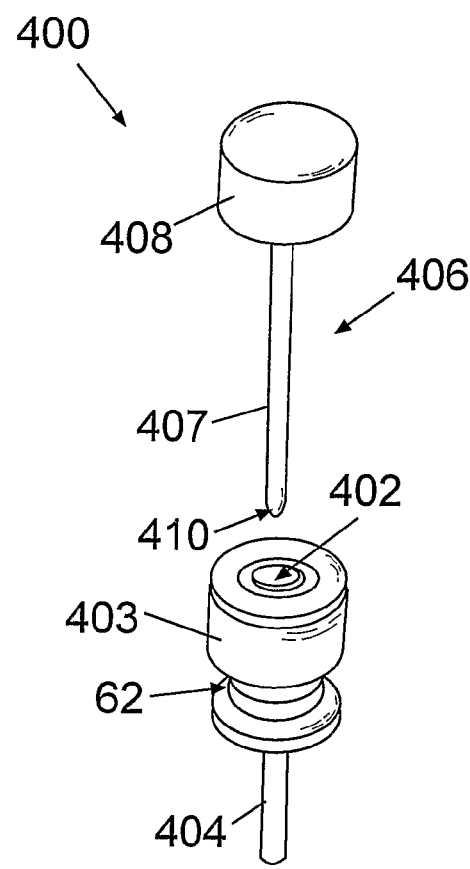

Referring to FIGS. 8a-8b, views and diagrams of a cannula cartridge unit 400 and its components prior to and after placement of a cannula 404 in the body are shown. As illustrated, the cannula hub 403 of the cannula cartridge unit 400 includes a tubular body with an annular groove/recess 62, and is configured to be received as a snap-fit structure within a structurally matching tubular well 30 having latches 52 and 54. A rubber septum 402 (made of, for example, rubber silicon) seals the proximal end of the cannula after the penetrating member 406 has been withdrawn.

Figure 9:
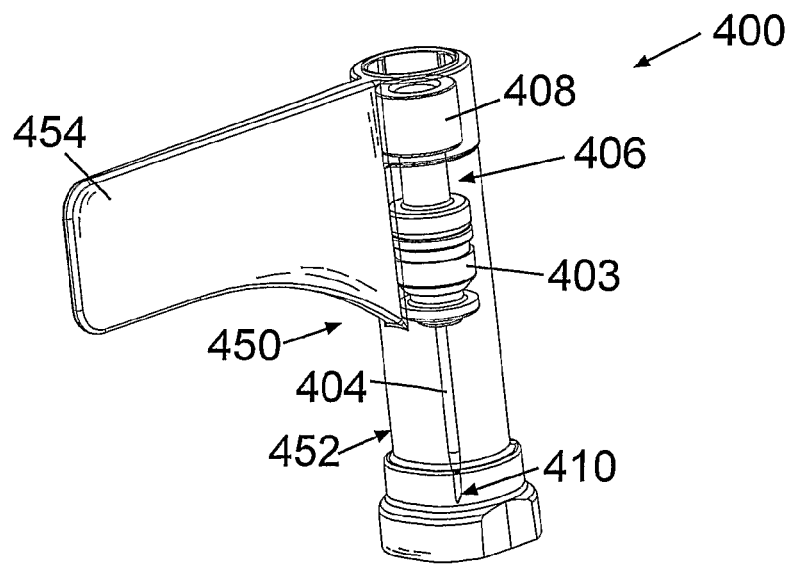
FIG. 9 is a diagram of a cannula cartridge unit with a protector.
Figure 10A:
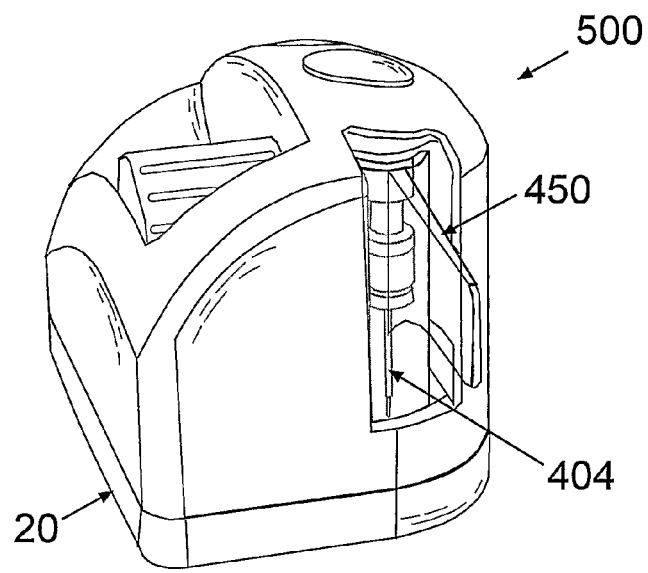
FIGS. 10a-10b are views and diagrams of an insertion device.
Figure 10B:
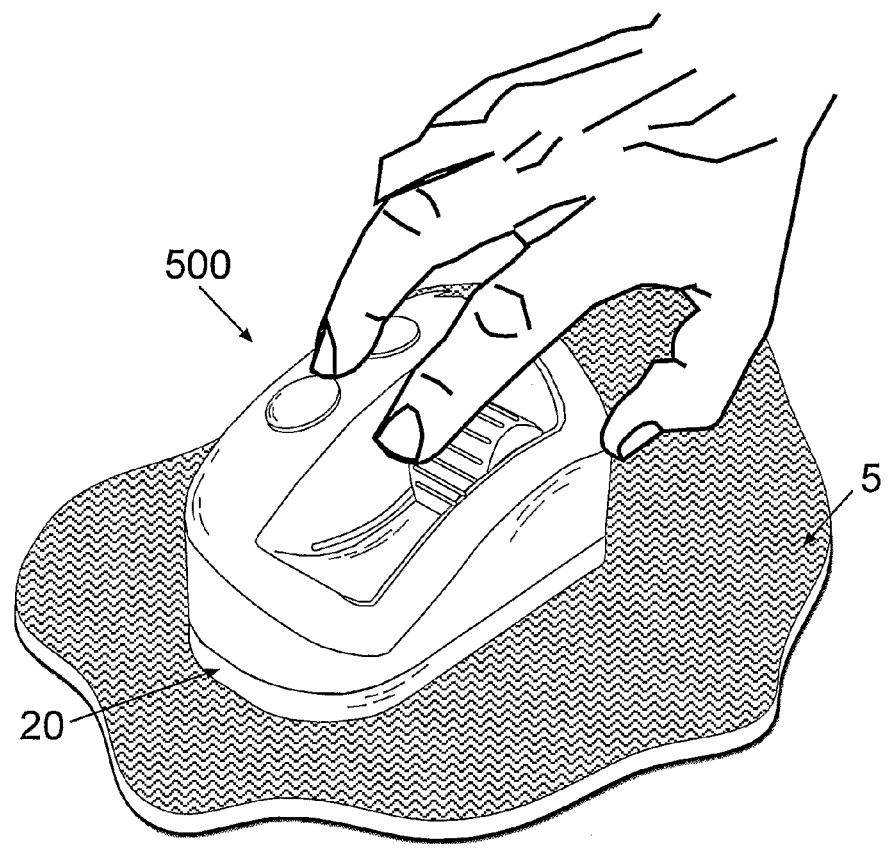

In some embodiments, the cannula cartridge unit 400 further comprises a protector 450, as illustrated in FIG. 9. The protector 450 includes a tubular body 452 to hold the cannula hub 403, the cannula 404 and the penetrating member 406, and a handle 454, extending from the tubular body 452, to enable safe and comfortable handling by a user. The protector 450 is configured to protect the cannula 404 and penetrating member 406 while maintaining sterility of the structure, and prevent accidental piercing of the patient. The protector 450 is further configured to be used with a dedicated insertion device as illustrated in FIGS. 10a-10b. Further details regarding protectors, such as the protector 450, are provided, for example, in co-pending/co-owned U.S. patent application Ser. No. 12/215,219, the content of which is hereby incorporated by reference in its entirety. After the cannula 404 is inserted into the body, the penetrating member 406 with the sharp tip 410 is automatically retracted and remains concealed and shielded within the protector 450. In some embodiments, the cannula 404 can be manually pushed from the protector 450 (e.g., with the aid of a "stick-like" device).

Adherence of the cradle unit 20, insertion of the cannula cartridge unit 400 and subcutaneous placement of the cannula 404 can be performed either manually or by a dedicated insertion device 500, referred-to as "inserter", shown in FIGS. 10a-10b. Both the protector 450 and cradle unit 20 can be loaded into the inserter 500 (see, for example, FIG. 10a). Referring to FIG. 10b, the user places the loaded inserter 500 on a desired location of the skin 5 and operates the inserter 500 to, a) adhere the cradle unit 20 to the skin 5, b) fire downwardly and place the cannula 404 subcutaneously, and c) secure the cannula hub 403 to the well 30 of the cradle unit 20. The penetrating member 406 is then retracted automatically into the protector 450 which can be discarded. Further description of a suitable inserter is provided, for example, in co-pending/co-owned U.S. patent application Ser. No. 12/215,255, the content of which is hereby incorporated by reference in its entirety.

Alleviation of pain and discomfort during skin piercing may be achieved by using pain reduction mechanism (not shown), as described, for example, in co-pending/co-owned International Patent Application No. PCT/IL08/000,861, the content of which is hereby incorporated by reference in its entirety.

Figure 11A:
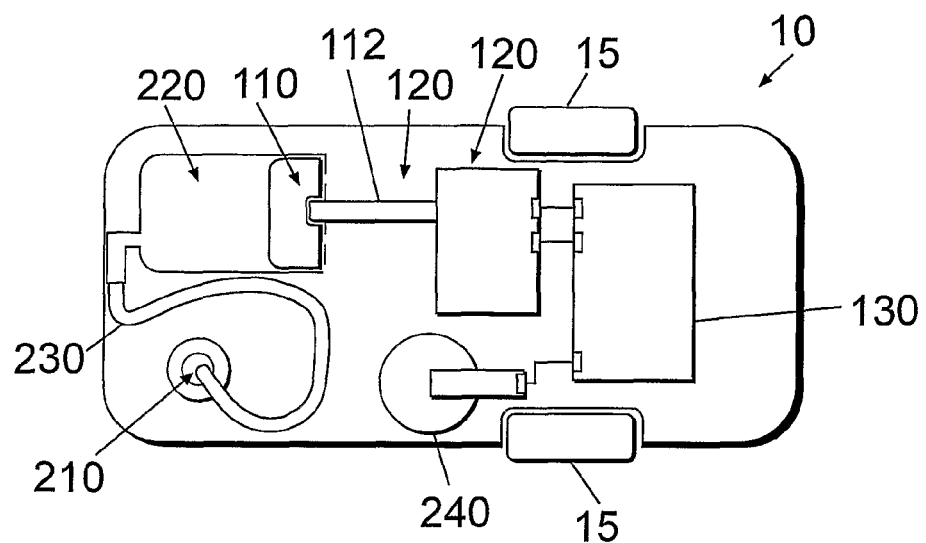
FIGS. 11a-11b are schematic diagrams of a dispensing unit composed of a single part (11a) or two parts (11b), employing a plunger/piston pumping mechanism.
Figure 11B:
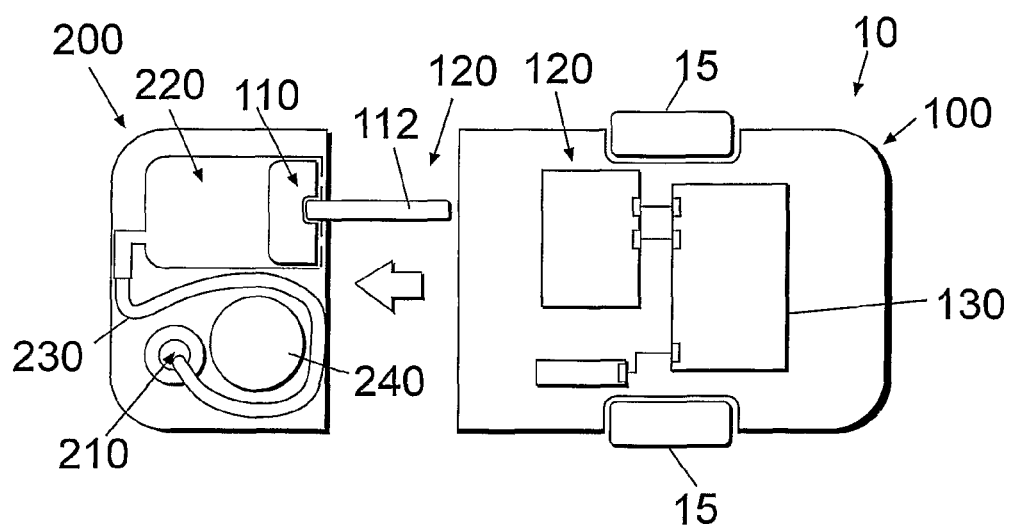

Referring to FIGS. 11a-11b, schematic diagrams of a dispensing device (or unit) 10 which is composed of a single part (as shown in FIG. 11a) and two parts (as shown in FIG. 11b), employing a plunger/piston pumping mechanism to dispense fluid to a patient's body, are shown.

FIG. 11a depicts a single-part dispensing device 10. The fluid is delivered from a reservoir 220 to the outlet port 210. Received within the reservoir 220 is a piston 110 which urges the reservoir's fluid towards the outlet port 210. The reservoir 220 is in fluid communication with the outlet port 210 via a connecting tube 230. Actuation of the piston 110 (and thus displacement of the fluid in the reservoir 220) is performed by a driving mechanism 120 which includes a motor (e.g. a stepper motor, a DC motor, an SMA actuator or the like), and gears for driving the piston 110. The driving mechanism further includes a piston rod 112 which is mechanically coupled to a piston 110. The driving mechanism 120 can be controlled by various electronic modules, including controller/processor (e.g., CPU, MCU) and transceiver, collectively designated using common reference numeral 130. A suitable power source 240 is also provided, and can include one or more batteries, a capacitor to store electrical energy, etc. In some embodiments, the power source 240 may be rechargeable. Infusion programming and control can be performed, for example, by a remote control unit 900 (not shown in FIGS. 11a-11b) and/or by one or more buttons 15 provided on the exterior of the dispensing unit 10.

FIG. 11b illustrates a two-part dispensing device 10 (when the two parts are disconnected) comprising a reusable part 100 and a disposable part 200. The two-part dispensing unit 10 is implemented using a plunger/piston pumping mechanism.

The reusable part 100 may comprise at least a portion of the driving mechanism 120 (e.g., motor and gears), electronic components/modules collectively designated as common reference numeral 130, one or more buttons 15, and may further include other relatively expensive components such as sensors.

The disposable part 200 may comprise the relatively inexpensive components, including, for example, a reservoir 220, provided with a piston 110 which is coupled to a piston rod 112, a power source 240, an outlet port 210, a connecting lumen 250 (not shown in FIGS. 11a-11b) and a connecting tube 230. In some embodiments, the piston rod 112 may be located in the reusable part 100 or be shared by both parts. Similarly, the power source 240 may be located in the reusable part 100 or be included within both parts.

Infusion programming can be performed by a remote control unit 900 (not shown in FIGS. 11a-11b) and/or by one or more buttons 15 provided on the exterior of the reusable part 100. The two-part dispensing unit 10 is operable upon connection of the two parts (100 and 200), as illustrated by the single-headed arrow in FIG. 11b.

Figure 12A:
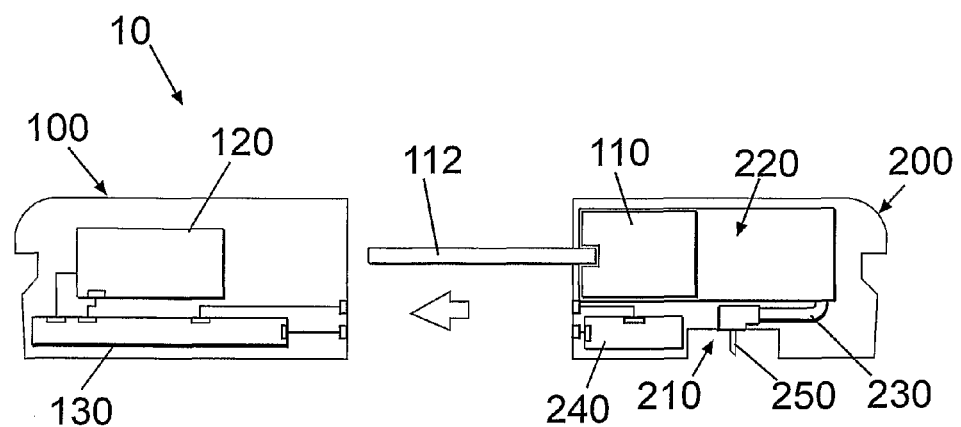
FIGS. 12a-12e are schematic diagrams of a two-part dispensing device (or unit) composed of a reusable part and disposable part, that is connectable to a skin adherable cradle unit.
Figure 12B:
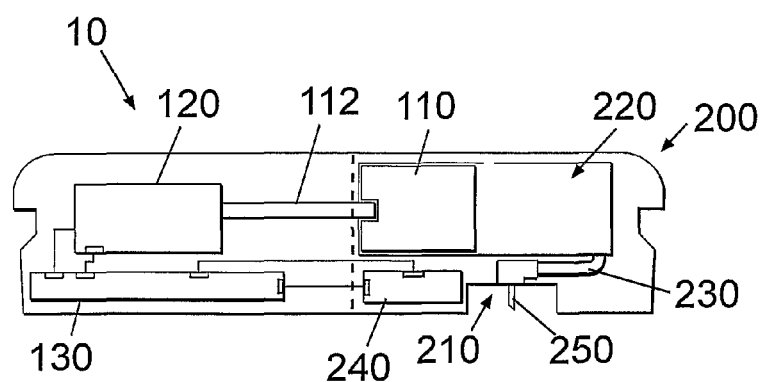
Figure 12C:
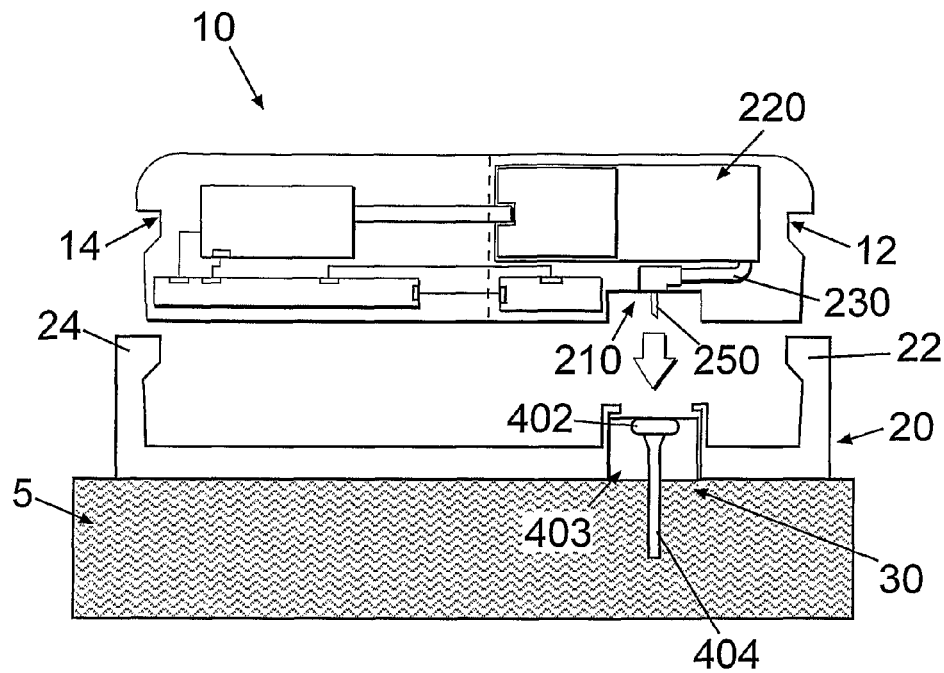
Figure 12D:
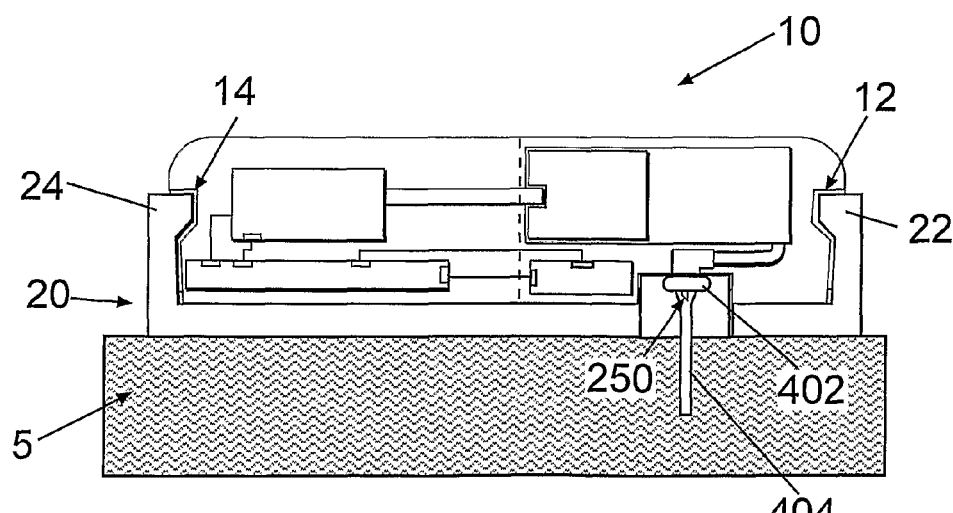

Referring to FIGS. 12a-12e, schematic diagrams depicting connection and disconnection of a two-part dispensing device 10 to and from a cradle unit 20 are shown. FIGS. 12a-b illustrate the dispensing unit 10 composed of two parts, namely, a disposable part 200 and reusable part 100, before connection (as shown in FIG. 12a) and after connection (as shown in FIG. 12b). The dispensing unit 10 may employ a plunger/piston type pumping mechanism which may be operable upon connection of the two parts. FIG. 12c illustrates the dispensing unit 10 (with the reservoir 220 having already been filled with therapeutic fluid) prior to its connection to the cradle unit 20 adhered to the skin 5 of a patient. In FIG. 12c, the cannula hub 403 has been secured to the well 30 of the cradle unit 20 and the cannula 404 has been subcutaneously inserted into the patient. The dispensing unit 10 includes the outlet port 210 having a connecting lumen 250 to pierce the septum 402 upon the connection of the dispensing unit 10 to the cradle unit 20. The connecting lumen 250 enables fluid communication between the reservoir 220 of the dispensing unit 10 and the subcutaneously placed cannula 404. The dispensing unit 10 further includes grooves/recesses 12 and 14 to accommodate complementary-shaped latches 22 and 24, respectively, of the cradle unit 20. The grooves (12 and 14) and latches (22 and 24) implement a snap-fit arrangement which secures the dispensing unit 10 to the cradle unit 20, as shown in FIG. 12d. This connection mechanism thus enables connection/reconnection and disconnection of the dispensing unit 10 to and from the cradle unit 20.

Figure 12E:
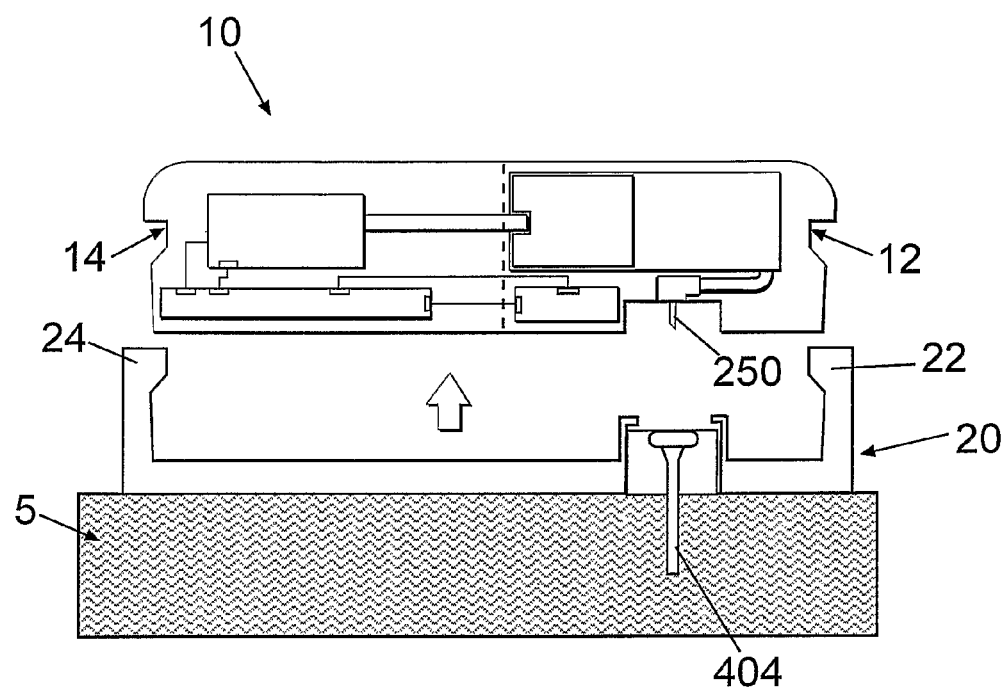

FIG. 12e illustrates the disconnection of the dispensing device 10 from the cradle unit 20. Details regarding various configurations of connection/disconnection mechanisms to connect/disconnect a dispensing unit to a cradle unit are provided, for example, in co-pending/co-owned U.S. patent application Ser. No. 12/004,837 and International Patent Application No. PCT/IL07/001,578, the contents of which are hereby incorporated by reference in their entireties.

Figure 13:
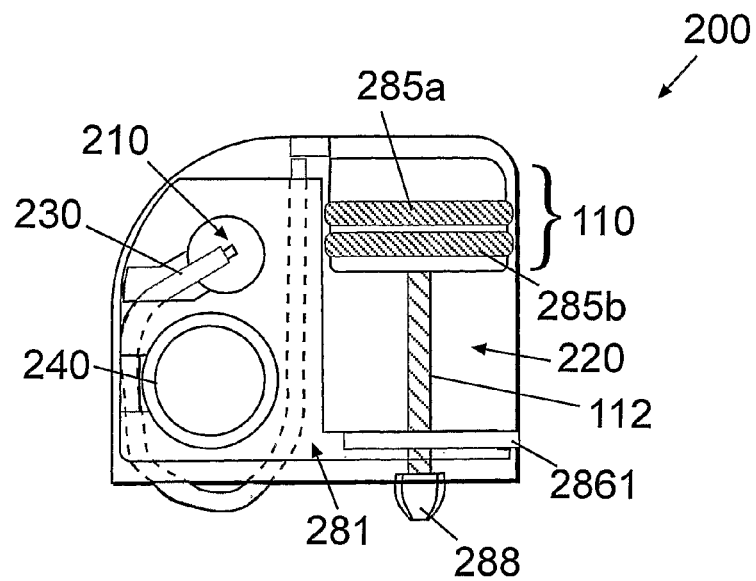
FIG. 13 is a diagram of a disposable part of a two-part dispensing unit.

Referring to FIGS. 13-28c, views and diagrams of a disposable part and its components are shown. FIG. 13 is a schematic diagram of a disposable part 200 having a reservoir 220 adapted with a piston 110. The piston 110 is connected to a threaded piston rod 112 having a tip 288 with teeth (the tip is also referred to as a "juice extractor"). The teeth (or ridges/ribs, or other similarly structured protrusions extending from a central core) create an irregularly-shaped circumferential profile. The piston rod 112 may be gripped at the tip 288 to enable linear displacement of the piston 110 along the interior of the reservoir 220 defined by the reservoir's walls. The piston rod 112 may be substantially entirely contained within the reservoir 220 (e.g., when the reservoir is empty). Under those circumstance, the tip 288 may be extending slightly outside the disposable part 200 to thus enable a patient (or any other user of the device) to grip the tip 288 so as to pull (or push) the piston rod 112 during filling and priming procedures or, alternatively, to enable the patient to connect an auxiliary handle to the tip 288 to facilitate the above-mentioned procedures (as more particularly depicted in relation to FIGS. 25a-26f). Mechanically coupled to the piston rod 112 is an engagement member 2861. The engagement member 2861 may be configured to have two modes/positions that include, a) a disengaged mode/position to enable pushing or pulling of the piston rod 112 during priming or reservoir filling, and b) an engaged mode/position to restrict the displacement of the piston rod 112 during operation. In some embodiments, the piston 110 includes a seal (e.g., two seals/gaskets 285a and 285b, as shown in FIG. 13) to prevent fluid leakage from the reservoir 220 when the piston 110 is being displaced within the reservoir 220.

The disposable part 200 is provided with an outlet port 210 having a connecting lumen 250 (not shown in FIG. 13). The connecting lumen is fluidly coupled to the reservoir 220 through a connecting tube 230 (indicated in gray coloring and dashed lines in FIG. 13). The connecting tube 230 can be supported by and accommodated in a chassis 281).

The disposable part 200 may further include a power source 240 (e.g., a battery) which supplies electrical voltage/current to at least the reusable part (not shown in FIG. 13) when connected with the disposable part 200.

Figure 14A:
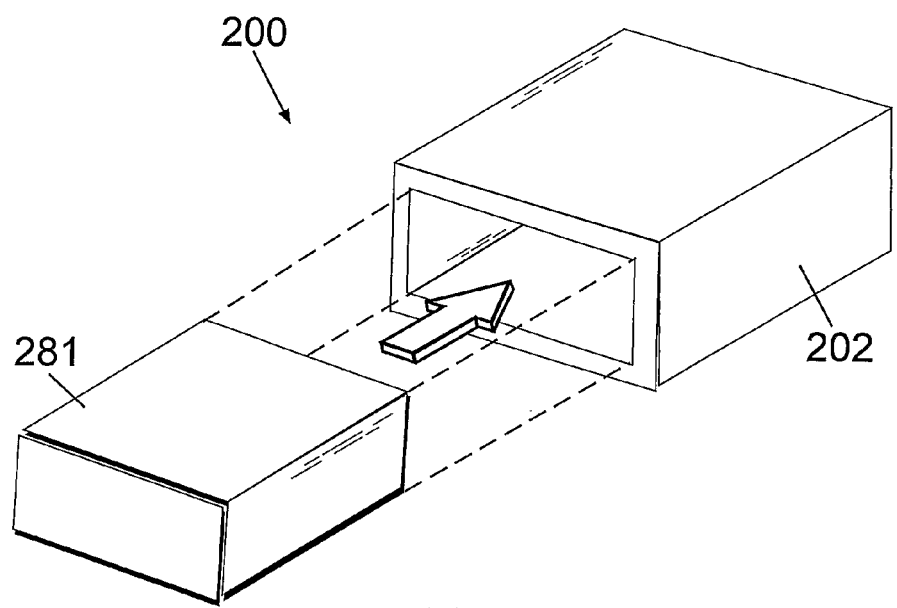
FIGS. 14a-14b are views and diagrams of a disposable part composed of a housing and a chassis.
Figure 14B:
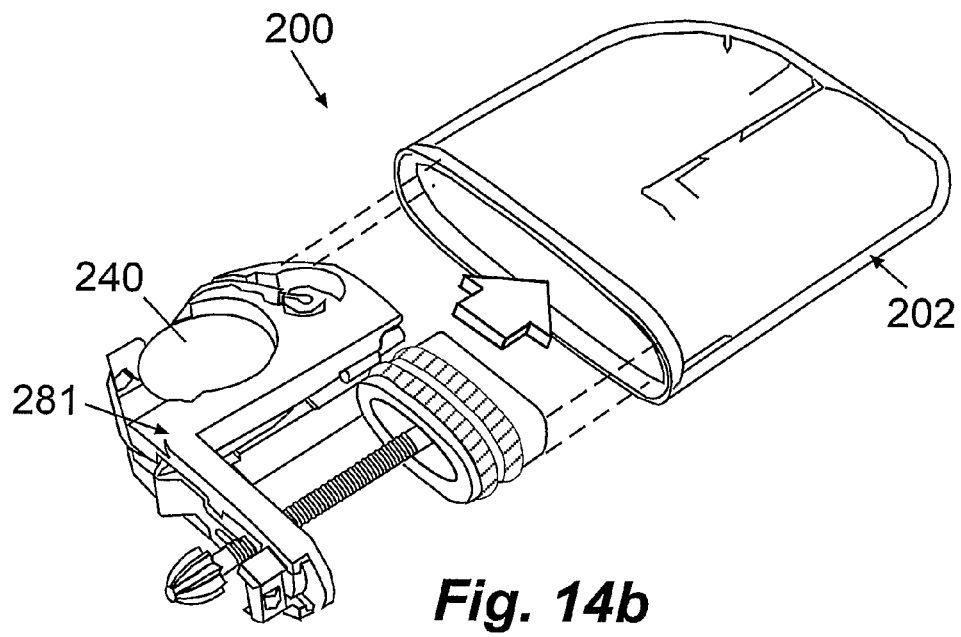

Referring to FIGS. 14a-14b, views and diagrams of a disposable part 200 comprising a disposable chassis 281 and a disposable housing 202 (also referred-to as "disposable pocket") are shown. FIG. 14a illustrates the general concept of having the chassis 281 configured to be received within the housing 202 during manufacturing/assembly process. As shown in FIG. 14b, the chassis 281 is generally configured to have disposable components (e.g., a power source 240) fitted or placed on it, and the housing 202 is configured to cover and protect the chassis 281. In some embodiments, the housing 202 further includes the reservoir, as shown hereinafter.

In some embodiments, the disposable chassis is assembled as a module ready for easy and convenient assembly with the disposable housing by inserting the chassis into the housing. The easy assembly approach may be used with either one or both of the disposable housing and its housed components and the reusable housing its housed components.

Figure 15A:
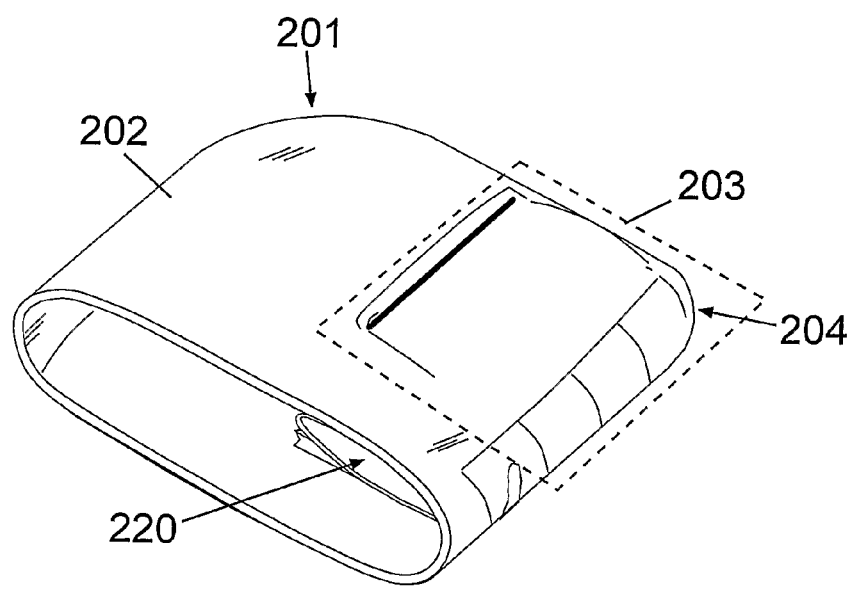
FIGS. 15a-15c are views and diagrams of a housing of a disposable part.
Figure 15B:
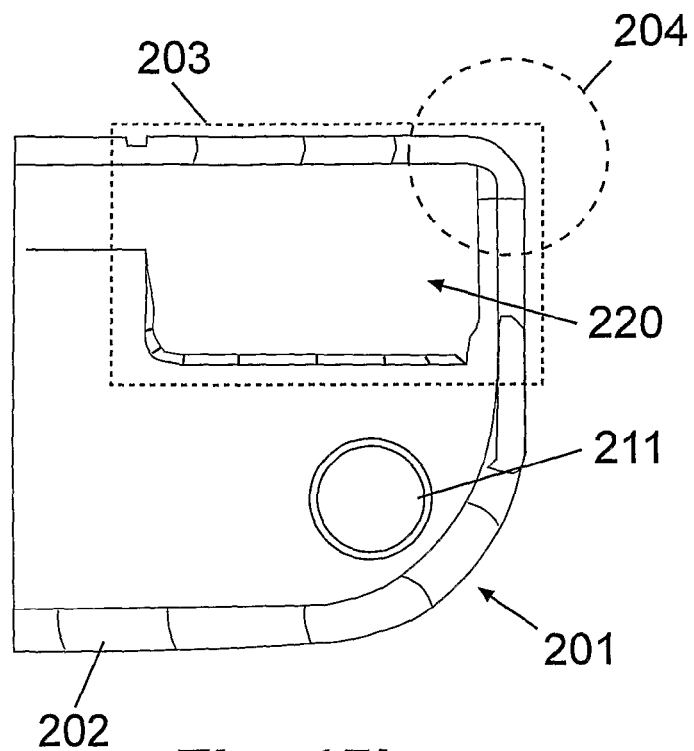
Figure 15C:
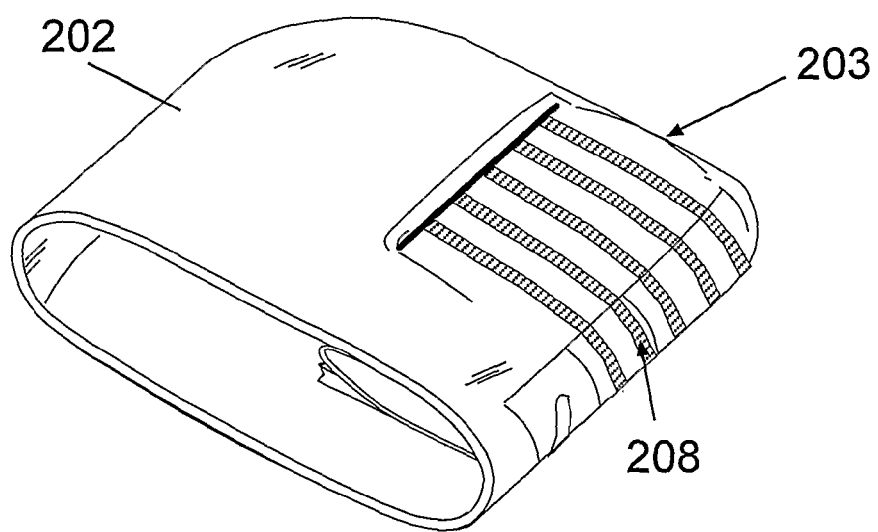

Referring to FIGS. 15a-15c, views and diagrams illustrating a reservoir 220 of a disposable part are shown. The reservoir 220 includes a recessed portion 203 of the housing 202, which may have an oval-shaped section that encompasses all or at least a portion of the reservoir 220. This section may be an integral part of the structure of the housing 202. Thus, in such embodiments, the walls of the housing define the recess constituting the reservoir. The recessed portion 203 may be structured to receive a piston 110 (not shown in FIGS. 15a-15c) having a complementary matching structure (which can be oval, elliptical, round, multi-contoured, or any other shape as shown for example in FIGS. 16a-19b) to the shape of the recess. The interior of the reservoir 220 may be lubricated or include an oily layer to reduce friction between the piston and the walls of the reservoir 220 and/or to enable smooth and unhindered displacement of the piston within the reservoir 220.

The perimeter of the housing 202 may be asymmetrical and have two corners (204 and 201) and may include different curvatures. For example, the corner 204 may have an approximated sharper angle at the side of the reservoir 220, and the corner 201 may have a curve defining a smaller angle on its other side. Such an arrangement enables optimization of the volume of the reservoir 220 and the fitting of a piston within it. At least a portion of the reservoir may include one or more reinforcing ribs, which may be integral with the housing 202, but which may also be supplied as a separate reinforcing structure either within the reservoir 220 or external thereto. Such an embodiment is illustrated in FIG. 15c.

With reference again to FIG. 15b, showing a bottom view of the housing 202, the housing 202 includes a circular opening 211 to receive the outlet port upon connection of the housing 202 and chassis 281 (not shown in FIGS. 15a-15c).

In some embodiments, the housing 202 may include a supporting structure to protect the recessed portion 203 of the housing 202 from external pressure that might cause undesired and uncontrolled fluid delivery to the patient's body, as shown in FIG. 15c. The housing 202 includes supporting crossbeams 208 which define a rigid structure to protect the recessed portion 203 from an external undesired pressure. The crossbeams 208 can also be integral with the housing 202.

In some embodiments, the housing 202 is constructed from plastic material such as polyethylene, and may be, at least partly, transparent (see FIGS. 28a-28c) to thus enable a user to view the therapeutic fluid retained within the reservoir 220 and to, for example, identify air bubbles in the reservoir during the filling/priming processes. Moreover, the entire housing 202 of the disposable part 200, as well as one or more of its non-moving components, may be constructed as an injection molded integral housing unit made substantially from the same material.

In some embodiments, the cross-section of the disposable part 200 may define a multi-curve shape. Such curved structures, when used to in defining the structure of the reservoir section within the housing, improve sealing and/or overall operability of the piston pump. Such curved sections create a rigid structure that provides adequate support and protection to the components disposed inside the disposable part 200. Such a curved structure is illustrated in FIGS. 16a-19b. Accordingly, the reservoir's 220 cross-section may define a closed curve-based geometry, e.g., a circle, an ellipse, an oval, a combination of severally connected curves defining a closed geometry (e.g., 4-curves, 8-curves), or the like. Structures of disposable parts are also described, for example, in co-pending/co-owned International Patent Application No. PCT/IL08/000,641, the content of which is hereby incorporated by reference in its entirety. Other cross-sections shapes/structures may also be used.

Figure 16A:
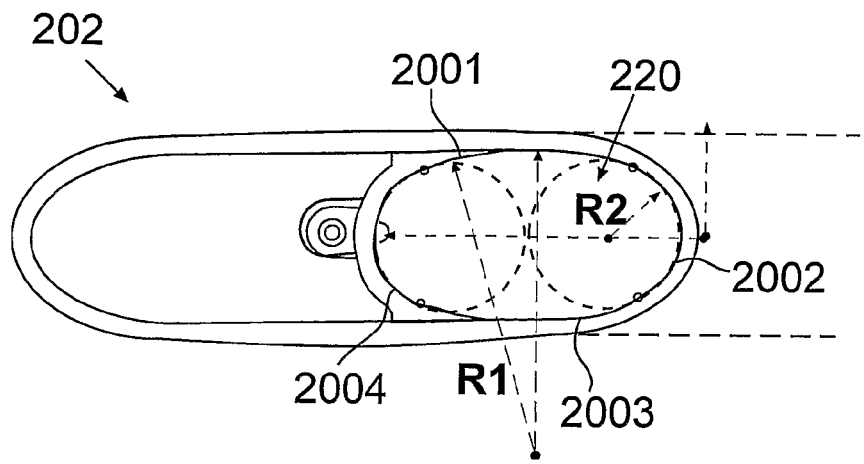
FIGS. 16a-16b are diagrams of a four (4) curves shaped reservoir.
Figure 16B:
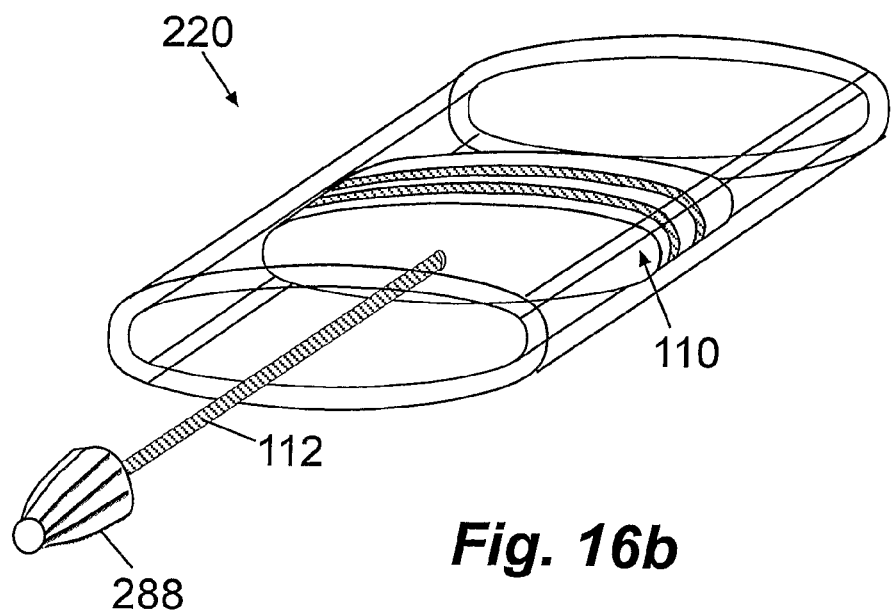

Specifically, in some embodiments, the reservoir 220 may have a cross section defined by a four-curved geometry, as shown in FIGS. 16a-16b. FIG. 16a is a cross-sectional view of a housing 202 of the disposable part 200 that includes an integrally connected four-curved reservoir 220. Each of any two opposite curves have substantially the same curvature radius, e.g., curves 2001 and 2003 have a curvature radius R1 and curves 2002, 2004 have a curvature radius R2. The joint (osculation) of two adjacent curves is smooth. In some embodiments, a cross section can be defined analogously by eight curved shapes/arcs (not shown) having four different radii with the joint of each two adjacent curves being smooth. FIG. 16b is a perspective view of a reservoir 220 defined by a four-curved geometry and provided with a piston 110 having a complementary matching structure that is displaceable within the reservoir 220.

Figure 17A:
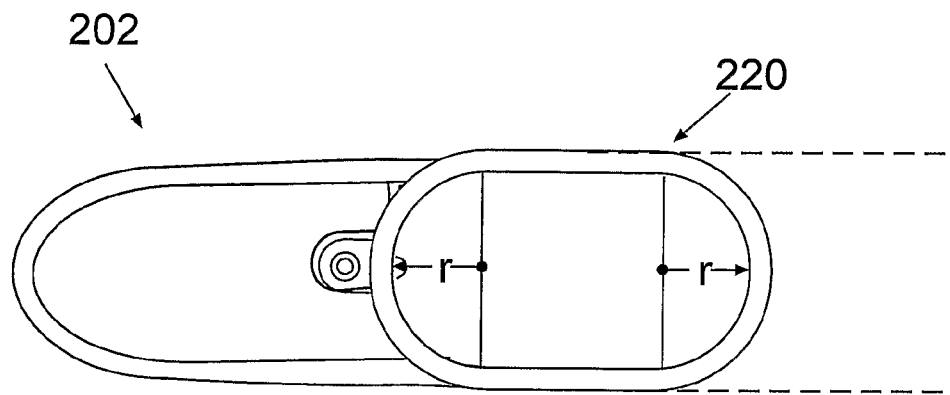
FIGS. 17a-17b are diagrams of an oval-like shaped reservoir.
Figure 17B:
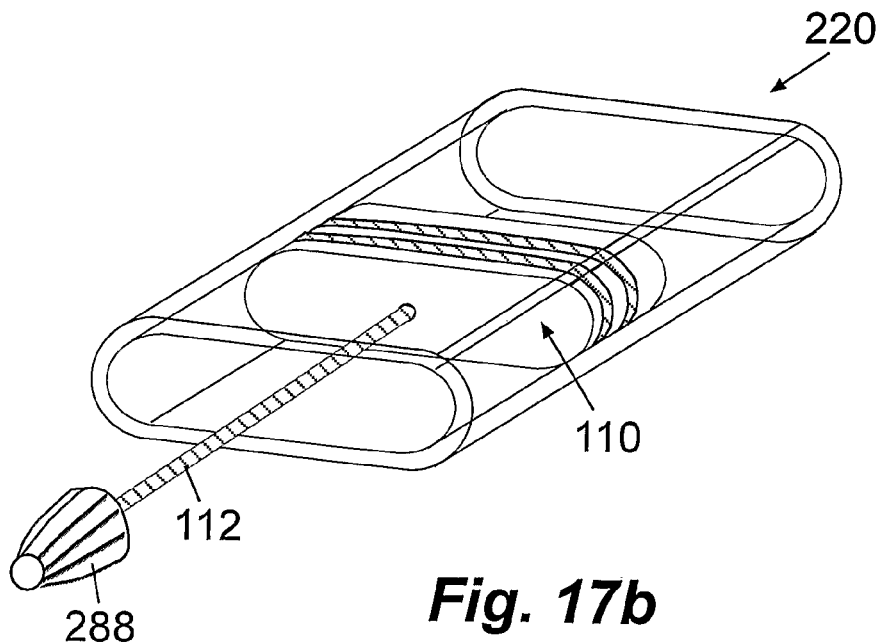

In some embodiments, the reservoir 220 has either oval-shaped, ellipse-shaped or multi-curved cross section. FIG. 17a shows a cross-sectional view of a housing 202 of the disposable part 200 that includes an integrally connected reservoir 220 having an oval-shaped cross section. The depicted reservoir 220 has a generally approximate rectangular cross section with circular side portions. FIG. 17b is a perspective view of a reservoir 220 having an oval-shaped cross section. Received within the inner volume defined by the reservoir 220 is a displaceable piston 110 having a complementary matching structure.

Figure 18A:
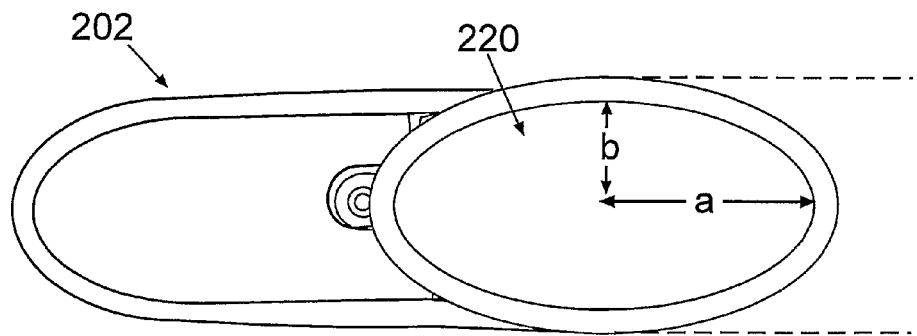
FIGS. 18a-18b are diagrams of an elliptic shaped reservoir.
Figure 18B:
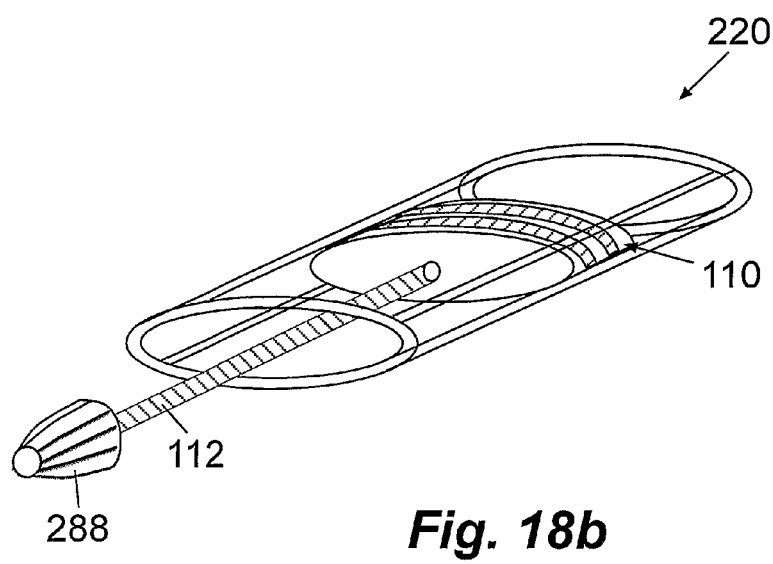

Referring to FIG. 18*a*, a cross-sectional view of a housing 202 of the disposable part 200 that includes an integrally connected reservoir 220 having an elliptical cross-sectional geometry is shown. FIG. 18*b* is a perspective view of a reservoir 220 having an elliptical cross section, provided with a displaceable piston 110 that can be actuated to move in the inner volume of the reservoir 220.

In some embodiments, a dispensing device 10 fitted with such multi-curved, oval or elliptical reservoirs will generally have a thin profile, to thus provide a patient with a miniature, comfortable and discreet pump. Such thin profiles have, in some embodiments, thicknesses of less than 12 mm.

Figure 19A:
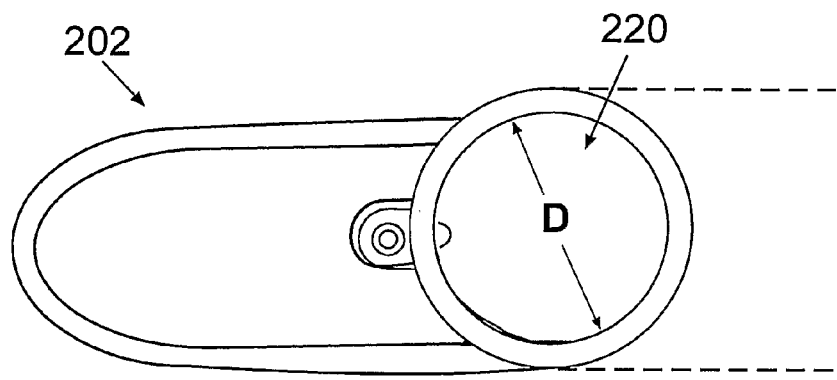
FIGS. 19a-19b are diagrams of a round shaped reservoir.
Figure 19B:
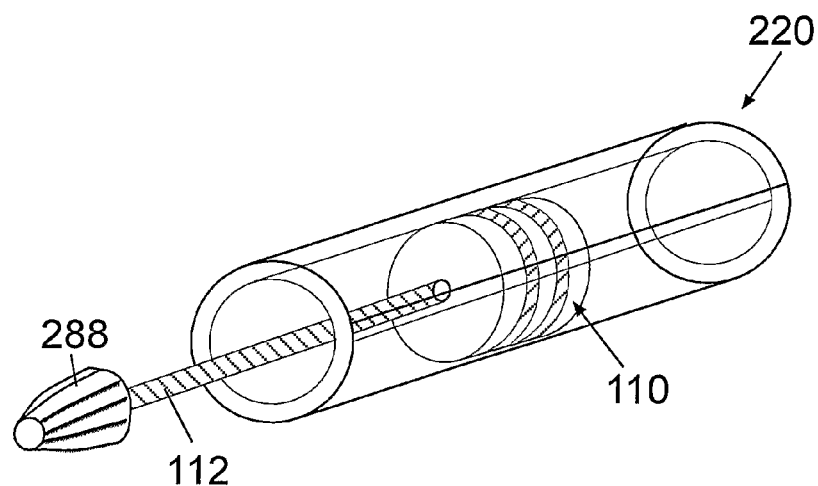

Referring to FIG. 19*a*, a cross-sectional view of a housing 202 of the disposable part 200 that includes an integrally connected reservoir 220 having a substantially round-shaped (circular) cross-sectional geometry is shown. FIG. 19*b* is a perspective view of a reservoir 220 having a round-shaped cross section with a displaceable piston 110 disposed therein.

FIGS. 16*a*-19*b* show some examples of reservoir/housing/piston arrangements. In some embodiments, the dispensing unit 10 may employ one or more reservoirs 220, configured in various shapes, designs and dimensions.

Figure 20A:
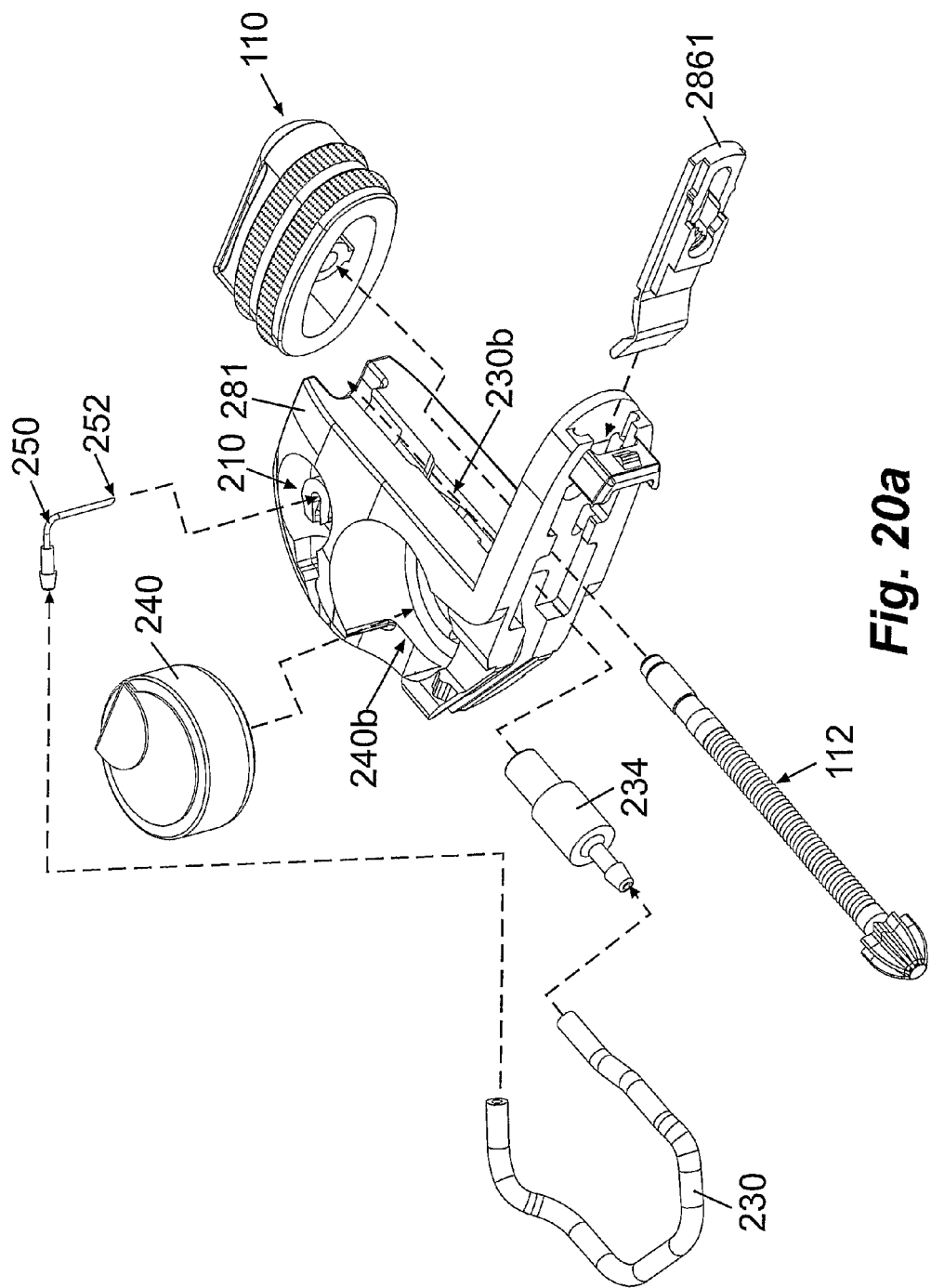
FIGS. 20a-20d are views of a disposable part, including an exploded view of a disposable part chassis and disposable components (20a) and the disposable part housing (20b) with views (20c-20d) that depict the fluid flow path.

Referring to FIGS. 20*a*-20*d*, views and diagrams of a disposable part and its components, including the disposable chassis 281, are shown. FIG. 20*a* is an exploded view of the chassis 281 and the disposable components of the disposable part 200. An engagement member 2861 is received within the chassis 281. A piston rod 112 passes though a hole defined in the engagement member 2861 and is coupled to the piston 110. At least one button battery, identified by numeral 240, is received within a recess 240*b* defined in the chassis 281. The fluid path includes a bent connecting lumen 250 (e.g., a lumen made of stainless steel and/or other suitable material), with a sharpened end 252. The connecting lumen 250 is disposed in the outlet port 210, with one end of the connecting lumen 250 being connected to the connecting tube 230 which is retained, in some embodiments, in a dedicated track 230*b* (which may have a variable cross-section) of the chassis 281. The connecting tube 230 may be further attached to a tube nipple 234 configured to enable fluid communication with the reservoir 220 defined in the housing 202.

Figure 20B:
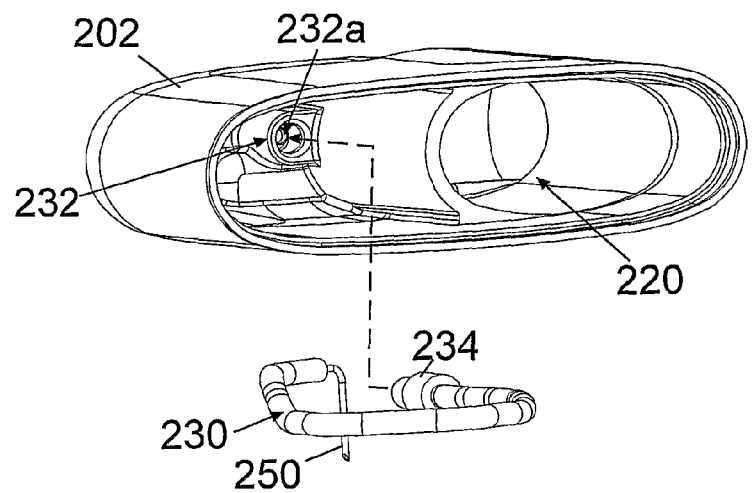
Figure 20C:
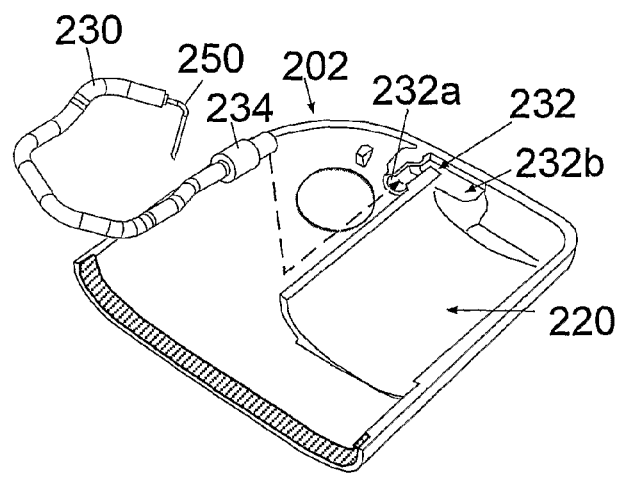
Figure 20D:
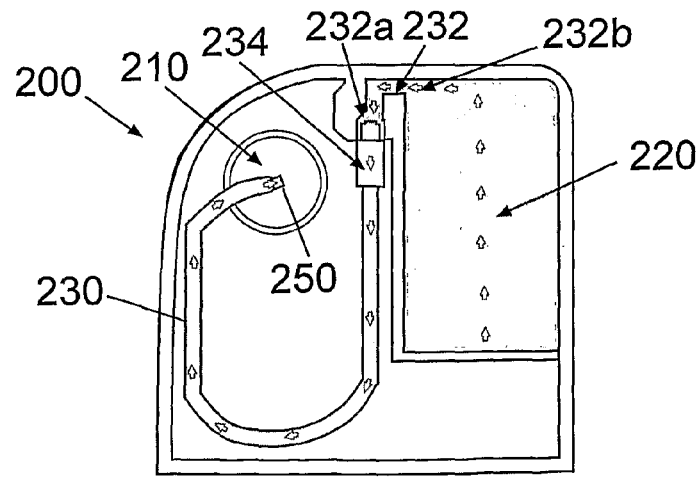

FIG. 20*b* depicts the connection of the tube nipple 234 with the opening of a fluid channel/tunnel 232 disposed inside the walls of the housing 202. The channel 232 may be provided with two openings: one opening 232*a* to connect with the tube nipple 234 and another opening 232*b* (not shown in FIG. 20*b*) leading into the reservoir 220. Thus, fluid can flow from the reservoir 220, through the channel 232 to the connecting tube 230 and towards the connecting lumen 250. Fluid flow in an opposite direction is also possible, e.g. during filling of the reservoir. FIG. 20*c* illustrates an isometric view of part of the disposable housing 202. The tube nipple 234 is connectable to the opening 234*a* of the fluid channel 232. This connection is indicated by the dashed arrow. FIG. 20*d* shows an upper view of the disposable part 200. The fluid (indicated in gray coloring) can flow from the reservoir 220 to the fluid channel 232 through the opening 232*b*. The fluid can then flow from the fluid channel 232 to the tube nipple 234 connected to the opening 232*a*. From the tube nipple 234, the fluid continues to flow to the connecting lumen 250 through the connecting tube 230. An opposite direction of fluid flow is allowed during reservoir filling. In some embodiments, the disposable part 200 may be configured to have a direct fluid communication between the reservoir and connecting lumen, i.e. without the connecting tube.

Referring to FIGS. 21*a*-21*c*, views and diagrams of a piston 110 are shown. FIG. 21*a* depicts the piston 110 configured to be received and operate with a reservoir 220. The illustrated piston 110 has a curved shape (4-curves) which matches a 4-curved cross-sectional inner structure of the reservoir 220. The piston 110 includes two peripheral grooves 185*a* and 185*b* placed on the exterior of the piston 110 that are configured to receive seals/gaskets 285*a* and 285*b*, respectively. The seals/gaskets 285*a* and 285*b*, such as rubber 0-rings, may prevent undesired fluid leakage from the reservoir 220 and/or stabilize the piston 110 within the reservoir 220. It is to be noted that in some embodiments, a single seal/gasket may be used, or that more than two seals/gaskets may be used. In some embodiments, the seals/gaskets may be lubricated, or include an oily layer (e.g., oily silicate coating), to reduce friction with the walls of the reservoir 220 and/or to enable smooth and unhindered displacement of the piston 110 within the reservoir 220. FIG. 21*b* illustrates the piston 110 with the two seals/gaskets 285*a* and 285*b* fitted within the piston's grooves 185*a* and 185*b*. The piston 110 includes an opening 192 configured to receive the piston rod 112, and to thus establish a mechanical connection between the piston 110 and the piston rod 112 (shown in greater detail in FIGS. 23*a*-23*b*). FIG. 21*c* illustrates the piston 110 without the seals/gaskets 285*a* and 285*b*. The piston includes a nose section 114 which is the piston's surface that comes in contact with the fluid in the reservoir 220. The profile of the nose section 114 is partially flattened and configured to optimally fit with the interior walls of the reservoir so that it facilitates, a) reducing the waste of any residual therapeutic fluid left in the reservoir as fluid is being directed to and deliver by the connecting tube to the patient's body, and b) preventing the occurrence of undesired air bubbles in the reservoir during filling/priming. The nose section 114 further includes a depression 116 configured to fit a complementary bulge (not shown) provided in the interior of the housing 202. The bulge is part of the recess configured to receive the latch of the cradle unit.

Figure 22:
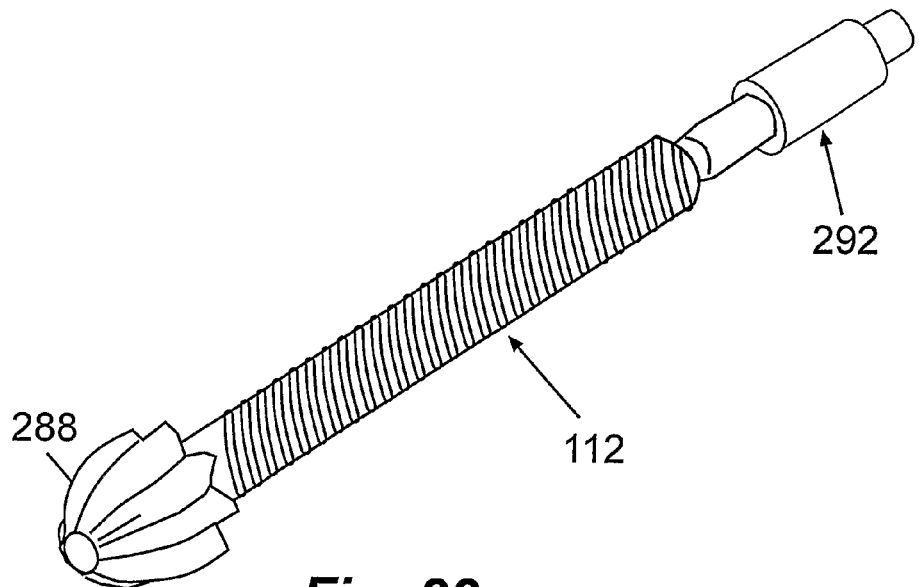
FIG. 22 is a perspective view of a piston rod.

Referring to FIG. 22, a perspective view of a threaded piston rod 112 having a driving tip 288 with protruding teeth on its proximal end, and a smooth distal end 292 with an undercut, is shown. The tip 288 is configured to interact with the portion of the driving mechanism (e.g., the "sleeve"), located in the reusable part 100 upon connection of the reusable part and disposable part, to transfer rotational power to cause a linear translational motion of the piston 110, as described herein. In some embodiments, the piston rod 112 and the tip 288 are manufactured as a single component. In some embodiments, the driving tip 288 is manufactured as a member separate from the piston rod 112, and may be assembled onto the proximal end of the piston rod 112 (e.g., glued, welded, screwed-in, etc.) during assembly of the disposable part. Alternatively, injection molding, for example, may be used to form together a single inseparable item. The term "piston rod" may refer hereinafter to the piston rod including the tip. The distal end 292 of the piston rod 112 is mechanically coupled to the piston 110.

Figure 23A:
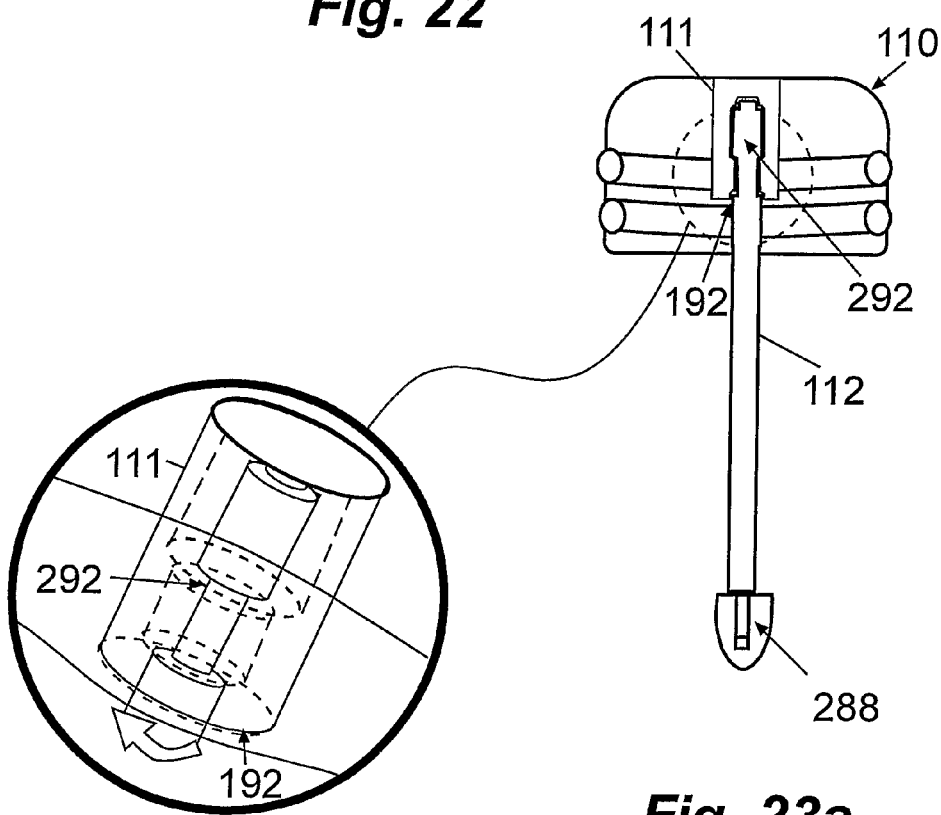
FIGS. 23a-23b are views and diagrams of a connected piston and piston rod.
Figure 23B:
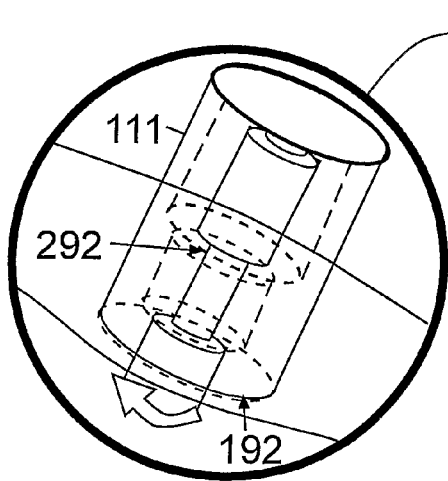

Referring to FIGS. 23*a*-23*b*, views and diagrams depicting a connection between a piston rod 112 and a piston 110 are shown. The piston rod is releasably connectable to a cavity 111 to enable substantially unrestricted rotation of a distal end 292 of the piston rod within the cavity. The distal end 292 of the piston rod 112 having an undercut cross-section can thus be inserted through the opening 192 into a cavity 111 creating a snap-fit arrangement, for example (as shown in FIG. 23b). The unrestricted/free rotation of the distal end within the piston 110 prevents exertion of rotational forces on the piston 110 and enables linear displacement of the piston 110 within the reservoir 220. The snap-fit arrangement further enables a two-way displacement of the piston 110 within the reservoir 220 upon pushing or pulling of the piston rod 112.

Figure 24A:
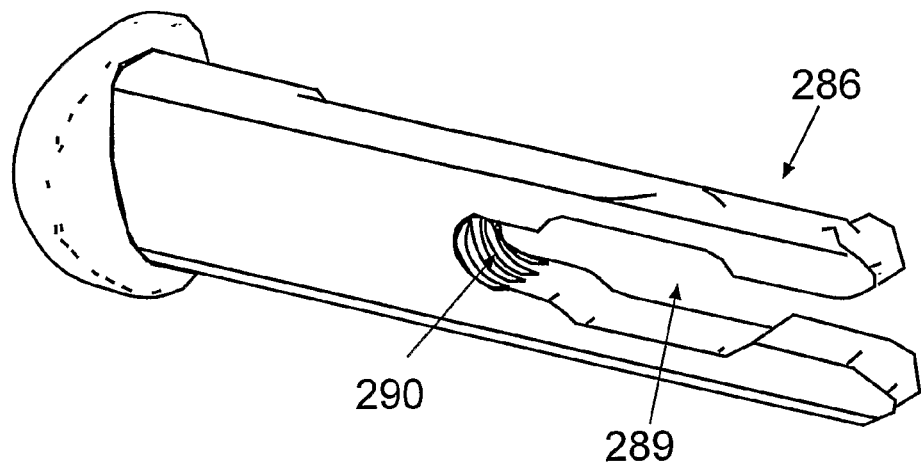
FIGS. 24a-24c are views and diagrams of an engagement member and a piston rod.
Figure 24B:
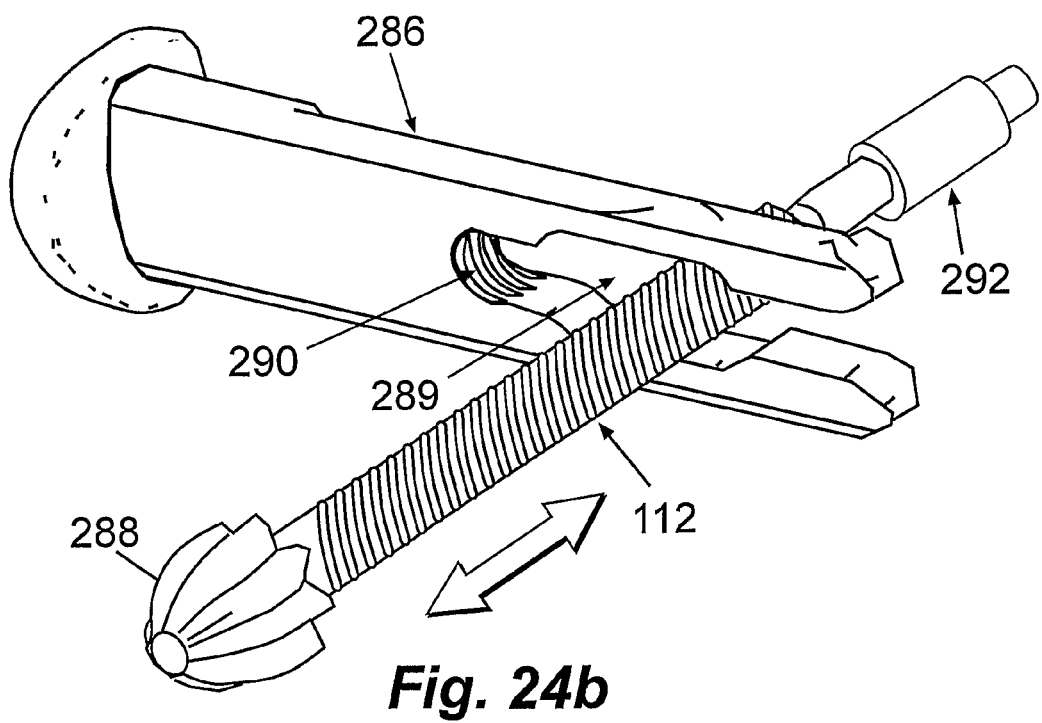
Figure 24C:
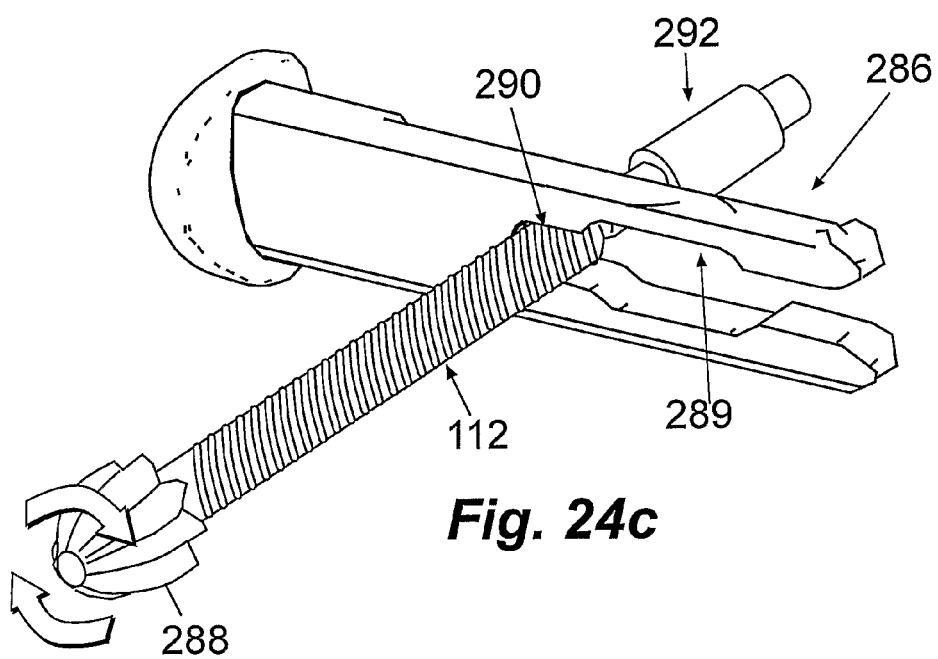

Referring to FIGS. 24a-24c, views and diagrams of an engagement member 286 are shown. The engagement member 286 may be structured with a fork-like shape and include a first opening 289 and a second opening 290. In some embodiments, the first opening 289 is larger than the second opening 290, and, in some embodiments, the second opening 290 is threaded (at least in part) in such a way that the opening's threads match corresponding threads on the threaded piston rod 112. The engagement member 286 may be manually operated, unlike the automatic engagement member 2861 the operation of which is further described in detail in relation to FIGS. 40a-42b. Otherwise, the engagement members 2861 and 286 are generally functionally equivalents.

As illustrated in FIG. 24a, the opening 289 may be sized to enable substantially unrestricted displacement of the piston rod. That is, when the piston rod is placed within the opening 289, the piston rod 112 is displaced in a free, non-controlled translation movement within at least the disposable part of the dispensing device. This is illustrated by the double-headed arrow in FIG. 24b. Such free movement is performed, for example, during reservoir filling and priming as illustrated for example in FIGS. 25a-25f.

The small opening 290 is configured to friction fit the threaded piston rod 112 in order to lock the rod 112 relative to member 286 and prevent free movement thereof. In some embodiments, the small opening 290 may include a plurality of threads (shown in FIGS. 24a-24b) configured to interact with the threads of the piston rod 112, as illustrated in FIG. 24c, to provide a controlled linear movement of the rod 112 relative to the reservoir. Accordingly, the rod 112 may be configured to rotate along the threading of the small opening 290. Such rotational motion of the rod 112 translates into linear motion of the rod 112 that is substantially perpendicular to the plane of the engagement member 286. In some embodiments, the piston rod 112 can be rotated in any direction (clockwise or counterclockwise). The direction of rotation of the piston rod 112 can be chosen to prevent accidental slippage of the piston rod 112 from the small opening 290 into the opening 289. In some embodiments, the opening 290 can include a stopper mechanism (not shown) that will prevent such slippage. The stopper mechanism may be, in some embodiments, an extension from the surface of the small opening 290.

Referring to FIGS. 25a-25f, diagrams depicting a procedure of filling the reservoir 220 with therapeutic fluid, and priming the fluid path, are shown. The dispensing unit uses an engagement member 286 which may be manually operated. In some embodiments, the patient can connect a container 6 of therapeutic fluid (e.g., insulin) directly to the outlet port 210 of the disposable part 200. An example for a container 6 may be a corked glass bottle to store insulin.

Figure 25A:
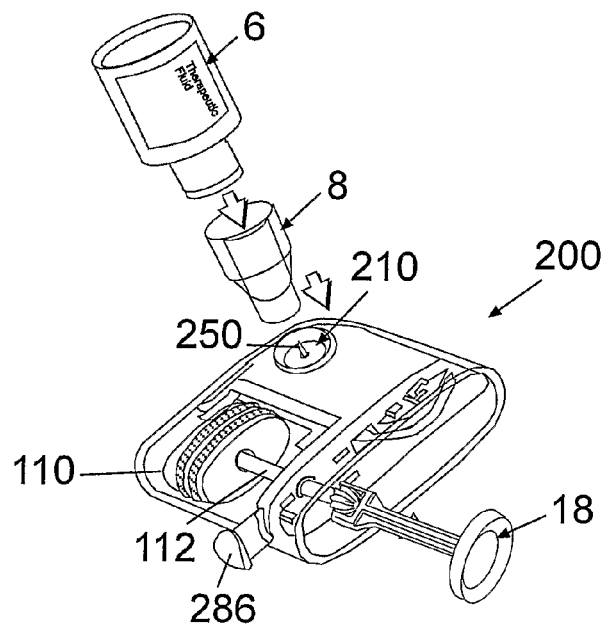
FIGS. 25a-25f are diagrams depicting a procedure of drug drawing and reservoir filling using an adapter, and performing a subsequent flow path priming.

In some embodiments, an adapter 8 is used to connect the container 6 to the outlet port 210, as shown in FIG. 25a, to enable fluid communication between the container 6 and the reservoir. In some embodiments, the adapter 8 may be provided separately from the disposable part 200 and the patient may be required to connect the adapter to the disposable part 200 prior to commencing the filling procedure. In some embodiments, the adapter 8 may be already connected to the disposable part 200.

Figure 25B:
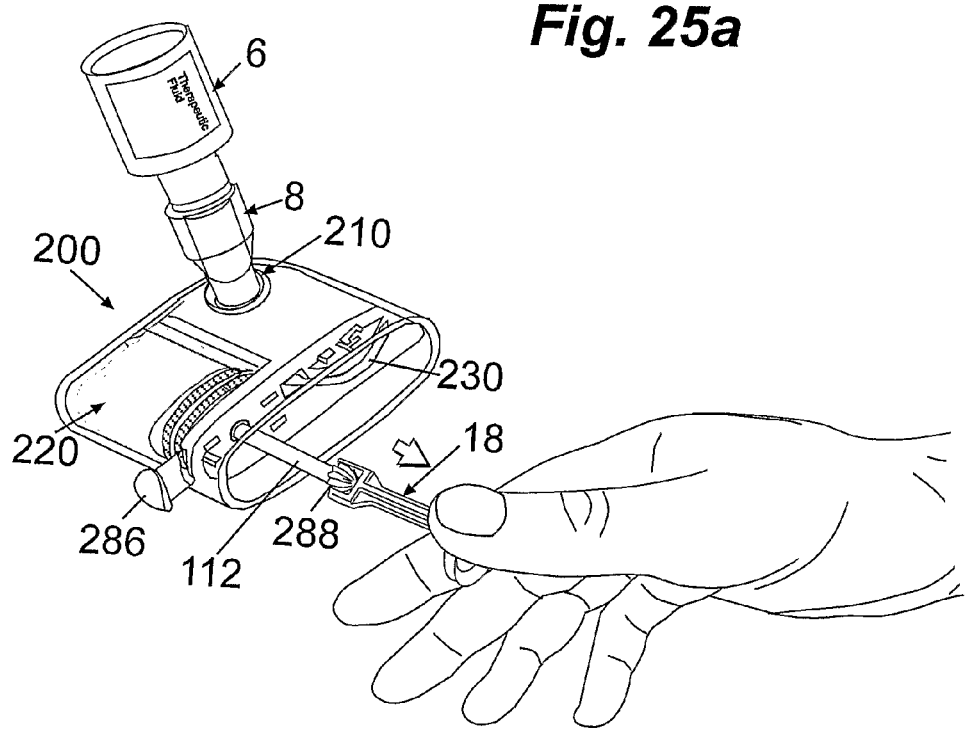

During the filling procedure, the patient draws back the piston rod 112 to pump the therapeutic fluid from the container 6 to the reservoir (as shown in FIG. 25b). The amount of therapeutic fluid (the therapeutic fluid is indicated by the gray coloring) which enters the reservoir is controlled and/or determined by the patient (as long as it is under the maximum capacity of the reservoir, e.g., 2 cc, 3 cc, etc.). During the filling procedure, the engagement member 286 is disengaged (e.g., pulled away from the disposable part 200) to enable free movement of the piston rod 112.

In some embodiments, the patient may be required to push air from the reservoir into the sealed container 6 prior to drawing therapeutic fluid, to pressurize the container 6 and facilitate an easy and low-resistant drawing of therapeutic fluid from the container 6 into the reservoir 220.

Figure 25C:
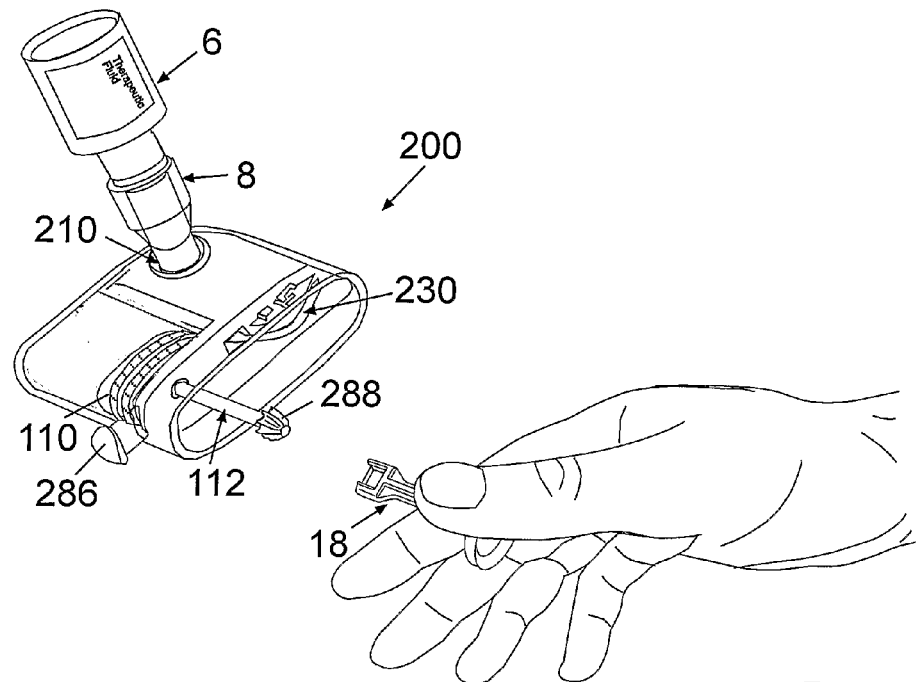

In some embodiments, the patient can grip the tip 288 to pull the piston rod 112. In some embodiments, during the filling procedure, pulling the piston rod 112 can be performed by a dedicated auxiliary handle 18, as shown in FIGS. 25a-25c. An auxiliary handle 18 can be used to pull away the rod 112 from the disposable part 200 (see FIG. 25b) to enable a more convenient and safe grip of the piston rod 112. In some embodiments, the auxiliary handle 18 can also be used to push the piston rod 112 into the reservoir 220, for example, in order to push air into the fluid container prior to drawing therapeutic fluid, or to remove any air bubbles remaining in the reservoir 220 following completion of the filling process. The distal end of the handle 18 is configured to receive the piston rod's tip 288 and connect to it firmly without damaging the tip 288 and/or the piston rod 112. The proximal end of the handle 18 is configured to enable convenient gripping by the user/patient.

Figure 25D:
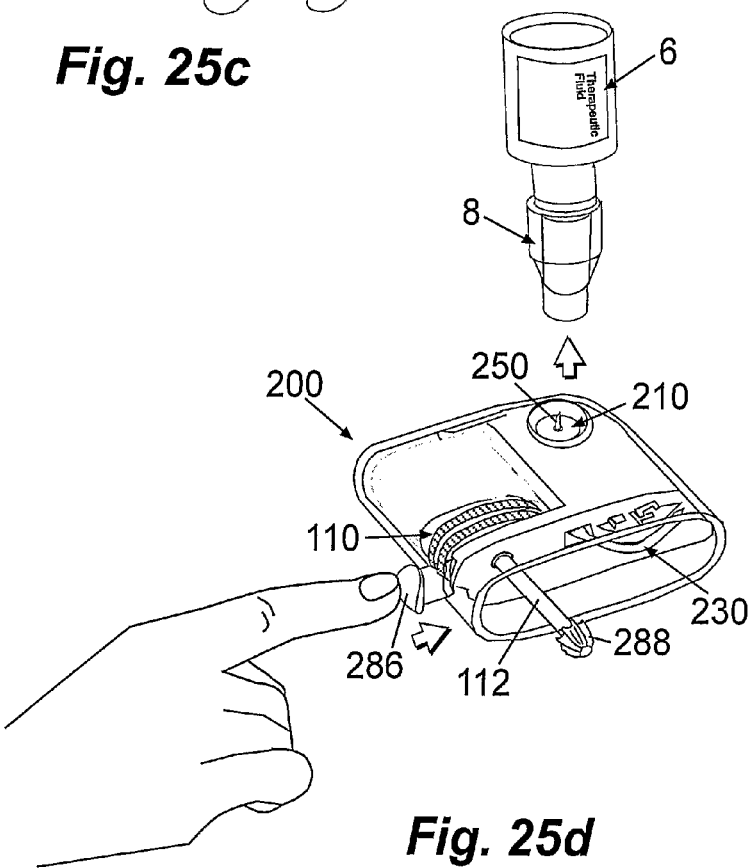
Figure 25F:
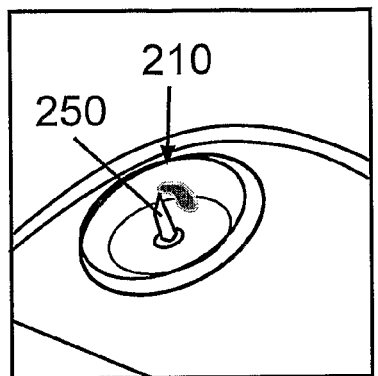
Figure 25E:
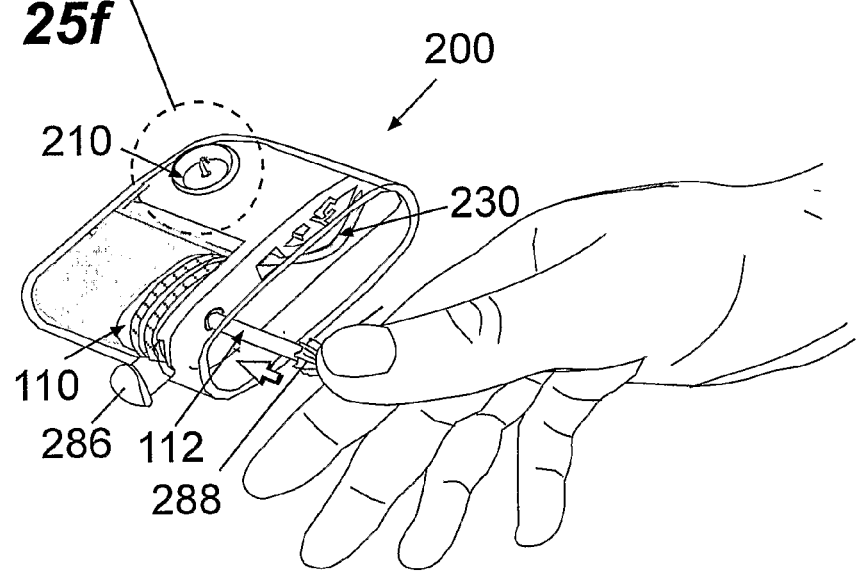

Once the filling procedure is completed, as illustrated in FIGS. 25c-25d, the auxiliary handle 18 can be removed, and the container 6 along with adapter 8 can be removed as well from the outlet port 210. As illustrated in FIG. 25e, manual priming may be achieved by pushing the piston rod 112 forwardly until a one or more drops of therapeutic fluid appear at the end of the connecting lumen 250 of the outlet port 210 (see FIG. 25f). Manual priming can also be performed using the auxiliary handle 18 prior to its removal. The priming process may be performed to establish and verify proper fluid communication between the reservoir and the connecting lumen 250, i.e., to make sure that there are no air bubbles and/or occlusion in the reservoir 220, the fluid channel 232, the connecting tube 230 or the connecting lumen 250.

As illustrated in FIG. 25d, the engagement member 286 can be engaged (e.g., pushed into the housing within the disposable part 200), to thus lock the piston rod 112 and prevent free movement of the piston rod 112 and any attendant accidental discharge of the fluid from the reservoir. In some embodiments, engagement of the engagement member 286 can be done following the manual priming shown in FIGS. 25e-25f.

Referring to FIGS. 26a-26f, diagrams depicting a procedure to fill the reservoir using an adapter 90 are shown. The adapter 90 has an opening 92 to be received by the outlet port 210 of the disposable part 200. The opening 92 is sealed by a rubber septum 94 which can be pierced by the connecting lumen 250 of the disposable part 200. The opening 92 is fluidly coupled with an adapting needle (as shown in greater detail in FIGS. 27a-27c) residing within the adapter's inlet port 96.

Figure 26A:
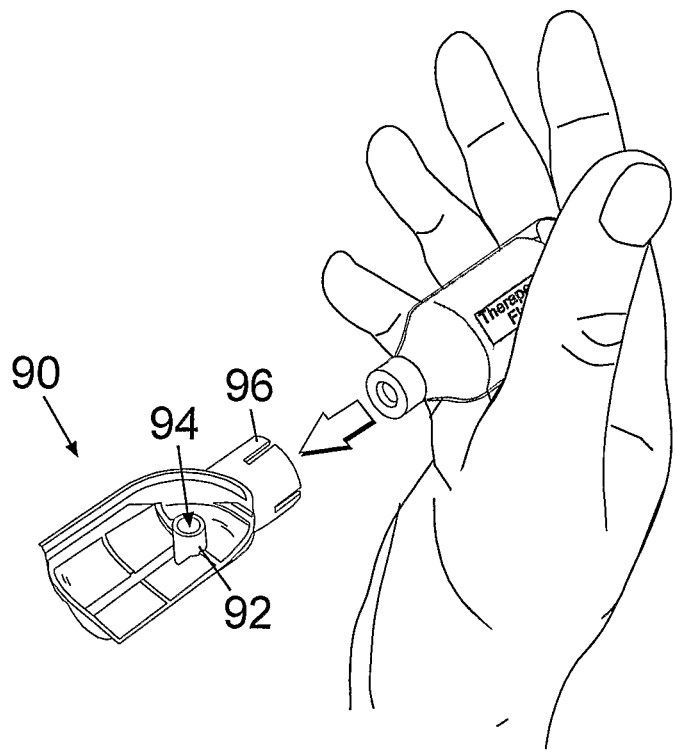
FIGS. 26a-26f are diagrams depicting a procedure of drug drawing and reservoir filling using an adapter.
Figure 26B:
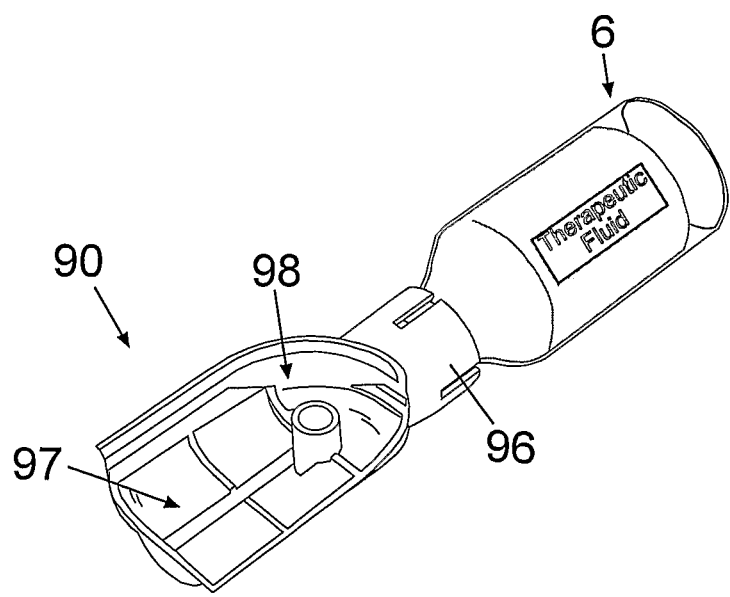
Figure 26C:
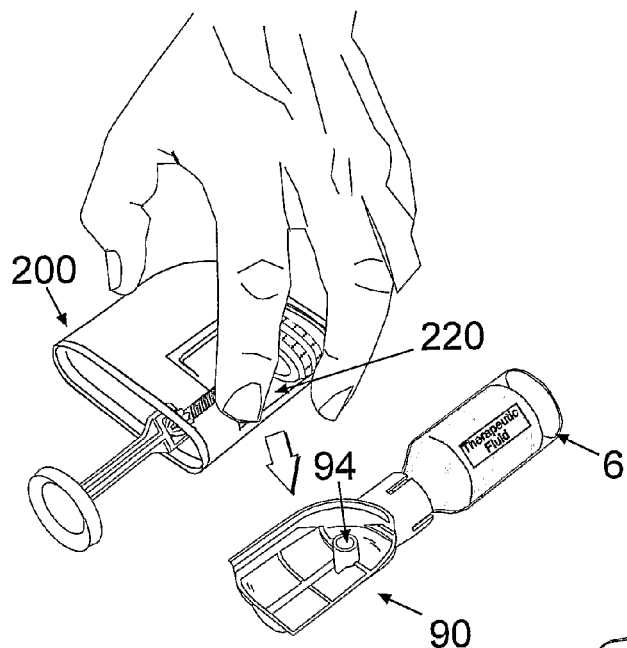
Figure 26D:
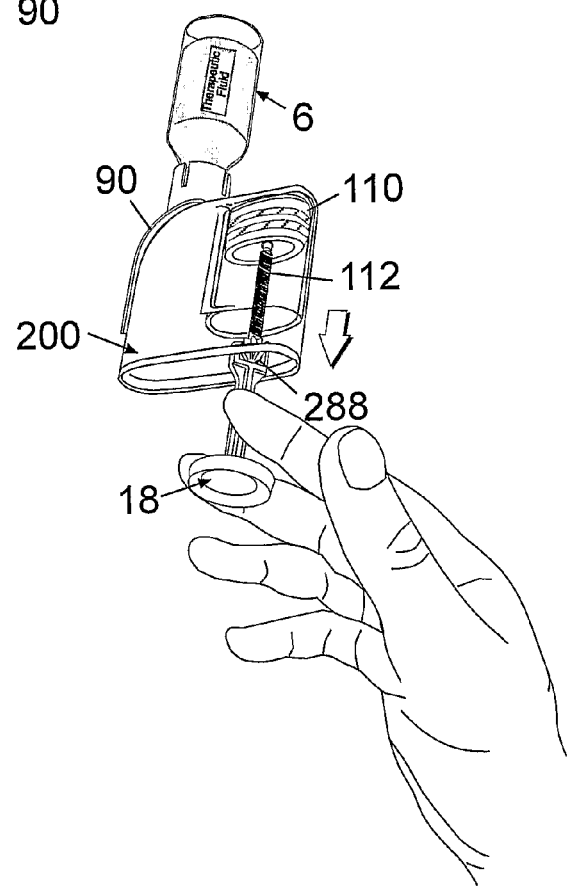
Figure 26E:
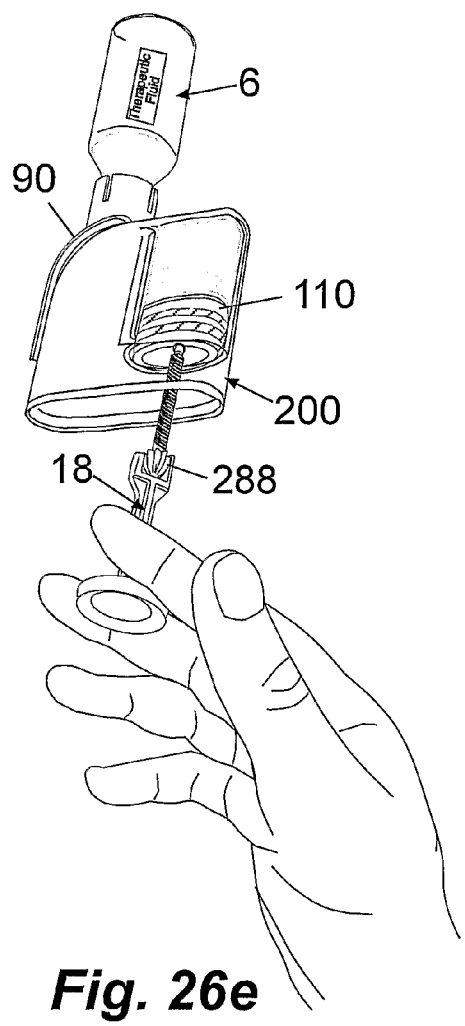
Figure 26F:
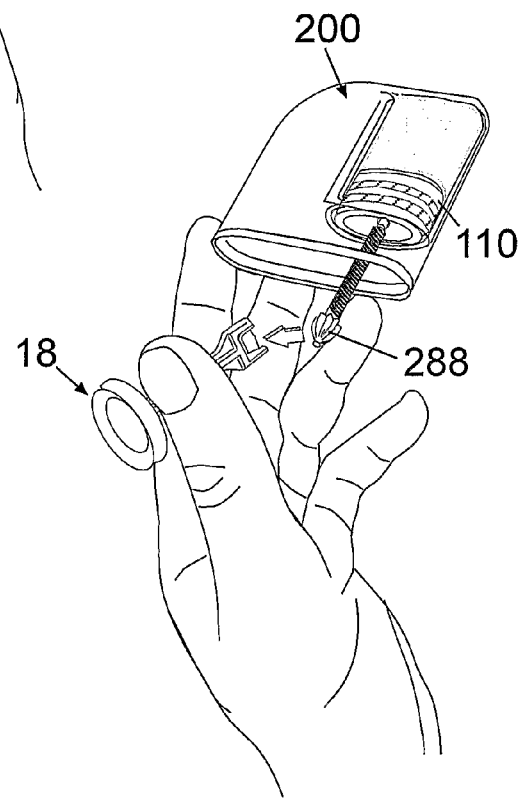

As illustrated in FIG. 26b, the inlet port 96 of the adapter 90 is configured to receive the container 6 containing the therapeutic fluid. The adapting needle pierces the septum of the container (e.g., a cork of an insulin vial) to enable fluid flow between the container 6 and the adapter 90. The adapter 90 further includes a base 97 having a curved wall 98 to match the disposable part 200. Referring to FIG. 26c, when the disposable part 200 is connected to the adapter 90, the connecting lumen 250 pierces the rubber septum 94 to establish a path for fluid flow between the container 6 and the reservoir 220. As illustrated in FIGS. 26d-26e, the filling of the reservoir is performed by pulling backwards the piston rod 112 (and thus the piston 110) in the direction of the single-headed arrow. As noted, in some embodiments, pulling the piston rod 112 can be performed via an auxiliary handle 18 which connects to the tip 288 of the piston rod 112. The adapter 90 attached to the disposable part 200 and the fluid container should be held in a vertical position as the piston rod 112 is being pulled backwards, i.e., such that the container 6 is positioned upside down. After the reservoir is filled with the desired amount of therapeutic fluid (as may be determined, for example, by the user), the adapter 90 and the container 6 (not shown in FIG. 26f) can be removed and the handle 18 may be disconnected from the tip 288 (as shown in FIG. 26f). After filling the reservoir with therapeutic fluid, the user may perform the priming process before connecting the disposable part and reusable part (as similarly described in relation to FIGS. 25e-25f).

Figure 27A:
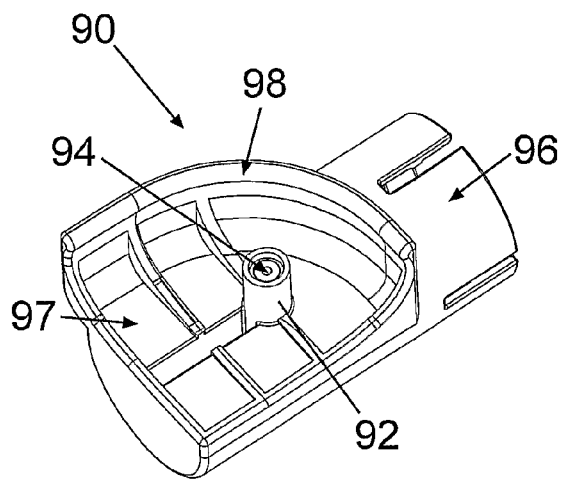
FIGS. 27a-27c are views and diagrams of an adapter.
Figure 27B:
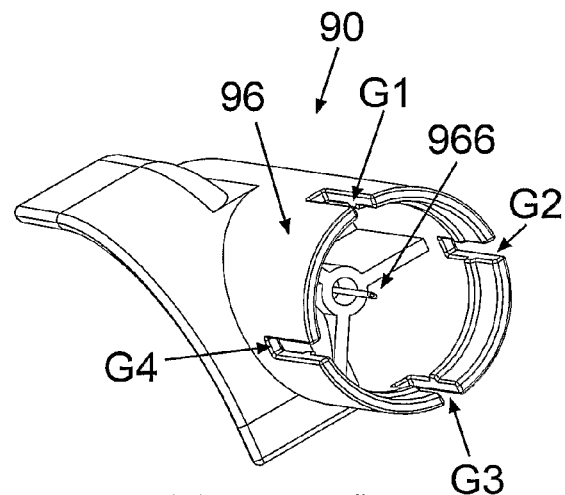
Figure 27C:
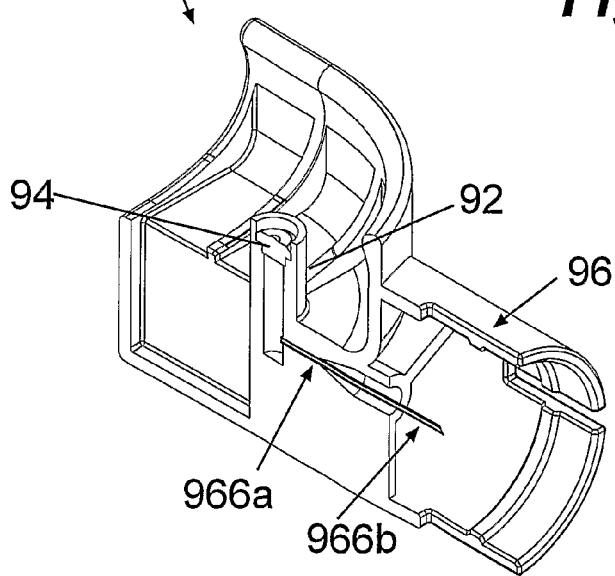

Referring to FIGS. 27a-27c, views of an adapter 90 having a female end and male end are shown. FIG. 27a illustrates the female end of the adapter 90 having an opening 92 sealed by a rubber septum 94. In some embodiments, the septum 94 may be pierced recurrently (i.e., the septum is adapted to be pierced from time to time) by the connecting lumen 250 of the disposable part 200. In some embodiments, the female end of the adapter 90 further includes a base 97 having a curved wall 98 matching the portion of the disposable part 200 which surrounds the outlet port 210. FIG. 27b illustrates a male end of the adapter 90 structured as an adapting needle 966 which resides within the adapter's inlet port 96. The inlet port 96 is connectable to the container 6 containing the therapeutic fluid, e.g., the inlet port 96 includes a circular border wall defining a depression structured to receive the circular neck of the fluid container 6. In some embodiments, the border wall includes gaps G1, G2, G3 and G4 that provide a discontinuous arrangement of the wall, and thus provide the border wall with a level of elasticity. The number of gaps may vary. Seen in the center of the inlet port 96 is the sharp end of the adapting needle 966, which is configured to pierce the septum of the container 6.

FIG. 27c is a cross-section view of the adapter 90 illustrating how the fluid flows within the adapter 90 from the adapting needle 966 to the opening 92, thus establishing fluid path between the container and the connecting lumen of the disposable part. The sharp end 966b of the adapting needle 966 resides within the inlet port of the adapter 96 and is positioned such that it can pierce the septum of the fluid container. A distal end 966a of the adapting needle 966 is associated with the opening 92 in the female end of the adapter 90 to enable fluid to flow from the adapting needle 966 to the opening 92, and vice versa. As mentioned above, the opening 92 is provided with a septum 94 that can be pierced by the connecting lumen of the disposable part. The sharp end 966b of the adapting needle 966 is, in some embodiments, fully concealed within the depression defined by the border wall and is therefore, under those circumstances, not readily accessible by the user. Concealment of the sharp end 966b can thus prevent inadvertent puncture of the user. Further examples of adapters such as adapter 90 are described, for example, in co-pending/co-owned U.S. patent application Ser. No. 11/989,680, the content of which is hereby incorporated by reference in its entirety. It is to be noted that an adapter such as the adapters described herein (including the adapter 90) may be used in conjunctions with other types of fluid dispensing devices. Furthermore, adapters such as those described herein, may be used in conjunctions with other types of devices/systems (e.g., devices/systems where it may be necessary or desirable to transfer fluid from one container to another container/housing) and not just with fluid dispensing devices.

Figure 28A:
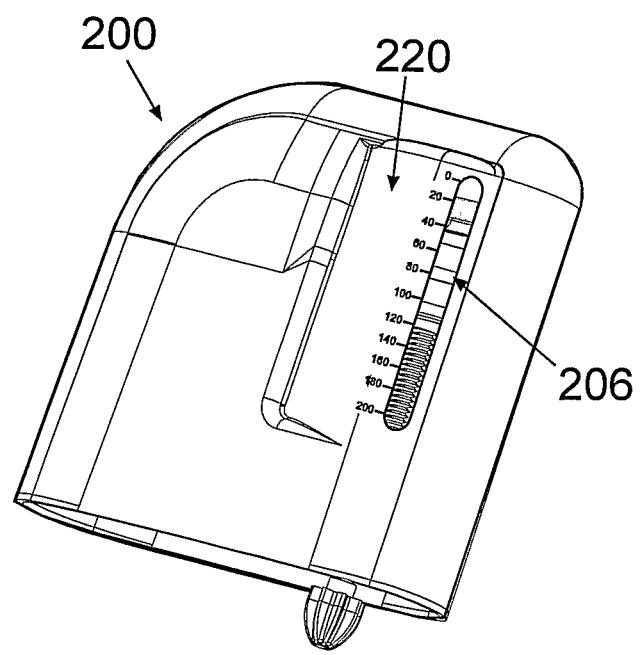
FIGS. 28a-28c are views and diagrams of disposable parts having various transparent windows and graduations scales for fluid level monitoring.
Figure 28B:
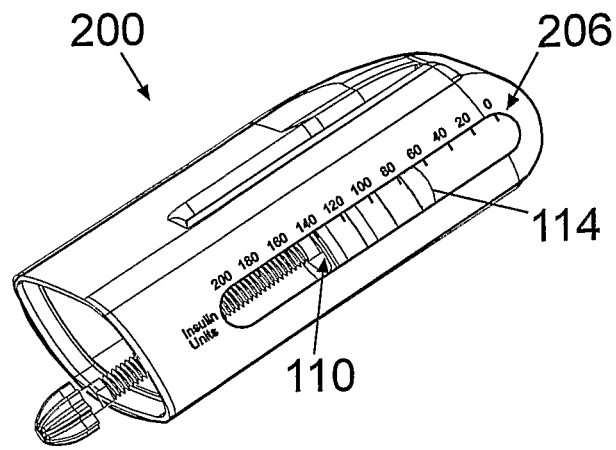
Figure 28C:
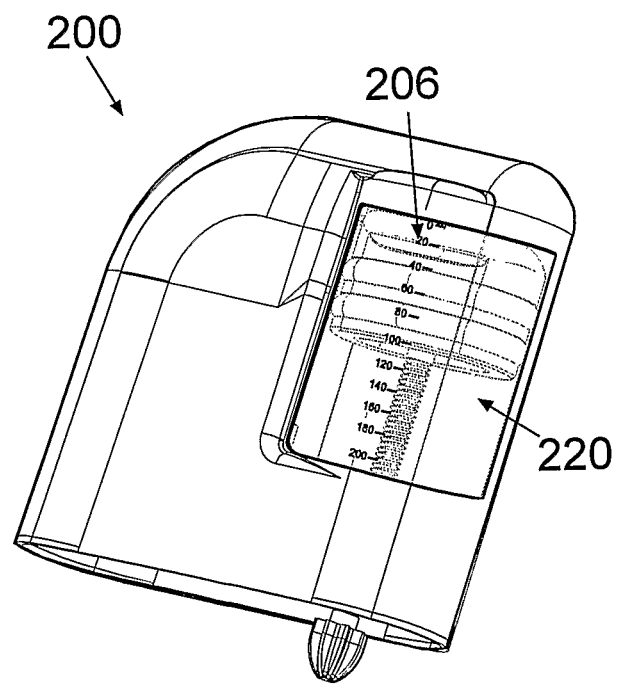

To enable a user to view the amount of fluid within the reservoir (e.g., during filling of the reservoir), at least a portion of the reservoir walls may be transparent. At least one scale of graduations 206 can be marked/printed along the reservoir 220 in various locations, as shown in FIGS. 28a-28c. In some embodiments, two (2) scales of graduations, one on the front of the reservoir and one on the back, may be included so that both right-handed and left-handed users could see a scale when filling the reservoir. Additionally, the piston 110 may also be marked to facilitate a more accurate measurement of fluid in the reservoir 220. For example, the nose 114 of the piston 110 can be colored (as shown in FIG. 28b), or a colored seal/gasket of the piston can be used.

Figure 29:
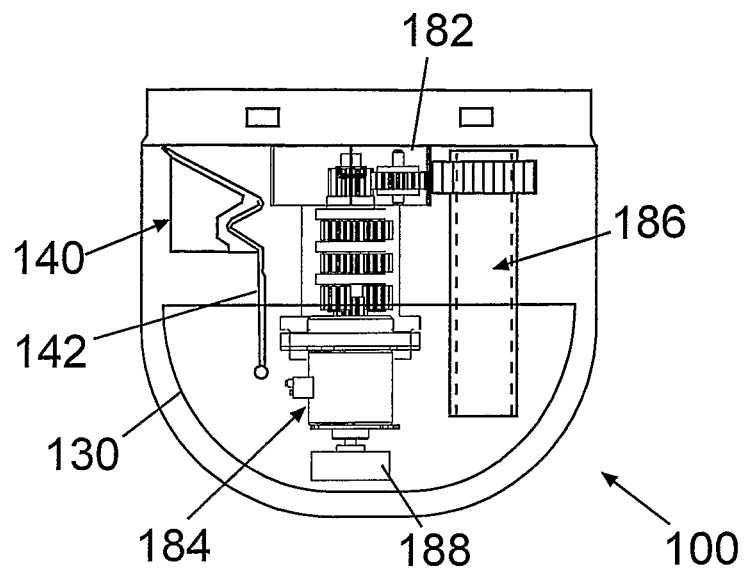
FIG. 29 is a diagram of a reusable part and its components.

FIGS. 29-37c illustrate the reusable part and its components. Referring to FIG. 29, a diagram of a reusable part 100 and its components is shown. The reusable part 100 includes at least a portion of a driving mechanism having a motor 184 and gears 182, which drive a threaded cylinder 186 (referred-to as a "sleeve" or "drive sleeve"). In some embodiments, the motor 184 can comprise a stepper motor, a DC motor, an SMA actuator, etc. The gears may include a unitary planetary gear, as shown in FIG. 29, or any other power transmission mechanism such as a set of couplable cogwheels. The motor and/or gears can be coupled to one or more monitoring mechanisms (also referred to as monitoring units), such as a revolution counter or an encoder producing digital signals, or any other mechanism to monitor the operation of the driving mechanism, including the driving mechanism's motor, cogwheels and/or drive sleeve. The reusable part 100 can further comprise at least a portion of an occlusion sensor 140 with a sensing element 142 which is electrically connected to the Printed Circuit Board (PCB)/electronics 130 of the reusable part.

In some embodiments, the sleeve 186 is configured to receive the piston rod 112 of the disposable part 200 upon connection of the reusable part 100 and the disposable part 200, and to transfer rotational movement to the tip 288 of the piston rod 112 and the piston rod 112. The reusable part 100 may further includes electronics, designated with the reference numeral 130, and may comprise one or more of, for example, a controller, a processor, a transceiver, an antenna, etc.

In some embodiments, the reusable part 100 may include connectors to establish electrical communication between a power source 240 (e.g., a battery) located, for example, in the disposable part, and the reusable part's electronics 130 (as illustrated in FIGS. 43a-43d).

In some embodiments, the reusable part 100 may also include sensors, including sensors to determine the amount of therapeutic fluid in the reservoir (shown in greater detail in FIGS. 44a-45b), and/or an occlusion sensor 140, as shown in greater detail in FIGS. 46a-46e.

Figure 31:
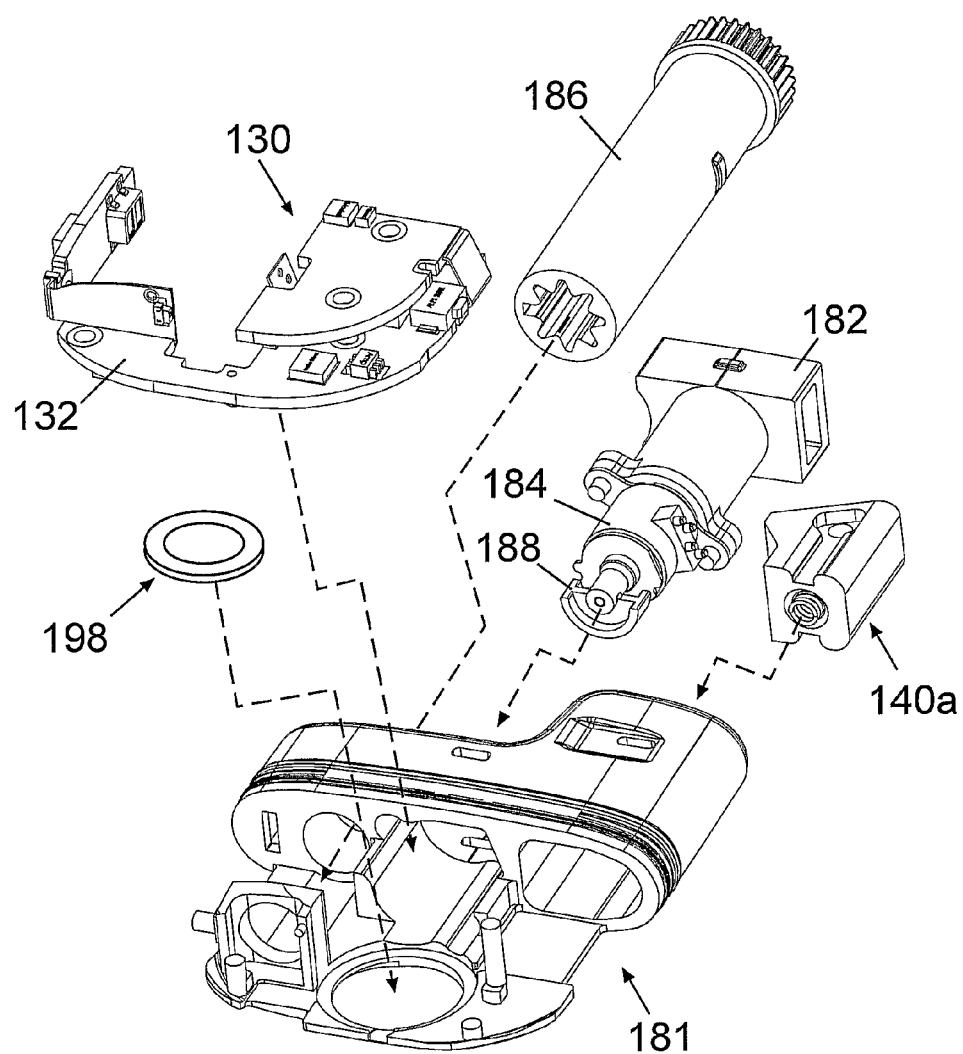
FIG. 31 is an exploded view of a reusable chassis and reusable components.
Figure 32:
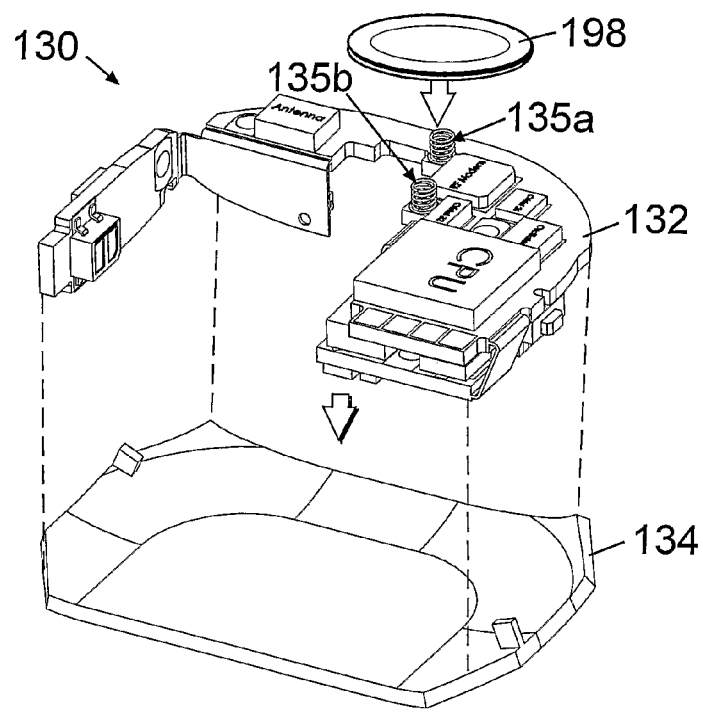
FIG. 32 is a view of a PCB, capacitor and buzzer.

In some embodiments, the reusable part 100 may comprise further a notification mechanism (e.g., visual/audible/vibrational notifiers), as shown in greater detail in FIGS. 31 and 32).

In some embodiments, the reusable part 100 may include seals/gaskets to prevent seepage of liquid and/or contaminants into the dispensing unit 10 when the reusable part 100 and the disposable part 200 are connected and operable. This is described in greater detail in FIGS. 48a-48b.

Figure 30A:
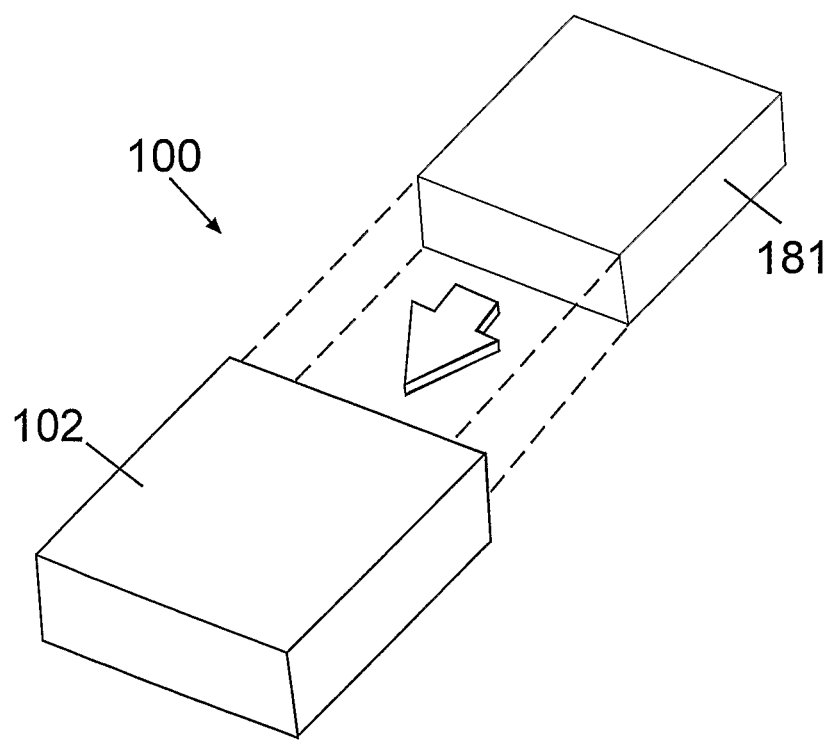
FIGS. 30a-30b are views and diagrams of a reusable part that includes a housing and chassis.
Figure 30B:
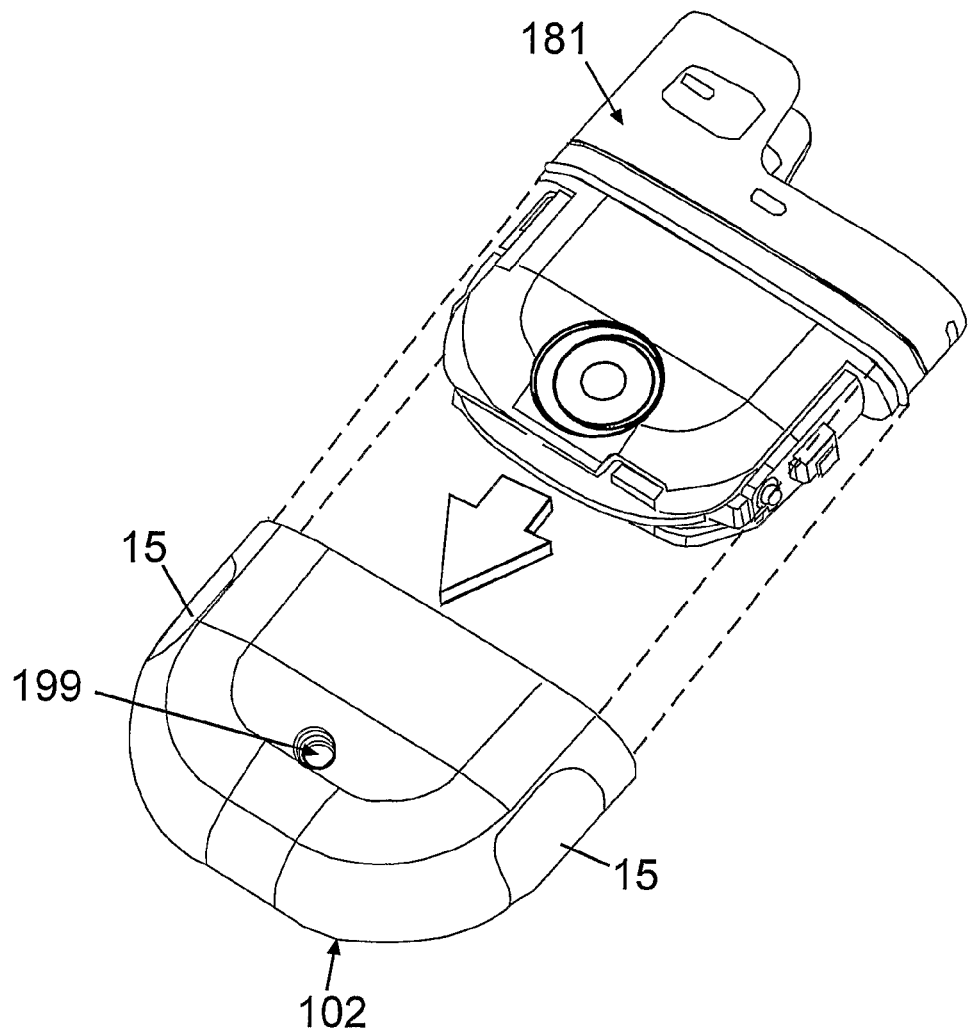

Referring to FIGS. 30a-30b, views and diagrams of a reusable part 100 comprising a reusable chassis 181 and a reusable housing 102 (also referred-to as a "reusable pocket") are shown. Referring to FIG. 30a, the chassis 181 is configured to be received within the housing 102, for example, during manufacturing/assembly of the parts. As illustrated in FIG. 30b, the housing 102 can be configured to have the cross section of a matching chassis 181. The housing can include buttons/switches 15 to enable, for example, the user interacting with the unit to, for example, provide operation instructions to control, for example, dose delivery. In some embodiments, the housing 102 further includes a port/aperture 199 to enable air passage into and out of the internal cavity of the reusable housing 102 to facilitate, for example, operation of a Zinc-air battery (or batteries), enable pressure equilibrium, and to enhance the quality and level of sound generated by a buzzer (i.e., to facilitate operation of an auditory notifier). The housing 102 is configured to cover and protect the chassis 181 that is configured to have reusable components fitted or otherwise accommodated on it.

In some embodiments, the reusable chassis 181 is assembled as a module that is ready for easy and convenient assembly with the reusable housing 102 by inserting the chassis 181 into the housing 102. Similar modular assembly may also be implemented for disposable housings and their components.

Referring to FIG. 31, an exploded view of the reusable components and their positions within the reusable chassis 181 is shown. In some embodiments, a dedicated structure of a Printed Circuit Board ("PCB") accommodates at least a portion of electronics 130. The PCB may be structured as a compact rigid-flex PCB 132 that can be received by the chassis 181. A portion of the driving mechanism included in the reusable part 100 may comprise, in some embodiments, a motor 184 coupled to a planetary gear 182 and to a "flag wheel" 188 of a revolution counter. These components are received within the chassis 181. The chassis may further accommodate a sleeve 186, a portion of the occlusion sensor 140a, a buzzer 198 and a capacitor (not shown in FIG. 31).

Referring to FIG. 32, a view of a flex-rigid Printed Circuit Board (PCB) 132 in a folded configuration as it resides within the chassis 181 is shown. As illustrated, the PCB 132 may accommodate one or more electronic components (e.g., a CPU, an antenna, an RF modem, etc.). The PCB 132 may also support a buzzer 198 using springs (135a, 135b). In some embodiments, a capacitor 134 with a large capacitance, e.g., 2F (referred-to as "supercap") can be used in conjunction with a pulsed-energy operation to conserve energy, as described, for example, in co-pending/co-owned International Patent Application No. PCT/IL08/001,650, the content of which is hereby incorporated by reference in its entirety.

Figure 33A:
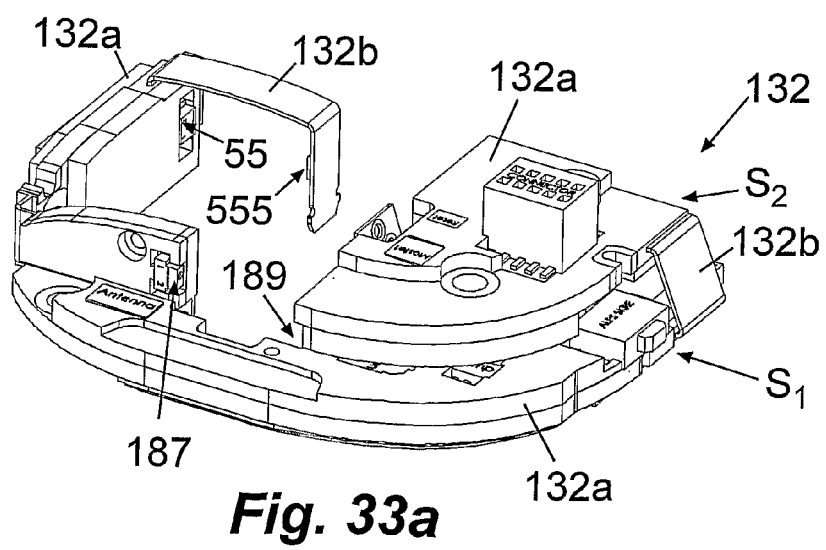
FIGS. 33a-33b are views and diagrams of a rigid-flex PCB in its folded (33a) and spread (33b) configurations.
Figure 33B:
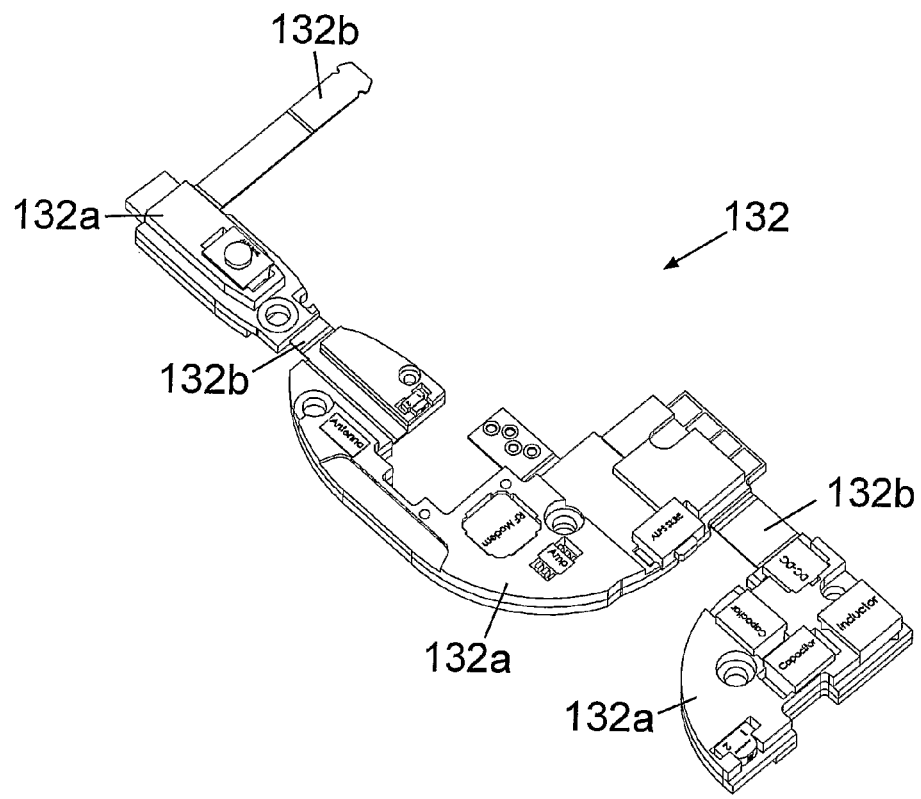

Referring to FIGS. 33a-33b, views and diagrams of a PCB 132 including rigid portions (designated as 132a) and flexible portions (designated as 132b) are shown. The PCB 132 is shown in its two configurations, a) spread configuration (shown in FIG. 33b), which is utilized during the manufacturing process to place electrical components on the board, and b) a folded configuration (shown in FIG. 33a) comprising two or more stages or tiers (S1 and S2). The flex-rigid PCB 132 enables a compact spatial arrangement of electronic components.

As further shown in FIG. 33a, placed on the PCB 132 are a Light Emitting Diode ("LED") 55, a detector 555 of the sensor which facilitates determination of the amount of fluid in the reservoir (shown in greater detail in FIGS. 44a-44c) and a LED 187 and a detector 189 used in the implementation of the revolution counter.

Figure 34:
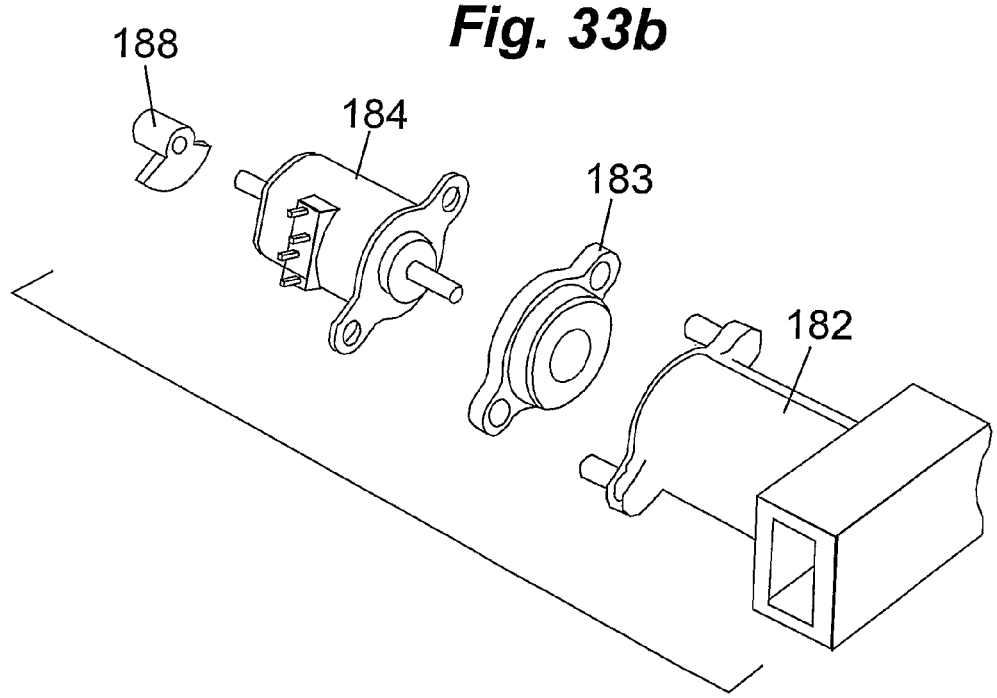
FIG. 34 is an exploded view of a motor, gear, and a portion of a revolution counter.

Referring to FIG. 34, an exploded view of an arrangement that includes a motor 184, a planetary gear 182 and a flag wheel 188 of a revolution counter is shown. The motor 184 and planetary gear 182 are connected via an adaptor 183 which, in some embodiments, is made of a plastic material.

Figure 35A:
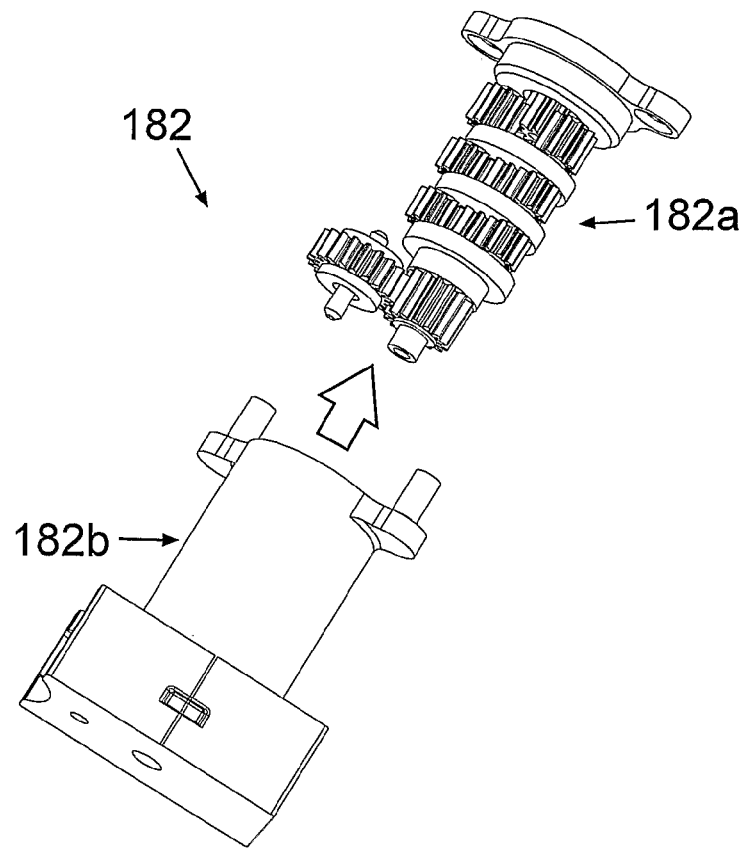
FIGS. 35a-35b are views and diagrams of a planetary gear.
Figure 35B:
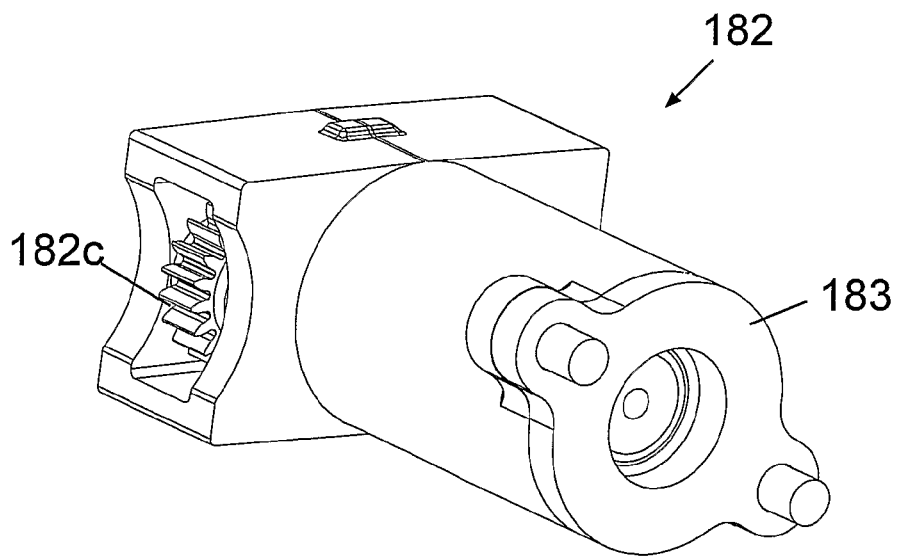

Referring to FIGS. 35a-35b, views and diagrams of a planetary gear system are shown. The planetary gear 182 includes a set of cogwheels 182a that includes, for example, several stages (or degrees), e.g. three (3) stages, that reside within a housing 182b having a threaded interior. The planetary gear 182 is mechanically coupled to a motor (not shown in FIGS. 35a-35b) via an adaptor 183 and receives the rotational movement generated by the motor. The planetary gear 182 reduces the number of rotations over a period of time while increasing the moment. This rotational moment is transferred to the sleeve (not shown in FIGS. 35a-35b) by the cogwheel 182c (shown in FIG. 35b).

Figure 36:
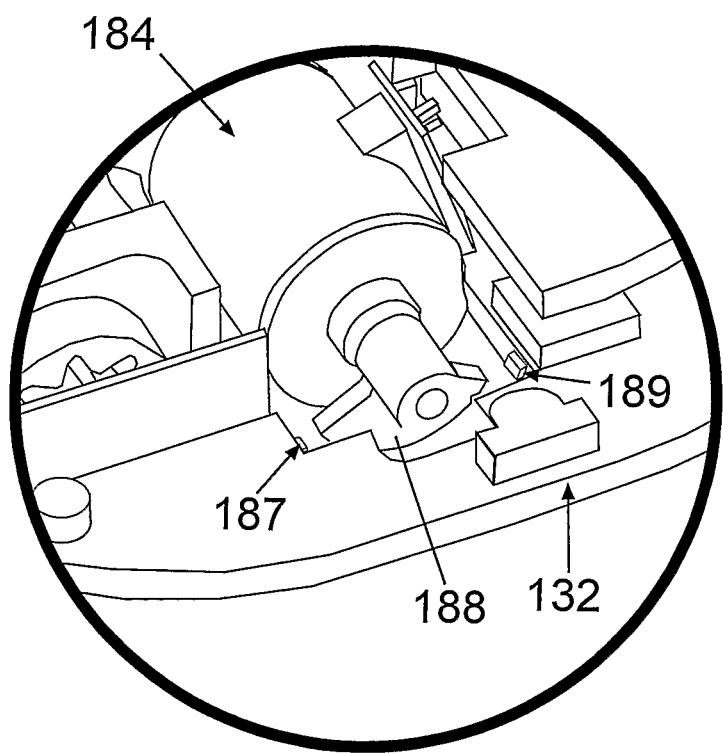
FIG. 36 is a view of a revolution counter for monitoring motor rotation.

As noted, in some embodiments, various parts/components of the driving mechanism may be coupled to one or more monitoring mechanisms to monitor operation of, for example, the motor, the cogwheels and/or the drive sleeve. Referring to FIG. 36, a view of a revolution counter, used to monitor, for example, the operation of the motor, is shown. The rotation of the motor 184 can be monitored by a revolution counter that includes a flag wheel 188 connected to the shaft of the motor 184. The flag wheel 188 rotates between a LED 187 and a detector 189 which are disposed on the PCB 132. The LED 187 and the detector 189 are positioned, in some embodiments, perpendicularly to the shaft of the motor (i.e., perpendicularly to the rotation axis of the flag wheel 188). Upon rotation of the motor shaft (and the flag wheel 188), the flag wheel 188 periodically blocks the emitted light from propagating in the direction of the detector 189. The detector 189 generates a signal representative of the amount of detected light and/or representative of the fact that light was detected, which is sent to the controller for processing. The flag wheel 188 comprises one or more portions of a disc. In some embodiments (e.g., single disc portion embodiments), a transition between light and darkness (or vice versa) indicates completion of one full revolution of the motor. In some embodiments (e.g., multiple disc portions embodiments), a transition between light and darkness (or vice versa) indicates completion of a part of a revolution of the motor (e.g., half a motor revolution when a flag wheel comprising two portions of a disc is used).

Various configurations of a monitoring mechanism are also described in co-pending/co-owned International Patent Application No. PCT/IL08/000,642, the content of which is hereby incorporated by reference in its entirety.

Figure 37A:
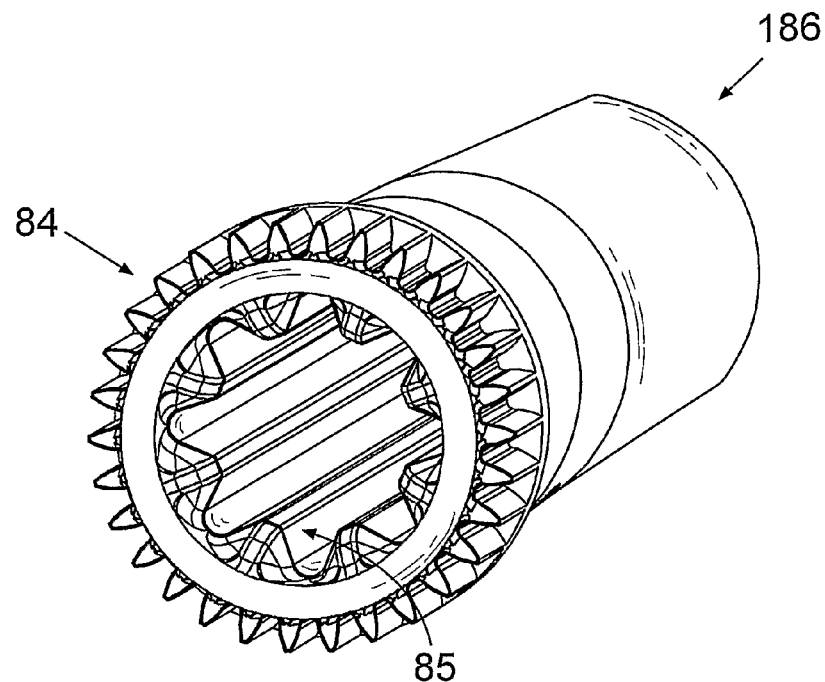
FIGS. 37a-37c are views of a drive-sleeve that include a perspective view (37a), a cross sectional view (37b) and a cross-sectional view of a tip ("juice extractor").
Figure 37B:
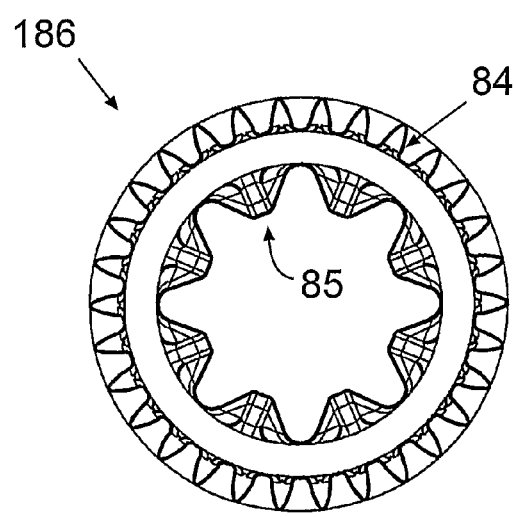
Figure 37C:
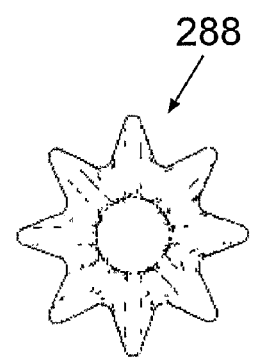

FIGS. 37a-37c illustrate a sleeve 186 structured as a hollow cylinder having inner teeth 85 along the interior of the cylinder and an outer rim 84 having gear teeth. The inner teeth 85 may be structured to form grooves disposed along the sleeve. The grooves are generally uniformly configured throughout the length of the sleeve to enable proper linear movement of the tip of the piston rod within the sleeve. As shown, these grooves may substantially traverse the length of the sleeve 186, and one or more grooves (and in some embodiment, all the grooves) may be arranged parallel to the longitudinal axis of the sleeve 186.

The inner teeth 85 of the sleeve (a cross-sectional view of which is shown in FIG. 37b) are adapted to interact with the tip 288 (a front view of which is shown in FIG. 37c) of the piston rod 112 upon connection of the disposable and reusable parts. The teeth of the tip 288 of the piston rod 112 may be structured as extensions/protrusions on the end of piston rod 112 that mate with the grooves formed by the inner teeth 85. The convex profile of the tip 288 (not shown in FIGS. 37a-37c) enables an easy and smooth coupling of the tip 288 and the sleeve 186. Such coupling involves alignment of the teeth of the tip 288 with the inner teeth 85 of the sleeve 186.

An outer rim 84 of the sleeve 186 may include gear teeth configured to interact with teeth of other rotary gears such as the gear 182c of the planetary gear 182 (shown in FIG. 35b). Thus, by rotating the gears 182, the gear 182c coupled to the sleeve 186 is also rotated, thus rotating the piston rod 112. Rotational motion of the piston rod 112 in turn enables its linear translational motion, which pushes the piston 110, causing linear translational motion of the piston (i.e., when the engagement member is engaged). Such translational motion of the piston 110, in some embodiments, pushes the liquid out of the reservoir and into the connecting lumen.

Figure 38:
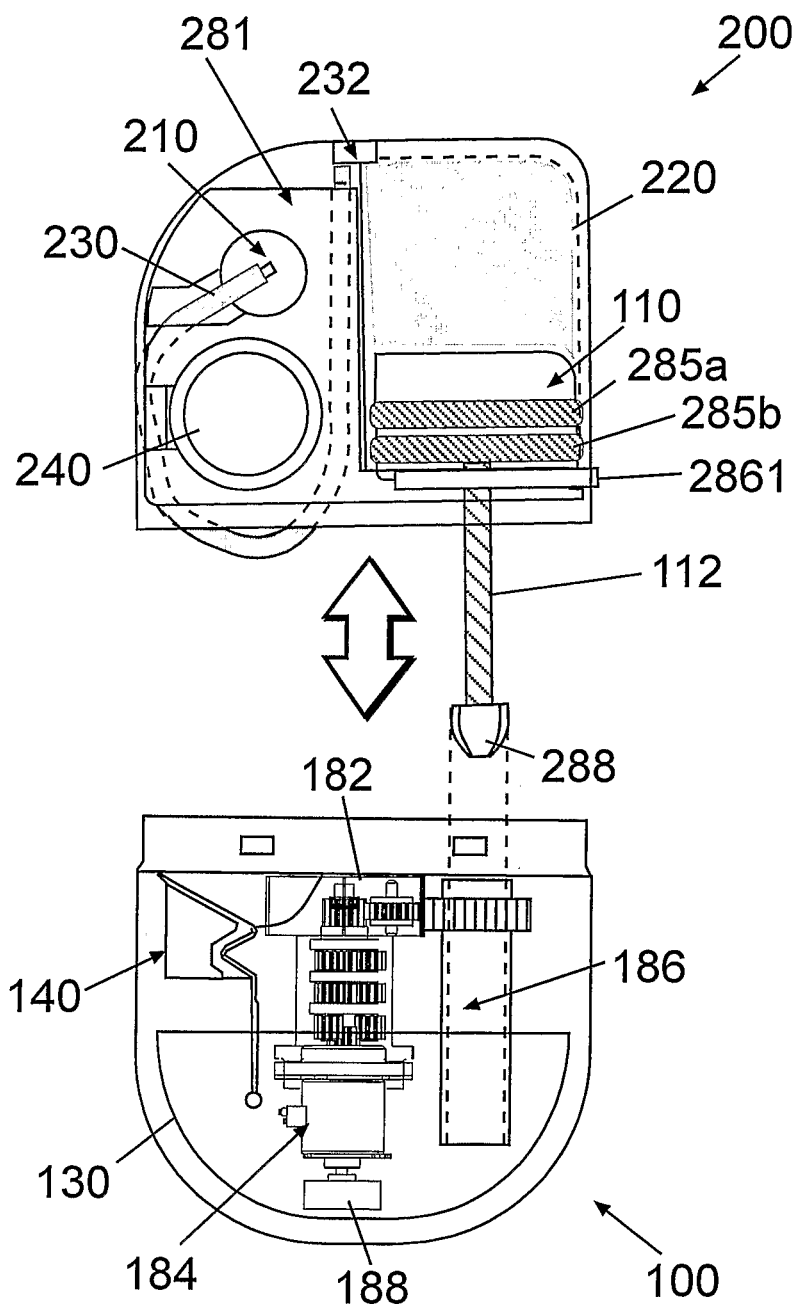
FIG. 38 is a diagram of a two-part dispensing device composed of disposable and reusable parts before connection of the two parts.

Referring to FIG. 38, a diagram of a disposable part 200 and a reusable part 100 ready to be connected together is shown. The reservoir 220 of the disposable part 200 is filled with a desired amount of therapeutic fluid (indicated in gray coloring) and primed. As shown, the engagement member 2861 is not engaged. Free movement of the piston 110 is constrained by seals/gaskets 285a and 285b of the piston 110.

Figure 39:
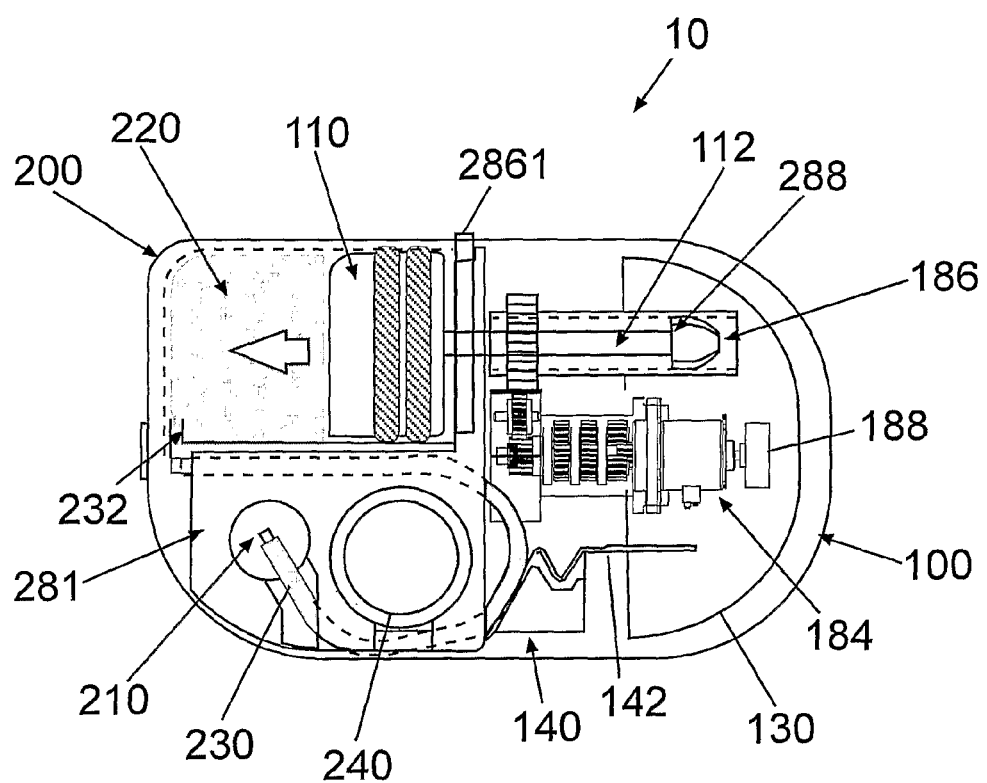
FIG. 39 is a diagram of a two-part dispensing unit composed of disposable and reusable parts after connection.

Referring to FIG. 39, a diagram of a connected two-part dispensing device/unit is shown. As shown, a piston rod 112 is inserted within a sleeve 186 and a power source 240 is electrically coupled to the electronics 130 using, for example, electrical connectors (as shown in detail in FIGS. 43a-43f).

In some embodiments, engagement of the engagement member 2861 can be performed automatically (rather than manually as described above). FIGS. 40a-42b illustrate the engagement member 2861 being automatically engaged upon the connection of a disposable part 200 and a reusable part 100. As described herein, the engagement member 2861 is located within the chassis 281 and includes two conjugated openings: a first opening 2891 (which is preferably smooth) which enables substantially unrestricted movement of the piston rod 112, and a second opening 2901 which is threaded, at least in part, to enable controlled movement of the piston rod 112. In some embodiments, the first opening 2891 is larger than the second opening 2901. The openings 2891 and 2901 are similar, and facilitate similar functions, as the openings 289 and 290, respectively, described in relation to FIGS. 24a-24c. In some embodiments, the engagement member 2861 may include one or more additional openings or slots 2911, to provide the engagement member 2861 with elasticity and thus prevent irreversible deformation of the engagement member 2861 during engagement. In some embodiments, the additional opening/slot 2911 is conjugated with the openings 2891 and 2901. The engagement member 2861 further includes an extension piece referred-to as a "leaf" 2910. When the two parts of the dispensing unit (100 and 200) are not connected (as shown in FIG. 40a), no force is exerted on the leaf 2910 (shown in greater detail in FIG. 40b) and the piston rod 112 can thus be displaced freely through the opening 2891 of the engagement member 2861.

Upon connection of the disposable part 200 and reusable part 100, as shown in FIG. 41a), the leaf 2910 is pressed and flattened (see FIG. 41b) causing the member 2861 to move laterally so that the small threaded opening 2901 is coupled to the piston rod 112, enabling a controlled displacement of the rod 112 within the reservoir 220 of the disposable part 200.

Figure 42A:
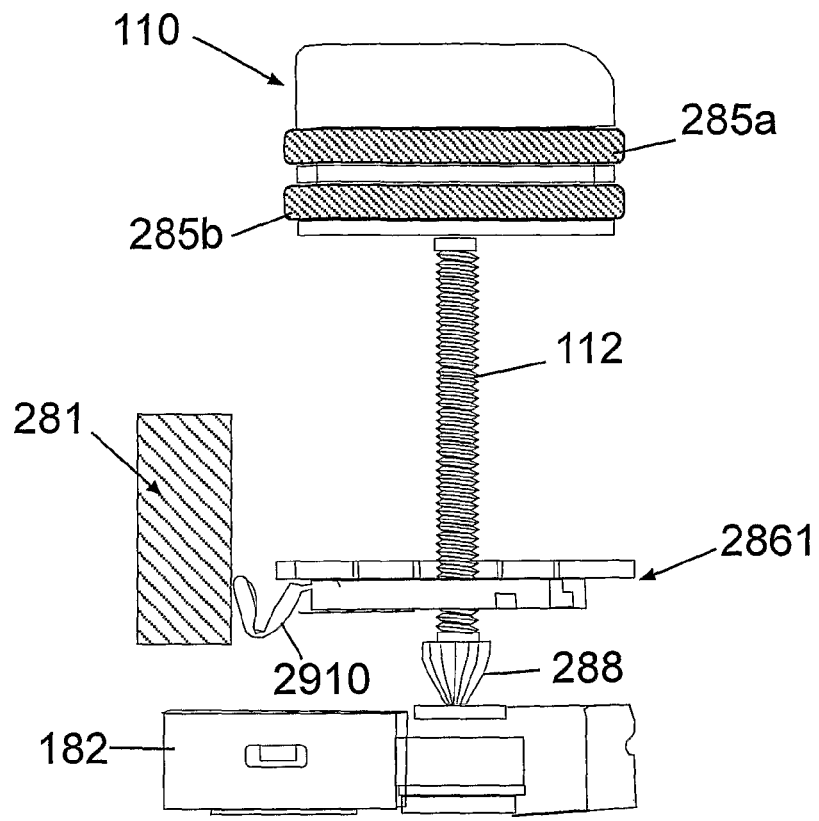
FIGS. 42a-42b are views of the automatic engagement mechanism before and after connection of a disposable part and a reusable part.
Figure 42B:
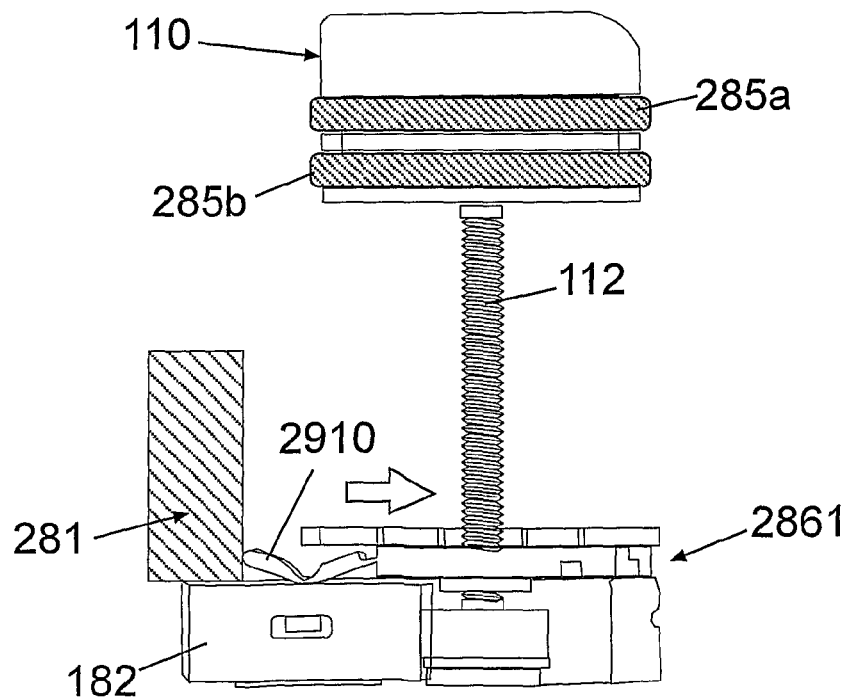

FIGS. 42a-42b further depict the engagement member 2861 and its engagement functionality. The actuating component (or "actuator") which presses the leaf 2910 may be the planetary gear 182 which is located in the reusable part 100. FIG. 42a illustrates the engagement operations when the two parts of the dispensing unit (100 and 200) are not connected. FIG. 42b illustrates the two connected parts (100 and 200). With reference to FIG. 42b, the housing of the planetary gear 182 presses the leaf 2910 which is constrained by the chassis 281 wall at one end. This causes lateral displacement (indicated by the single-headed arrow) of the engagement member 2861 so that the piston rod 112 is coupled to the small threaded opening 2901 of the engagement member 2861.

Figure 43A:
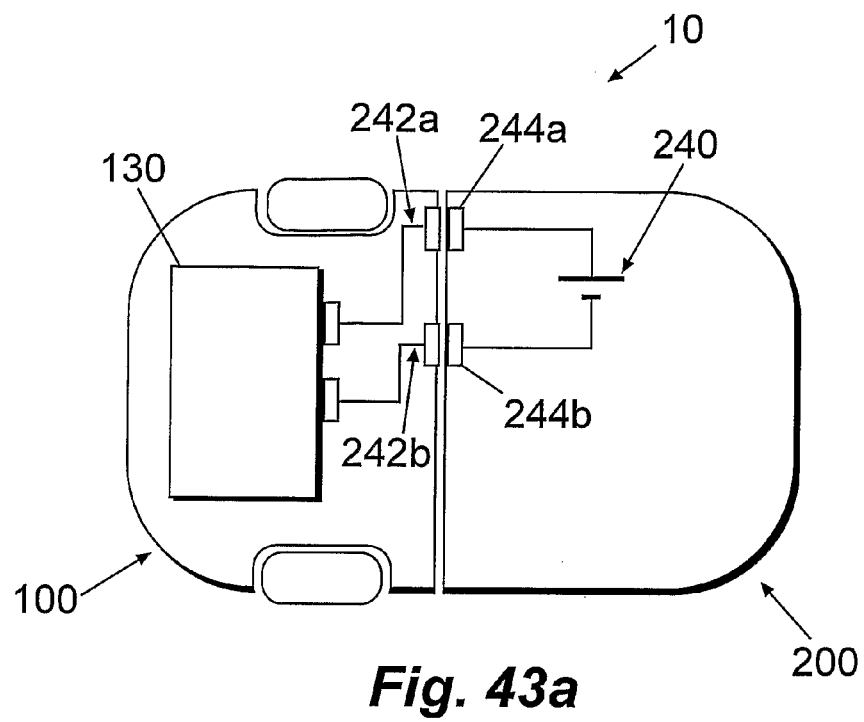
FIGS. 43a-43f are diagrams and views of a dispensing unit electrical circuit and the electrical coupling between a power source of the disposable part and electronics of the reusable part.
Figure 43B:
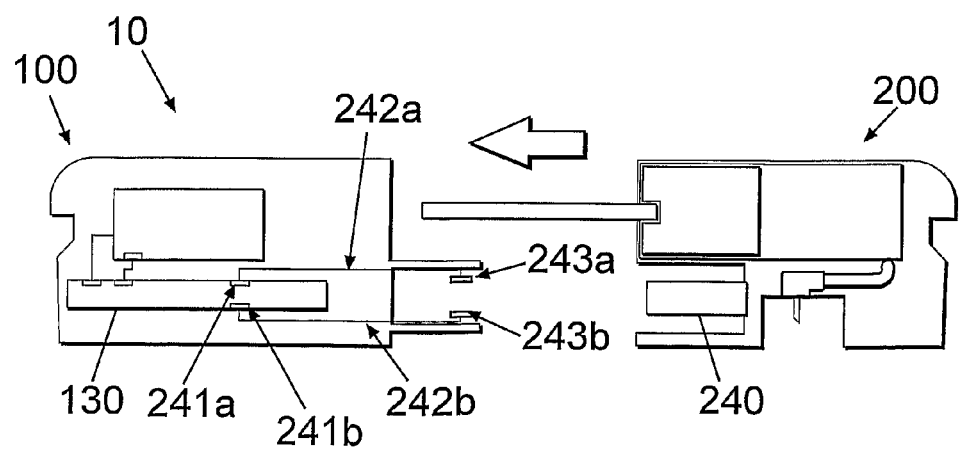

Referring to FIGS. 43a-43f, diagrams and views of an electrical circuit of a dispensing unit 10 are shown. The dispensing device 10 includes a power source 240 that may be located in the disposable part 200, while the electronics 130 may be located in the reusable part 100 of the two-part dispensing device 10. FIG. 43a illustrates schematically the electronic coupling between the power source 240 and electronics 130 via connectors 242a and 242b and contacts 244a and 244b, respectively. FIG. 43b illustrates the two parts (100, 200) before connection. In the embodiments illustrated in FIG. 43b the disposable part 200 includes the power source 240. The reusable part 100 includes two electrical connectors 242a and 242b, with their distal ends 243a and 243b, respectively, protruding out of the housing of the reusable part 100. The distal ends 243a and 243b are configured to establish electrical contact with the power source 240 upon connection of the reusable part 100 and the disposable part 200. The proximal ends 241a and 241b of the connectors 242a and 242b are connected to the electronics 130, which, in some embodiments, may be placed or otherwise connected to a PCB.

Figure 43C:
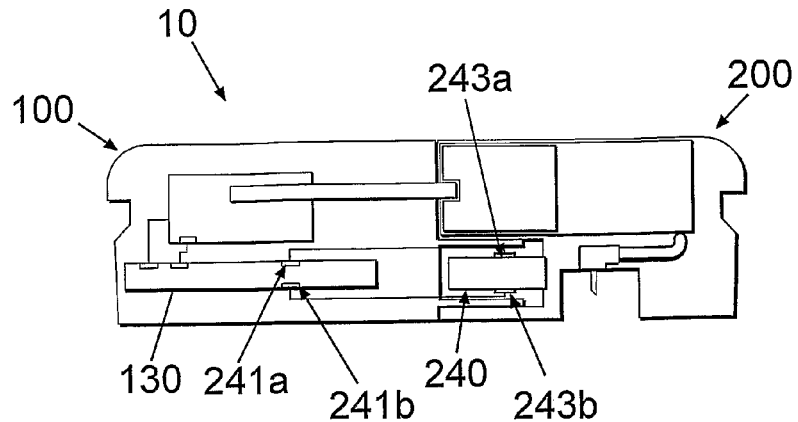

FIG. 43c illustrates an assembled dispensing unit 10 when the reusable part 100 is connected to the disposable part 200. As shown, when connected, the distal ends 243a and 243b of the connectors 242a and 242b come in contact with the electrical contacts of the power source 240 to enable current flow between the disposable part 200 and the reusable part 100.

In some embodiments, the connectors 242a and 242b can be located in the disposable part 200. Generally, however, connectors such as the connectors 242a and 242b are included within the reusable part 100 to reduce manufacturing costs of the disposable part 200.

In some embodiments, the connectors 242a and 242b may be mechanically durable and be resistant to mechanical fatigue resulting from recurrent connection and disconnection of the connectors 242a and 242b to the power source 240. For example, if a reusable part 100 is replaced every three months, and a disposable part 200 is discarded every three days, the connectors 242a and 242b will be connected and disconnected with the power source 240 at least thirty times. The protruded connectors 242a and 242b may also be exposed to unintentional mechanical wear and tear when the two parts of the dispensing unit 10 are disconnected (as illustrated in FIG. 43b).

Figure 43D:
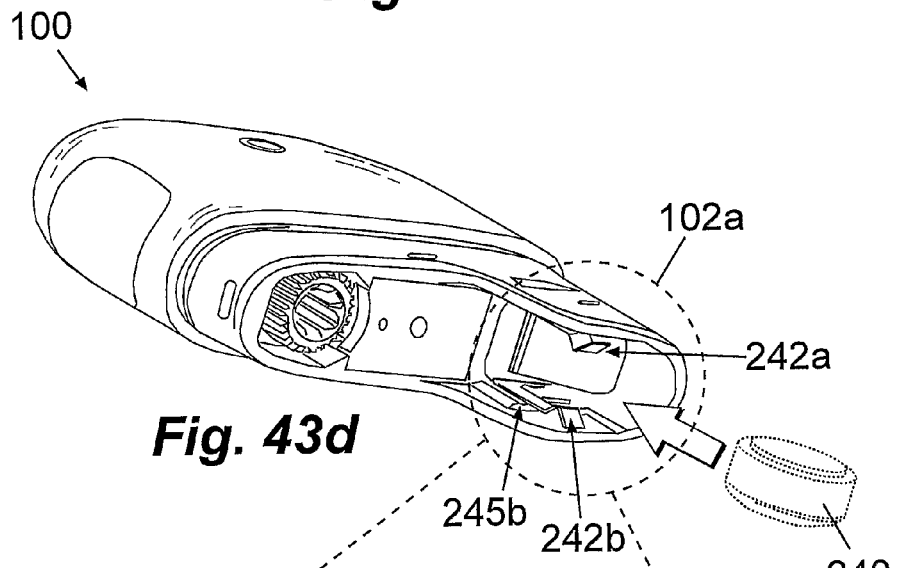

Referring to FIG. 43d, the housing of the reusable part 100 or its chassis may comprise a rigid extension 102a to accommodate the connectors 242a and 242b and protect them when the reusable part 100 is not connected to the disposable part 200. The rigid extension 102a can be provided with dedicated tracks to accommodate the two connectors 242a and 242b, and secure them in their positions. The tracks are designated by reference numerals 245a and 245b in FIGS. 43d-43f (in FIG. 43d only track 245b is shown).

Figure 43F:
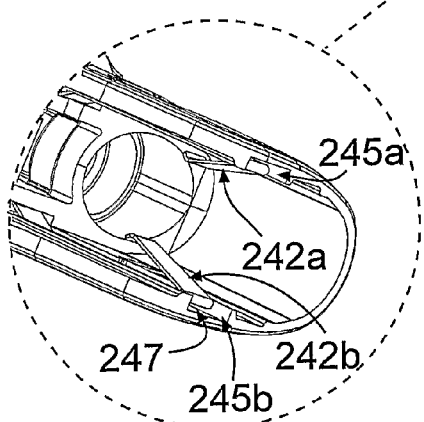
Figure 43E:
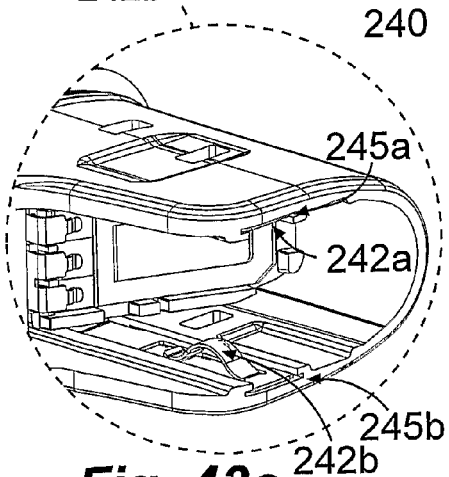

The connectors 242a and 242b are, in some embodiments, manufactured from a flexible material. The connectors, or at least their distal ends, may be structured to be resilient (e.g., may be configured as springs) so as to be able to connect and disconnect to and from the power source 240 without harming the power source's structure and operability, and to ensure establishment of proper mechanical contact between the connectors 242a and 242b and the electrical contacts of the power source 240 within a pre-determined range of possible varying spatial locations of the components. For example, a difference in the dimensions of a battery-based power source may be inherent to the power source's production process (e.g., two batteries from the same production line may slightly differ in their dimensions, for example, in their width dimension). In another example, differences in battery dimensions may be a result of chemical processes which occur inside the power source during its lifetime (i.e., the same battery may increase in its width dimension during its lifetime due to chemical processes, such as oxidation-reduction in fuel cells). The connectors 242a and 242b can be manufactured from thin metal strips, for example, stainless steel. In some embodiments, the distal ends of the metal strips are aligned with the edge of the rigid extension 102a, and the spring is formed either by folding the distal end of the strip or, as illustrated in FIG. 43e, by partially cutting out a portion of the strip and folding the portion while the strip remains aligned with the edge of the rigid extension 102a. As shown in FIG. 43f, the metal strips forming the connectors 242a and 242b may protrude from the rigid extension 102a with their protruding ends folded inwardly to form springs. The elasticity of the spring can be enhanced by allowing space 247 to form between the distal end of the connector and the walls of the rigid extension 102a such that the distal end can be pushed by the power source 240 toward the rigid extension 102a upon connection of the reusable part 100 and disposable part 200.

In some embodiments, the connectors 242a, 242b may be configured (through selection of, for example, materials with appropriate chemical properties) to prevent corrosion, etching, etc., which can harm their electrical functionality of transferring current/voltage therethrough. Construction of the connectors may include using different coatings, applying appropriate surface treatment procedures, etc.

Figure 44A:
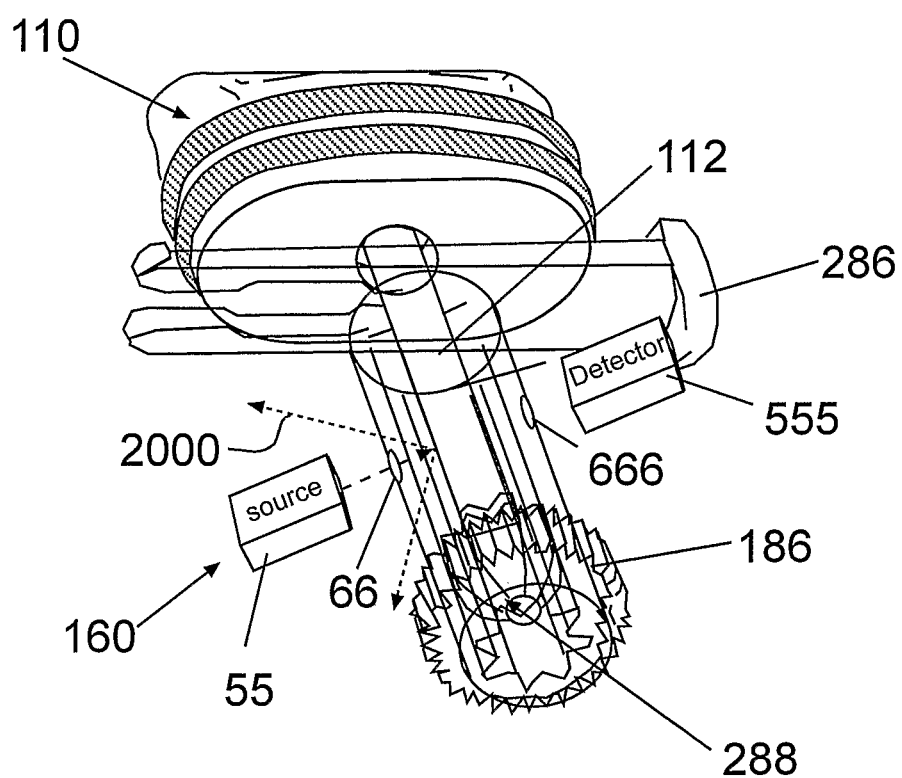
FIGS. 44a-44c are views and diagrams of a reservoir level indicator operating according to relative movement of a piston rod and a sleeve employing an optical sensor (FIGS. 44a-44b) and a screen interface (FIG. 44c).
Figure 44B:
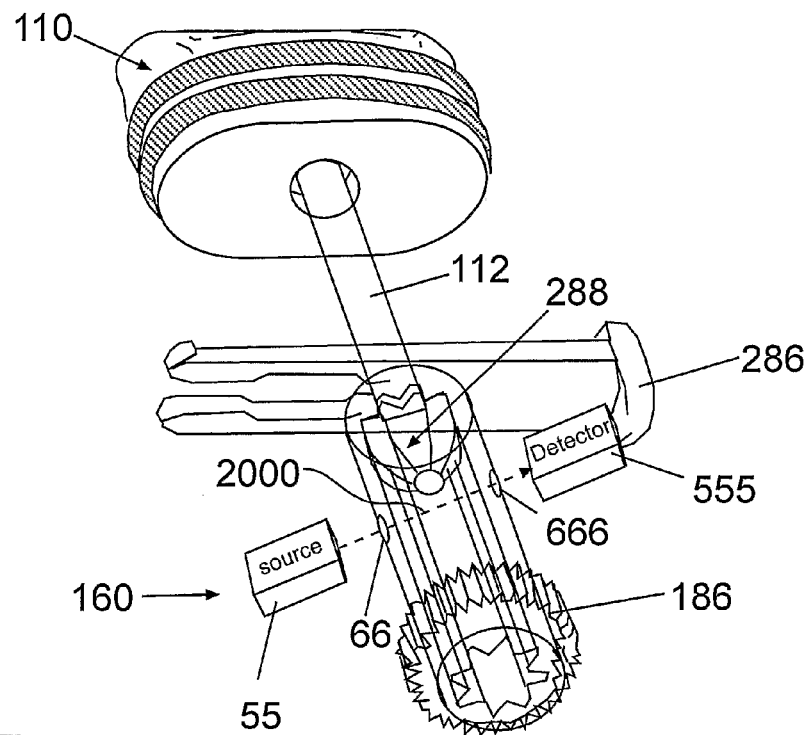
Figure 44C:
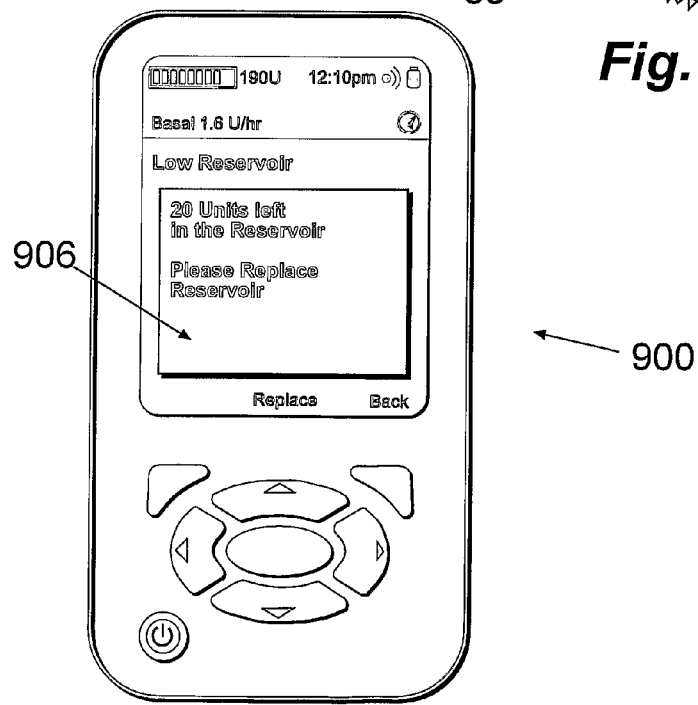

FIGS. 44a-44c illustrate a sensor 160 that can be used to determine fluid levels in a reservoir 220. The sensor 160 can alert/notify the user (either by displaying an alert/a notification on the dispensing unit 10 and/or a remote control unit 900, and/or by any other notification mechanisms) that it is time to replace the disposable part 200 and/or the reservoir 220. Such an alert and/or a notification may be generated when the reservoir fluid level has reached a certain pre-determined threshold level. The sensor 160 can also alert/notify the user as to how many units of therapeutic fluid are left in the reservoir 220 as shown, for example, in FIG. 44c. Generally, and as will be described in greater details below, the sensor 160 (also referred to as a fluid level monitoring mechanism) includes at least one energy source and at least one energy detector configured to detect energy emitted by the energy source. The sensor also includes a radiation regulator that regulates the energy that is received by the energy detector. The extent of the regulation of the energy may be based on the fluid level in the reservoir. For example, in some embodiments, the regulator is the piston rod that moves within the drive sleeve. When the piston rod is in one position (corresponding to a first fluid level in the reservoir), the piston rod may block the energy emission from the at least one energy source to the at least one detector. In another position, after the piston rod has been linearly displaced to push fluid from the reservoir (and thus changing the fluid level in the reservoir), the piston rod may no longer block the energy emission, thus enabling the detector to detect at least some of the emitted energy, which in turn is indicative of the fluid level in the reservoir. The fluid level monitoring mechanisms described herein may be used with other types of fluid dispensing devices. Furthermore, fluid level monitoring mechanisms, such as those described herein, may be used in conjunctions with other types of devices/systems (e.g., devices/systems where it may be necessary or desirable to know levels of fluids, e.g., fuel, used in such devices/systems) and not just with fluid dispensing devices.

With continued reference to FIGS. 44a-44b, the sensor 160 can include a light source 55 and a light detector 555. The light source 55 is configured to generate light to be detected by the light detector 555. As used herein, the term "light" refers to any electromagnetic radiation without limitation of wavelengths' range (e.g., may include the infrared spectrum). The source 55 and detector 555 may be located opposite each other and on each side of the sleeve 186, as shown in FIGS. 44a-44b. The sleeve 186 can also include openings 66 and 666, aligned opposite each other. When the source 55 and the detector 555 are aligned with the two openings 66 and 666, e.g., every one half of a turn of the sleeve 186, the light 2000 emitted by the light source 55 is passed through the opening 66. If the piston rod 112 is located inside the sleeve 186 such that the space between the openings 66 and 666 is occupied by the piston rod 112 or the tip 288 (i.e., the reservoir contains at least a predetermined threshold volume of therapeutic fluid), the light 2000 is reflected from the piston rod 112 or the tip 288 and does not pass through the opening 666 and into the detector 555 (as shown in FIG. 44a). If the piston rod 112 is removed from a portion of the sleeve 186 (i.e., the reservoir fluid level has reached a pre-determined threshold), the light 2000 emitted by the source 55 passes through the openings 66 and 666 and is detected by the detector 555 (as shown in FIG. 44b). The detector 555 sends signals to the controller/processor of the dispensing unit 10 corresponding to the amount of detected light, and the controller/processor processes this signal and may communicate an alert to the patient to replace the disposable part/reservoir (or otherwise advise the user of how much therapeutic fluid remains in the reservoir) either by displaying a message on a remote control unit's display 906 (as shown in FIG. 44c), and/or by generating an audio signal and/or a vibrational signal, and/or alerting the patient in any other way. In some embodiments, the number of openings in the sleeve 186 determines the resolution of the monitoring. For example, in the embodiments where the sleeve 186 is provided with two equally spaced openings (i.e., a single pair of oppositely aligned openings), the fluid level within the reservoir 220 may be monitored every one half of a turn of the sleeve 186, and in the embodiments where the sleeve 186 is provided with four (4) equally spaced openings (i.e., 2 pairs of oppositely aligned openings), the fluid level within the reservoir 220 may be monitored every one quarter of a turn of the sleeve.

In some embodiments, the sleeve 186 can be configured to have a plurality of aligned and opposite apertures (not shown), e.g., four (4) aligned pairs of apertures, similar to the apertures 66, 666. This plurality of apertures may be associated with corresponding light sources and detectors (similar to the source 55 and detector 555) to enable monitoring of several positions of the piston rod 112. This arrangement can thus be used to frequently monitor the amount of therapeutic fluid contained within the reservoir 220. In some embodiments, an array of sources and a corresponding array of detectors can be positioned along the sleeve 186. The sleeve can be structured to include a corresponding arrays of apertures, or include a longitudinal slit (not shown) to facilitate light passage.

In some embodiments (not shown in the figures), the sensor 160 can include a light source and a detector that can be positioned on the same side of the sleeve 186. Longitudinal slit(s)/aperture(s) provided in the sleeve 186 enable passage of emitted light into the interior of the sleeve 186. Thus, for example, if the piston rod 112 is located inside the sleeve 186 (i.e., the reservoir has some therapeutic fluid), the light is reflected from the piston rod and is detected by the detector. If the piston rod 112 is retracted from a portion of the sleeve (i.e., the reservoir fluid level has reached the predetermined threshold), the light emitted by the source passes through the slit/apertures and is not detected by the detector. Once light is no longer detected by the detector, the detector may send a signal to a controller/processor of the dispensing unit. The processor controller/processes this signal and may communicate an alert to the patient to replace the disposable part/reservoir (or otherwise advise the patient of how much of the therapeutic fluid remains in the reservoir), either by displaying a message on the remote control unit's display, and/or generating an audio signal and/or a vibrational signal, and/or alerting the patient in any other way. Alternatively and/or additionally, the tip 288 of the piston rod can be used to reflect light, for example, by virtue of white coloring of tip 288.

Figure 45A:
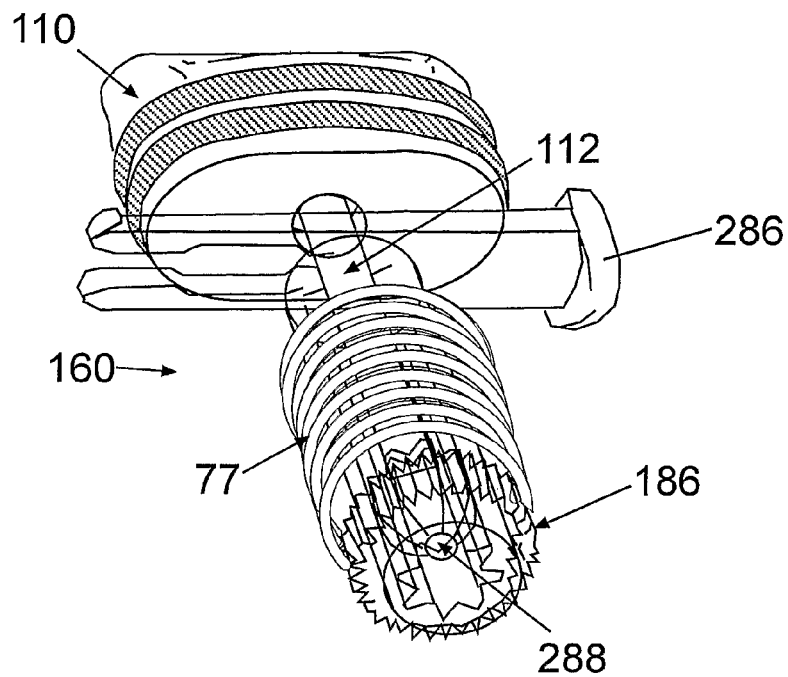
FIGS. 45a-45b are diagrams of a reservoir level indicator operating according to the relative movement of a piston rod and a sleeve employing magnetic induction sensor.
Figure 45B:
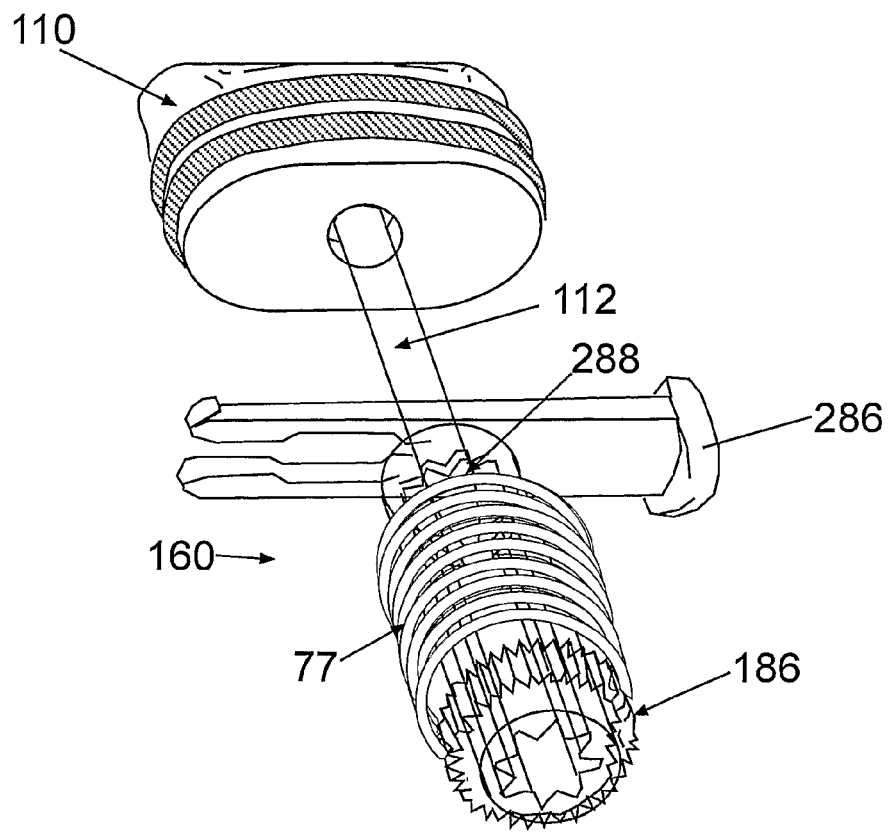

Referring to FIGS. 45a-45b, diagrams of a sensor to monitor reservoir fluid level are shown. The sensor 160 includes a magnetic coil 77 having a plurality of windings (e.g., a solenoid) surrounding a sleeve 186. The piston rod 112 and/or tip 288 may be constructed, at least partially, from a metallic material such as ferrite (or partially coated with such a material). The displacement of the piston rod 112 and tip 288 within the magnetic coil 77 alters the inductance (L) of the coil 77. FIG. 45a illustrates a first position of the rod 112 and tip 288 in relation to the sleeve 186 and the coil 77. FIG. 45b illustrates a second position of the rod 112 and tip 288 after piston's displacement. The change of inductance (L) of the coil 77 correlates to the position of the piston rod 112 or tip 288, and is indicative of the amount of therapeutic fluid that resides within the reservoir. Measurement of the inductance (L) can be done by RLC circuit or in other ways. The signal is processed by a processor which can communicate a notification and/or alert the patient.

In some embodiments, other detection mechanism methodologies and techniques may be implemented to determine the reservoir fluid level based on, for example, magnetic signals (e.g., the Hall Effect), capacitance differentiation, mechanical detection, etc.

Referring to FIGS. 46a-46e, diagrams of an occlusion sensor 140 to monitor occlusion in the fluid path from the reservoir 220 to the body of a user/patient, i.e., in the connecting tube 230 and/or connecting lumen 250 and/or subcutaneously insertable cannula (when the dispensing device is attached to the body) are shown. Such an occlusion may prevent delivery of therapeutic fluid to the patient's body. The occlusion sensor 140 can be used to alert the user (either by displaying an alert on the dispensing unit 10 and/or the remote control unit 900 and/or by activating any other notification mechanism) that a partial or complete occlusion has occurred and/or suggest replacing the disposable part 200 (in a two-part dispensing unit) and/or the cradle unit and/or the occluded cannula. It is to be noted that occlusion sensors such as those described herein may be used with other types of fluid dispensing devices/units. Furthermore, occlusion sensors such as those described herein may be used in conjunction with other devices and systems (e.g., devices/systems where it may be necessary or desirable to know whether a state of occlusion has been reached) and not just with fluid dispensing devices.

In some embodiments, the occlusion sensor 140 can be located in the reusable part 100 of a two-part dispensing device or may be shared between both parts (100, 200).

Figure 46A:
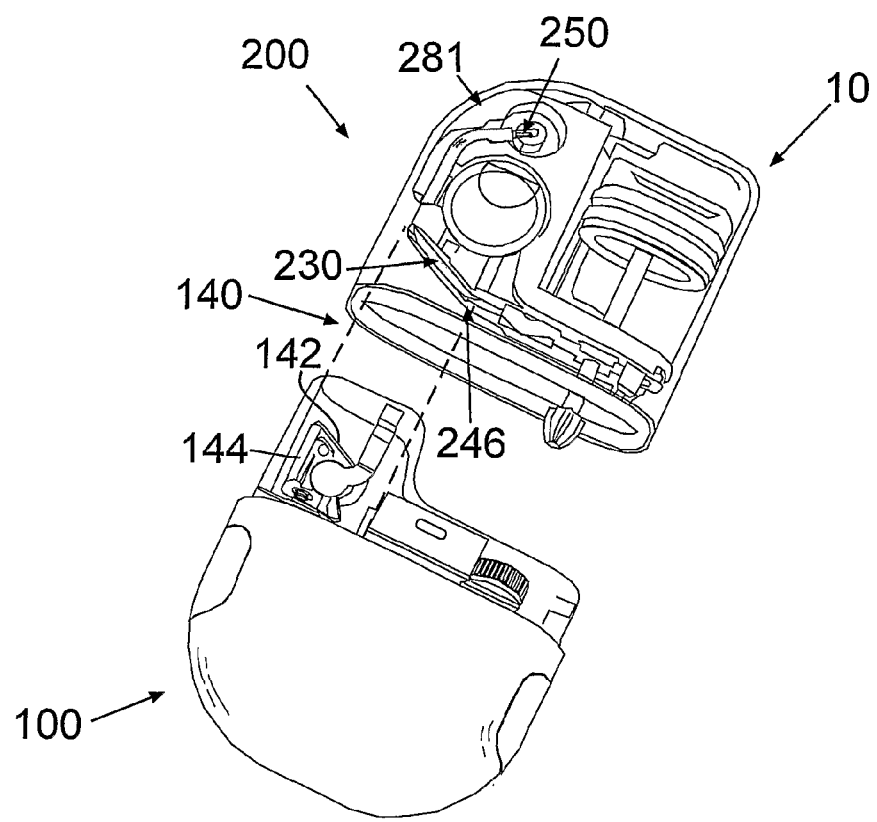

FIG. 46a illustrates a dispensing device/unit 10 comprising two parts: a reusable part 100 having at least a portion of the occlusion sensor 140, and a disposable part 200 having a portion of the occlusion sensor 140 and a connecting tube 230. The reusable part 100 includes a sensing element 142 and a spring biased slider 144 coupled to the sensing element 142. The sensing element 142 is electrically coupled to the electronics 130, (e.g., a processor-based device). The connecting tube 230 of the disposable part 200 is disposed at least in part within a track 246 of the sensory mechanism. The track 246 can be an integral portion of the disposable chassis 281.

Figure 46B:
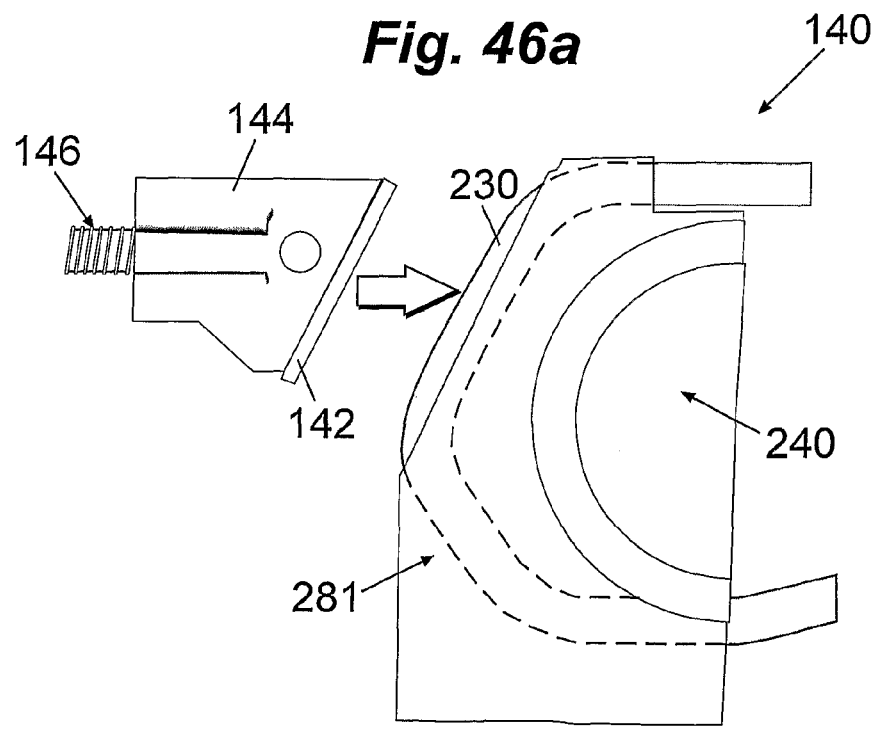

FIGS. 46b-46e illustrate the occlusion sensor 140 when the disposable part 200 is disconnected from the reusable part 100 (as shown in FIGS. 46b and 46d), and when the two parts (100 and 200) are connected (as shown in FIGS. 46c and 46e). Referring to FIGS. 46b and 46d, the dimensions of the connecting tube 230 and track 246 are selected so that the track 246 does not exert forces on the connecting tube's 230 wall.

Referring to FIGS. 46c and 46; the slider 144 of the reusable part 100 contacts the track 246 of the disposable part 200, causing the connecting tube 230 to be flattened so that the contact area between the connecting tube 230 and the flat sensing element 142 is increased to allow a reliable measurement and a lower Signal-to-Noise Ratio ("SNR"). A spring 146 retains the sensing element 142 in contact with the connecting tube 230.

When an occlusion occurs, the pressure within the tube 230 increases, thus causing the resilient and flexible tube 230 to inflate resulting in an increase in the forces exerted on the sensing element 142. The force (pressure) is measured by the sensing element 142, which transmits to the processor/controller a signal corresponding to the measured force, and when a pre-determined threshold value is exceeded, the processor/controller (e.g., of the electronics 130) determines that an occlusion occurred. The processor/controller then causes a notification signal to be generated that is used to notify the user that an occlusion has occurred and that the cannula, the cradle and/or the disposable part 200 has to be replaced. The controller may automatically halt/suspend the operation of the dispensing unit 10 in response to receipt of a signal indicative of an occlusion state in the fluid path from the reservoir 220 to the user/patient. The user may disconnect the operating dispensing unit and inspect the unit to eliminate the possibility of an occlusion in the portion of the fluid path residing within the disposable part 200. Appearance of drops at the tip of the connecting lumen of an operating dispensing unit may indicate that a distal occlusion exists, and that consequently, only the cannula and cradle need to be replaced. Notification can be visual, audible, vibrational, etc., and can be made via the dispensing unit 10, the remote control unit 900 or both.

In some embodiments, the sensing element 142 can be configured as a tactile/force/pressure sensor. Further descriptions of occlusion sensors in fluid delivery devices are provided, for example, in co-pending/co-owned U.S. patent application Ser. No. 11/810,854, the content of which is hereby incorporated by reference in its entirety.

Unlike conventional occlusion sensors for infusion pumps which monitor the driving mechanism, a occlusion sensing mechanism that is predicated on the behavior of a connecting tube in a device employing a plunger/piston-like pumping mechanism facilitates quick and sensitive occlusion detection. Detection of an occlusion according to the present disclosure can occur within minutes to a couple of hours after the occlusion condition has occurred. In contrast, in conventional sensory mechanisms, occlusion is typically detected twelve (12) or more hours after the occurrence of an occlusion.

In some embodiments, the sensor 140 requires that the connecting tube 230 have certain mechanical, physical and chemical characteristics (e.g. diameter, resiliency, bio-compatibility) to enable occlusion detection using the connecting tube 230, as described in co-pending/co-owned International Patent Application No. PCT/IL08/000,864, the content of which is hereby incorporated by reference in its entirety.

In some embodiments, the fluid delivery device/system can communicate with the user to notify the user of alerts, alarms, errors, status, etc. Notification can be performed in various ways such as visual, audible, vibrational and/or the like.

Visual notification can be made by employing the display/screen 906, such as a Liquid Crystal Display ("LCD") of the remote control unit 900, as shown for example in FIGS. 44*c* and 49*a*-49*c*. A user-friendly interface that includes a set of menus and screens accompanied by graphical symbols/icons may be implemented on the display 906. The user interface can be controlled by buttons/switches.

In some embodiments, visual notification can be further provided in the dispensing device's display, for example, a display located in the reusable part 100 in a two-part dispensing device, as described for example in co-pending/co-owned International Patent Application No. PCT/IL08/001,057, the content of which is hereby incorporated by reference in its entirety.

Audible notification can be employed in the remote control unit 900, and may be configured as a "beep" sound or as a tailored ringtone associated with a specific function/notification/message. Audible notifications can be further employed in the dispensing unit 10. A buzzer can be located on the housing of the dispensing unit 10. In a two-part dispensing unit 10, the buzzer is preferably located in the reusable part 100. The buzzer can be coupled either to the external side or to the internal side of the housing.

Figure 47:
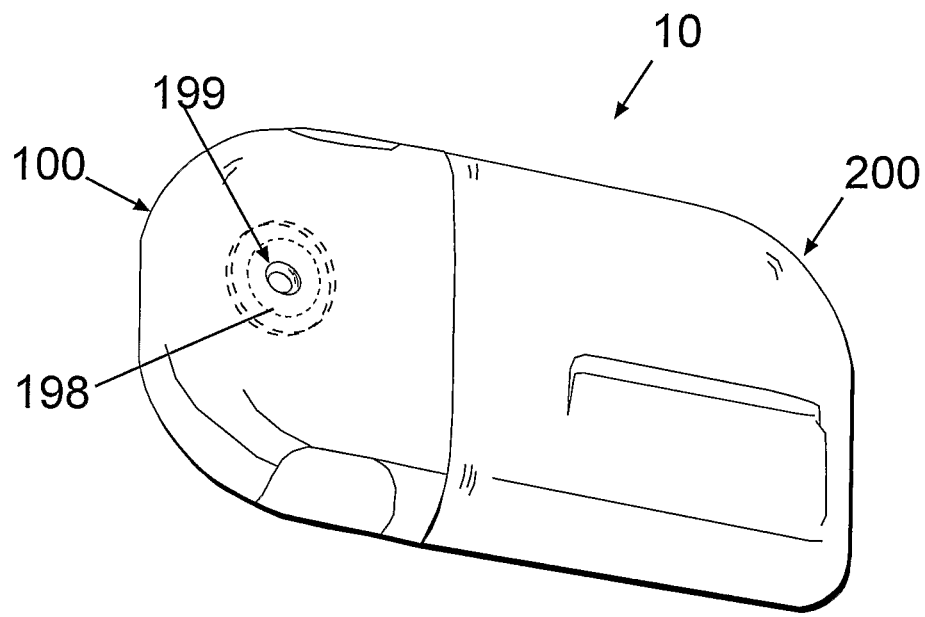
FIG. 47 is a perspective view of a reusable part including a sealable vent aperture/port.

As illustrated in FIG. 47, in some embodiments, a buzzer 198 requires an aperture/port 199 to allow air flow between the internal cavity of the dispensing unit 10 and the external environment. The buzzer 198 can be coupled to the housing in various ways such as by adhesives (e.g., application of glue), ultrasonic soldering, laser welding, and the like. Furthermore, the buzzer 198 is configured, in some embodiments, to resonate in a frequency that will provide an audible sound while not harming/interfering the other components of the dispensing unit 10, such as the electronics 130.

In some embodiments, the aperture/port 199, which enables air flow into the internal cavity of the dispensing device 10, is also required to facilitate operation of a power source, such as a power source comprising one or more Zinc-air batteries, and also facilitate achieving pressure equilibration, and enhancing buzzer sound, as described in co-pending/co-owned International Patent Application No. PCT/IL08/000,999, the content of which is hereby incorporated by reference in its entirety.

In some embodiments, the dispensing device 10 is sealed and waterproof (to eliminate the ingression of liquids, e.g., water). The extent of sealing may conform, for example, to IPX8 performance standard, and may be determined based on the dispensing unit's requirements to operate in different conditions, such as rain conditions, operating in a bath, etc. Thus, the aperture/port 199 is, in some embodiments, sealable. This can be done by providing the aperture/port 199 with a selective membrane (e.g. Gore-Tex©) which enables air/gas passage but prevents liquids ingression. A sealable aperture/port of a dispensing unit is described in co-pending/co-owned International Patent Application No. PCT/IL08/001,000, the content of which is hereby incorporated by reference in its entirety.

In some embodiments, the two-part dispensing unit 10 may further require sealing between the disposable part 200 and the reusable part 100 to prevent ingression of liquids into the internal cavity of the dispensing unit 10 (which may, for example, harm the electronic components and cause irreversible damage to the dispensing unit).

Figure 48A:
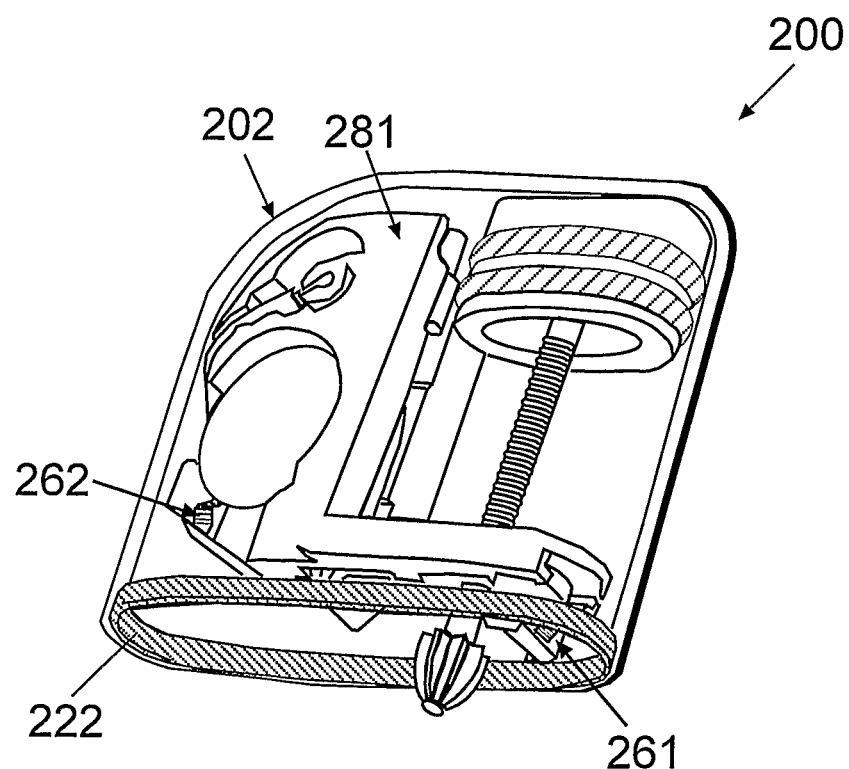
FIGS. 48a-48b are views of a disconnected dispensing unit and sealing gaskets on a disposable part housing (shown in FIG. 48a) and a reusable part chassis and housing (shown in FIG. 48b).
Figure 48B:
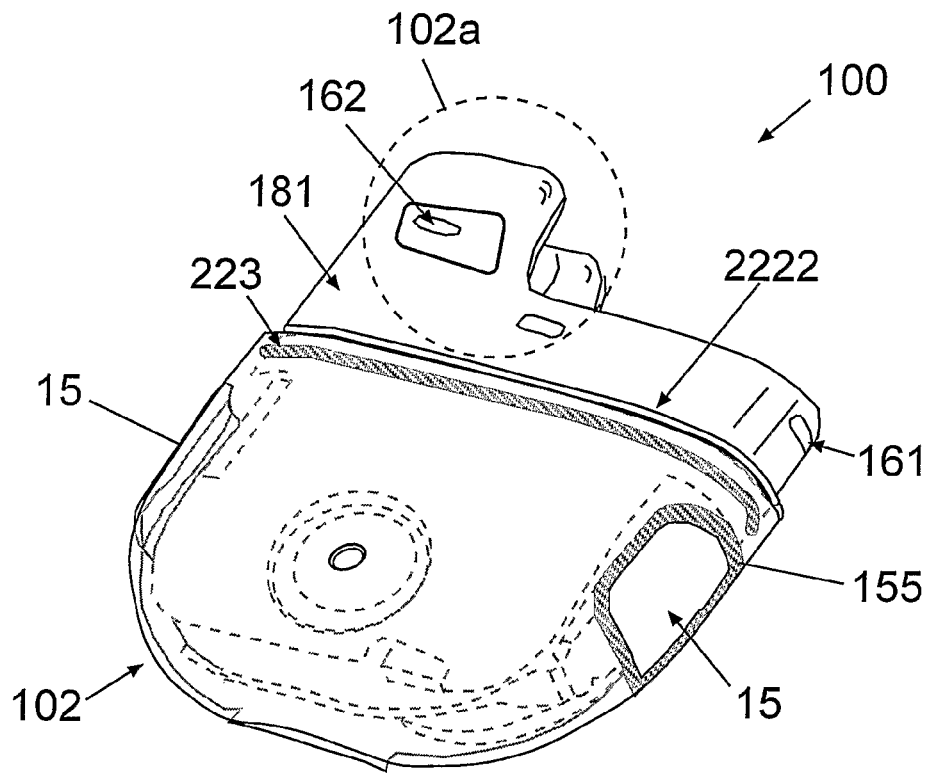

FIGS. 48*a*-48*b* illustrate the sealing and the secure connection of the two parts (100 and 200). FIG. 48*a* illustrates the disposable housing 202 with a seal/gasket 222 secured along the perimeter of the housing's opening. The seal/gasket 222 can be made out of rubber and/or plastic materials, including materials such as EPDM ("Ethylene Propylene Diene Monomer') rubber or TPE ("Thermoplastic Elastomer"), and can be structured in various profiles. The seal/gasket 222 can be disposed either on the external or internal side of the housing 202, or on both. Securing the seal/gasket 222 to the perimeter of the housing 202 can be performed by applying over-molding and/or double injection procedures. As shown in FIG. 48*b*, the housing and/or the chassis of the reusable part 100 is provided with matching protrusion(s) 2222 which squeezes the seal/gasket 222 upon connection of the disposable part 200 and the reusable part 100. In some embodiments, the seal/gasket 222 can be provided at the reusable part 100.

FIG. 48*b* illustrates a reusable part 100 provided with a peripheral protrusion 2222 which is coupled to the seal/gasket 222 of the disposable part 200 upon connection of the reusable part 100 and the disposable part 200 to seal the dispensing unit. The reusable part 100 can be also provided with a seal/gasket 223 which supports the reusable chassis 181 within the housing 102 of the reusable part and seals the interface therebetween. The seal/gasket 223 can be disposed either on the housing 102 or the chassis 181 of the reusable part 100. Thus, at least one of the reusable part housing, the chassis of the reusable part, the disposable part housing and/or the chassis of the disposable part may include a seal or a gasket such that upon connection of the reusable part to the disposable part, a device sealing condition is established.

As illustrated in FIG. 48b, the buttons/switches 15 can be sealed by a dedicated seal 155 or, in some embodiments, by applying the buttons/switches 15 using an over-molding process.

In some embodiments, a securable connection between the two parts (100 and 200) is implemented using a snap-fit arrangement that includes one or more latches 261 and 262 provided at the disposable chassis and/or the housing of the disposable part, as shown in FIG. 48a, and one or more matching recesses/grooves 161 and 162 provided at the reusable chassis and/or housing of the reusable part, as shown in FIG. 48b, or vice versa.

In some embodiments, the extension 102a of the reusable part 100 can provide further support for the alignment and connection of the two parts (100 and 200) upon connection and disconnection.

In some embodiments, further supporting and/or strengthening of the sealing and/or connection of the two parts (100 and 200) may be performed by adhesion, ultrasonic soldering, laser welding, etc., of the various components of the dispensing device/unit (as well as the cradle and/or cannula cartridge units).

Figure 49A:
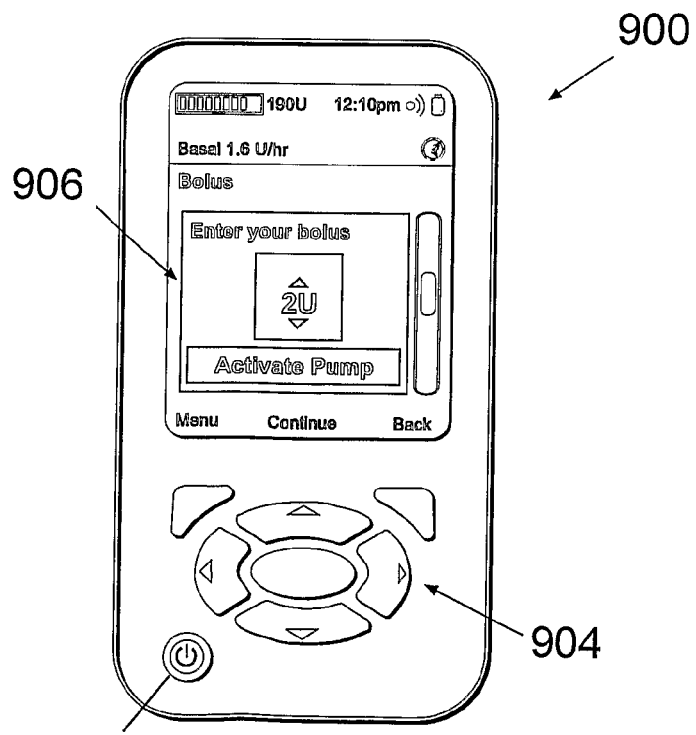
FIGS. 49a-49c are diagrams of a remote control unit of the fluid delivery system, including a screen with GUI (FIG. 49a-b) and a blood glucose monitor (FIG. 49c).
Figure 49B:
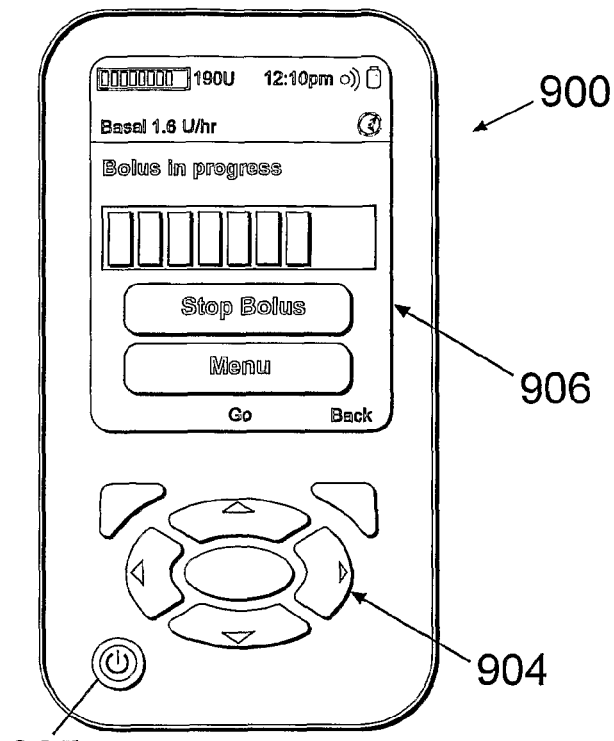
Figure 49C:
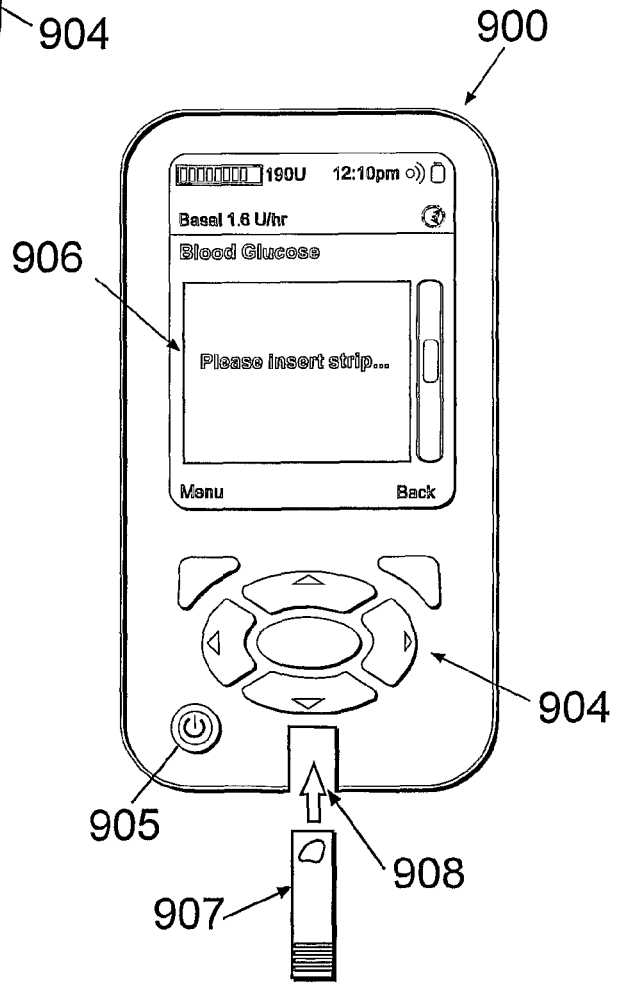

Referring to FIGS. 49a-49c, diagrams of a remote control unit 900 of a fluid delivery device are shown. As noted, FIG. 44c illustrates a remote control unit 900 that may be used to indicate the amount of units of insulin (e.g., 190U) remaining in the reservoir, as well as perform numerous other functions regarding the setup and operation of the dispensing device/unit and/or system as a whole.

Referring to FIG. 49a, the remote control unit 900 includes, in some embodiments, a display/screen 906 and may include operating button(s)/switch(s) 904, though the screen may be touch-sensitive in addition to or in place of the operating buttons 904. The screen may further employ multi-touch technology. The remote control unit 900 can also include an on/off button/switch 905 that enables a user to turn on and off the unit 900. It should be noted that a patient can also control/instruct/command the operation of the dispensing device by buttons/switches (designated by reference numeral 15) that are disposed on the dispensing device. Such buttons/switches are described, for example, in co-pending/co-owned International Patent Application No. PCT/IL08/001,001, the content of which is hereby incorporated by reference in its entirety. Additional operating buttons/switches can be located in the reusable part, and may also include a screen to communicate with the patient, as also described in co-pending/co-owned International Patent Application No. PCT/IL08/001,057, the content of which is hereby incorporated by reference in its entirety.

The remote control unit 900 can communicate operating/control instructions (e.g., basal and/or bolus fluid dispensing commands) to a controller (e.g., the processor comprising part of electronics 130) of the dispensing unit 10 and/or receive messages (e.g., alerts and warnings) from the processor (e.g., such messages including low battery warning, low volume of fluid in reservoir warning, etc.). The remote control unit 900 can also display such instructions, warnings, and alerts, as well as display current state of the device (e.g., dispensing bolus dose of insulin). For example, the remote control unit 900 can indicate basal dosage rates of insulin dispensing (e.g., 1.6 U/hr). As described above, such dispensing rates (whether bolus or basal) may be dispensed by the linear movement of the piston rod 112. The display of the remote control unit 900 can also indicate progress of dispensing of the bolus, as well as, enable the user to stop dispensing of insulin (see FIG. 49b), or activate the pump to dispense insulin (see FIG. 49a).

The remote control unit 900 can communicate with the dispensing unit 10 via wireless communication as well as by any other suitable communication methodologies, for example induction, RF transmission, IR transmission, etc., as well as by wired communication. Communication between the remote control unit 900 and dispensing unit 10 can be unidirectional (i.e., one-way communication) or bi-directional (i.e., two-way communication).

In some embodiments, the remote control unit 900 may be implemented using a PC, a laptop, a watch, a cellular phone, a music or multimedia player (e.g., an iPod), a Personal Digital Assistant ("PDA") or any other suitable remote commander/controller.

In some embodiments, the remote control unit 900 may include a glucose sensor which is coupled to the remote control unit 900, as illustrated in FIG. 49c. The sensing of glucose concentration levels can be performed by various sensing techniques such as, for example, electrochemical, optical or the like. In some embodiments, a blood sample of the patient can be associated with a conventional test strip 907 insertable to a dedicated port 908 which is located in the remote control unit 900.

In some embodiments, the remote control unit 900 can further include dedicated software elements (computer program products) to cause a processor to of the remote control unit to perform such operations as bolus selection procedures, as described, for example, in U.S. patent application Ser. No. 12/051,400, the content of which is hereby incorporated by references in its entirety, and Carbohydrate-to Insulin Ratio ("CIR") estimation as described, for example, in co-pending/co-owned International Patent Applications Nos. PCT/US08/07703 and PCT/IB08/003,185, the contents of which are hereby incorporated by references in their entireties.

In some embodiments, the fluid delivery device/system can further comprise a sensing apparatus to monitor bodily analyte(s) e.g., monitoring of concentration levels of glucose in the interstitial fluid ("ISF"). The sensing apparatus may comprise sensing elements, dedicated processing elements, delivery modules and components, etc. Sensing of the analyte(s) can be performed within the body ("in vivo") or outside the body, and may be performed by various techniques such as optical techniques, electrochemical techniques, etc. The sensing apparatus can measure analyte concentration at measurement rates (or frequencies) that are either continuous, semi-continuous, periodic or discrete.

A sensing apparatus may include at least two electrodes to sense the concentration level of glucose in the ISF, and are disposed proximate to the distal end of the cannula so that when the cannula is subcutaneously inserted, the electrodes are also subcutaneously inserted. The electrodes generate electrical signal representative of the glucose level which is electrically transferred (by wires and/or disposed conductors) to a processing element located in the dispensing unit (e.g., in an electronics module, such as any of the electronics 130 described herein, in the reusable part of a two-part dispensing unit). Such a sensing apparatus is described in detail in co-pending/co-owned U.S. patent application Ser. No. 11/963,481, the content of which is hereby incorporated by reference in its entirety.

In some embodiments, a dispensing apparatus and sensing apparatus (constituting a "system") is configured to operate in one or more of a closed loop, an open loop, or a semi-open loop mode. In a closed loop mode, an analyte concentration is sensed by a sensor and determined by a processor, and based on the determined concentration, the processor generates commands to cause a dispensing apparatus to dispense one or more therapeutic fluids to the human body. In an open loop mode, the sensing and dispensing functions are not linked. A device/system which operates in this mode could indicate a value for the determined analyte concentration, but no feedback control is exercised over the rate of dispensing. A user interface, or other ways by which a user can communicate commands to the device, enables the user to dispense the therapeutic fluid. In the semi-closed mode, the sensing occurs as described above for the closed loop mode. However, the device/system can wait for confirmation from a user, or alternatively can request such confirmation, possibly via a user interface, before dispensing the therapeutic fluid in the amounts that might be needed based on the determined analyte concentration.

Example embodiments of the methods and components of the present disclosure have been described herein. As noted elsewhere, these example embodiments have been described for illustrative purposes only, and are not limiting. Other embodiments are possible and are covered by the disclosure. Such embodiments will be apparent based on the teachings contained herein. It is also understood that various modifications may be made without departing from the spirit and scope of the invention. Accordingly, other embodiments are within the scope of the following claims.

What is claimed is:

1. A portable therapeutic fluid dispensing device comprising:
   a first housing and a second housing;
   a reservoir for storing a therapeutic fluid; and
   a driving mechanism comprising:
      a piston;
      a piston rod having a first end mechanically coupled to the piston, the piston rod being at least partially threaded; and
      an engagement member configured for threaded engagement with the piston rod, the engagement member being further configured to selectively enable a controlled displacement of the piston rod within at least the reservoir via the threaded engagement, and a manual displacement of the piston rod within at least the reservoir,
   wherein the engagement member is movable between a first position in which the engagement member is in threaded engagement with the piston rod, and a second position in which the engagement member is released from the threaded engagement with the piston rod to allow manual displacement of the piston rod and the engagement member comprises means for moving the engagement member from the second position to the first position upon connection of the first housing and the second housing.

2. The device according to claim 1, wherein the engagement member defines a first non-threaded opening and a second threaded opening.

3. The device according to claim 2, wherein the first non-threaded opening is adjacent the second threaded opening.

4. The device according to claim 1, further comprising a first housing and a second housing connectable to the first housing, wherein the driving mechanism comprises a first portion and a second portion mechanically coupleable to the first portion upon connection of the first housing and the second housing, the second portion of the driving mechanism comprising the piston, the piston rod, and the engagement member.

5. The device according to claim 3, wherein the engagement member is moved from the second position to the first position upon connection of the first housing and the second housing.

6. The device according to claim 1, wherein the means comprises an extension that moves the engagement member to the first position when pressed upon connection of the first housing and second housing.

7. The device according to claim 1, wherein the means is a leaf spring that moves the engagement member to the first position when pressed upon connection of the first housing and the second housing.

8. The device according to claim 3, wherein at least a portion of the second housing defines at least a portion of the reservoir.

9. The device according to claim 3, wherein the second housing includes a skin-adherable base configured to receive the first housing.

10. The device according to claim 1, further comprising one or more sensors for sensing a threshold position of the piston.

11. The device according to claim 10, wherein the one or more sensors comprises at least one energy source and at least one energy detector configured to detect energy emitted by the energy source.

12. The device according to claim 11, further comprising radiation regulator for regulating an energy received by the energy detector.

13. The device according to claim 12, wherein the radiation regulator is the piston, the piston regulates the energy received by the energy detector by blocking or unblocking the energy as it moves.

14. The device according to claim 13, wherein the piston blocks the energy received by the energy detector until the piston moves past a threshold position.

15. The device according to claim 10, further comprising alert means for alerting a user when the piston has reached the threshold position.

16. The device according to claim 15, wherein the alert means generates one or more of an visual signal, audio signal, or a vibrational signal to the user when the piston has reached the threshold position.

17. The device according to claim 10, wherein the piston is configured to generate an inductance that varies with its position, the one or more sensors include an inductance sensor for sensing the inductance of the piston.

18. The device according to claim 1, further comprising an occlusion sensor for detecting occlusion in a fluid path from the reservoir to a body of a user.

19. The device according to claim 1, further comprising a controller operatively connected to the occlusion sensor, the controller being configured to suspend the operation of the unit when an occlusion is detected by the occlusion sensor.

* * * * *